US010030231B2

(12) United States Patent
Dormitzer et al.

(10) Patent No.: US 10,030,231 B2
(45) Date of Patent: Jul. 24, 2018

(54) INFLUENZA VIRUS REASSORTMENT

(71) Applicants: Seqirus UK Limited, Berkshire (GB); Synthetic Genomics Vaccines, Inc., La Jolla, CA (US)

(72) Inventors: Philip Dormitzer, Cambridge, MA (US); Peter Mason, Cambridge, MA (US); Pirada Suphaphiphat, Cambridge, MA (US); Daniel Gibson, La Jolla, CA (US); David Wentworth, La Jolla, CA (US); Timothy Stockwell, La Jolla, CA (US); John Glass, La Jolla, CA (US)

(73) Assignees: Seqirus UK Limited, Maidenhead, Berkshire (GB); Synthetic Genomics Vaccines, Inc., La Jolla, CA (US)

( * ) Notice: Subject to any disclaimer, the term of this patent is extended or adjusted under 35 U.S.C. 154(b) by 0 days.

(21) Appl. No.: 14/762,439

(22) PCT Filed: Jan. 23, 2014

(86) PCT No.: PCT/IB2014/058501
§ 371 (c)(1),
(2) Date: Jul. 21, 2015

(87) PCT Pub. No.: WO2014/115104
PCT Pub. Date: Jul. 31, 2014

(65) Prior Publication Data

US 2015/0353900 A1 Dec. 10, 2015

Related U.S. Application Data

(63) Continuation of application No. 13/841,752, filed on Mar. 15, 2013.

(60) Provisional application No. 61/849,325, filed on Jan. 23, 2013.

(30) Foreign Application Priority Data

Mar. 15, 2013 (GB) .................................. 1304827.7

(51) Int. Cl.

| | |
|---|---|
| ***C12N 7/00*** | (2006.01) |
| ***A61K 39/145*** | (2006.01) |
| ***C07K 14/005*** | (2006.01) |
| ***C12N 5/071*** | (2010.01) |
| *A61K 39/00* | (2006.01) |

(52) U.S. Cl.
CPC .............. *C12N 7/00* (2013.01); *A61K 39/145* (2013.01); *C07K 14/005* (2013.01); *C12N 5/0686* (2013.01); *A61K 2039/525* (2013.01); *C12N 2510/02* (2013.01); *C12N 2760/16121* (2013.01); *C12N 2760/16122* (2013.01); *C12N 2760/16134* (2013.01); *C12N 2760/16151* (2013.01); *C12N 2760/16221* (2013.01); *C12N 2760/16234* (2013.01); *C12N 2760/16251* (2013.01)

(58) Field of Classification Search
None
See application file for complete search history.

(56) References Cited

U.S. PATENT DOCUMENTS

2013/0189303 A1* 7/2013 Zhou .................... A61K 39/145 424/206.1

FOREIGN PATENT DOCUMENTS

| | | | |
|---|---|---|---|
| WO | 2001/004333 | A1 | 1/2001 |
| WO | 2009/048885 | A2 | 4/2009 |
| WO | 2011/012999 | A1 | 2/2011 |
| WO | 2011/145081 | A1 | 11/2011 |
| WO | 2013/087945 | A2 | 6/2013 |
| WO | WO 2013/087945 | A2 | 6/2013 |

OTHER PUBLICATIONS

Zhange et al., A One-Plasmid System to Generate Influenza Virus in Cultured Chicken Cells for Potential Use in Influenza Vaccine, 2009, Journal of Virology, vol. 83, No. 18, pp. 9296-9303.*
International Search Report and Written Opinion received for PCT Patent Application No. PCT/IB2014/058501, dated May 27, 2014, 14 pages.
Chen et al., "Partial and Full PCR-Based Reverse Genetics Strategy for Influenza Viruses", PLOS One, vol. 7, No. 9, e46378, Sep. 2012, pp. 1-12.
Fulvini et al., "Gene Constellation of Influenza A Virus Reassortants with High Growth Phenotype Prepared as Seed Candidates for Vaccine Production", PLoS One, vol. 6, No. 6, Jun. 2011, pp. 1-11.
Gibson et al., "Enzymatic Assembly of DNA Molecules up to Several Hundred Kilobases", Nature Methods, vol. 6, 2009, pp. 343-345.
LIS Consult, "Synthetic Biology Newsletter: An LIS Consult and Synthetic Biology Project Initiative", Jun. 2011, pp. 1-22.
Verity et al., "Rapid Generation of Pandemic Influenza Virus Vaccine Candidate Strains Using Synthetic DNA", Influenza and Other Respiratory Viruses, vol. 6, 2012, pp. 101-119.
Wentworth, David E., "Exploiting Synthetic Genomics to Create Influenza Vaccines", J. Craig Venter Institute, Rockville, Maryland, presented at WHO, Dec. 8, 2011, pp. 1-23.

* cited by examiner

*Primary Examiner* — Benjamin P Blumel
(74) *Attorney, Agent, or Firm* — Finnegan, Henderson, Farabow, Garrett & Dunner, LLP

(57) ABSTRACT

Improved methods for the production of reassortant influenza viruses are provided.

33 Claims, 17 Drawing Sheets

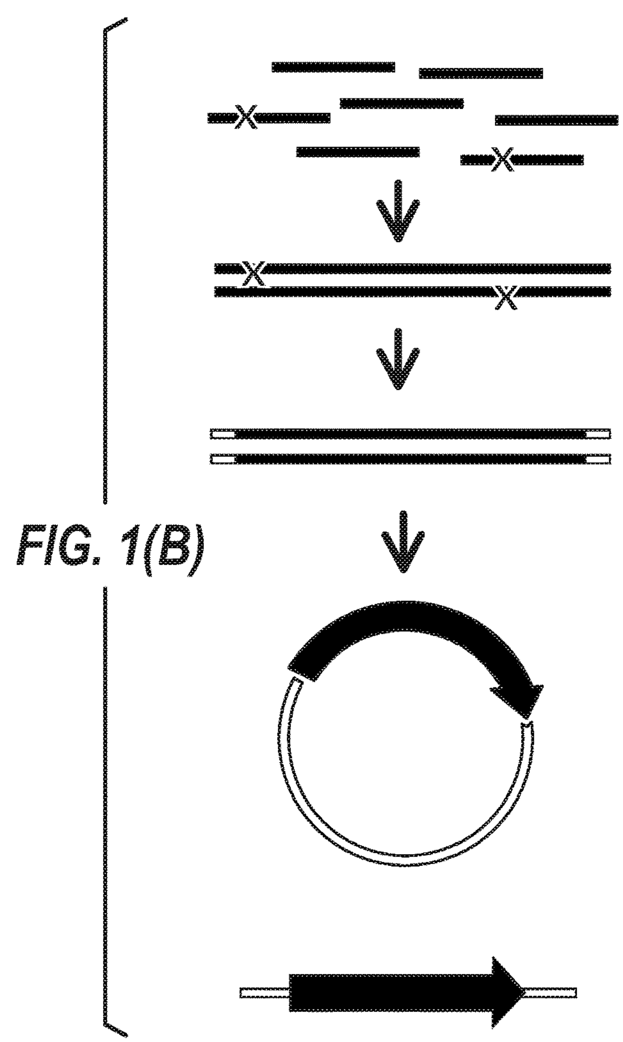
FIG. 1(B)
FIG. 1(C)
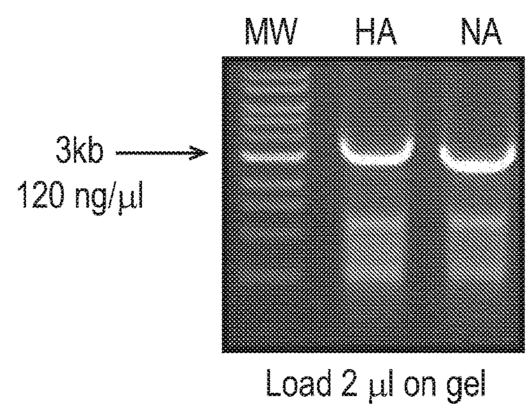

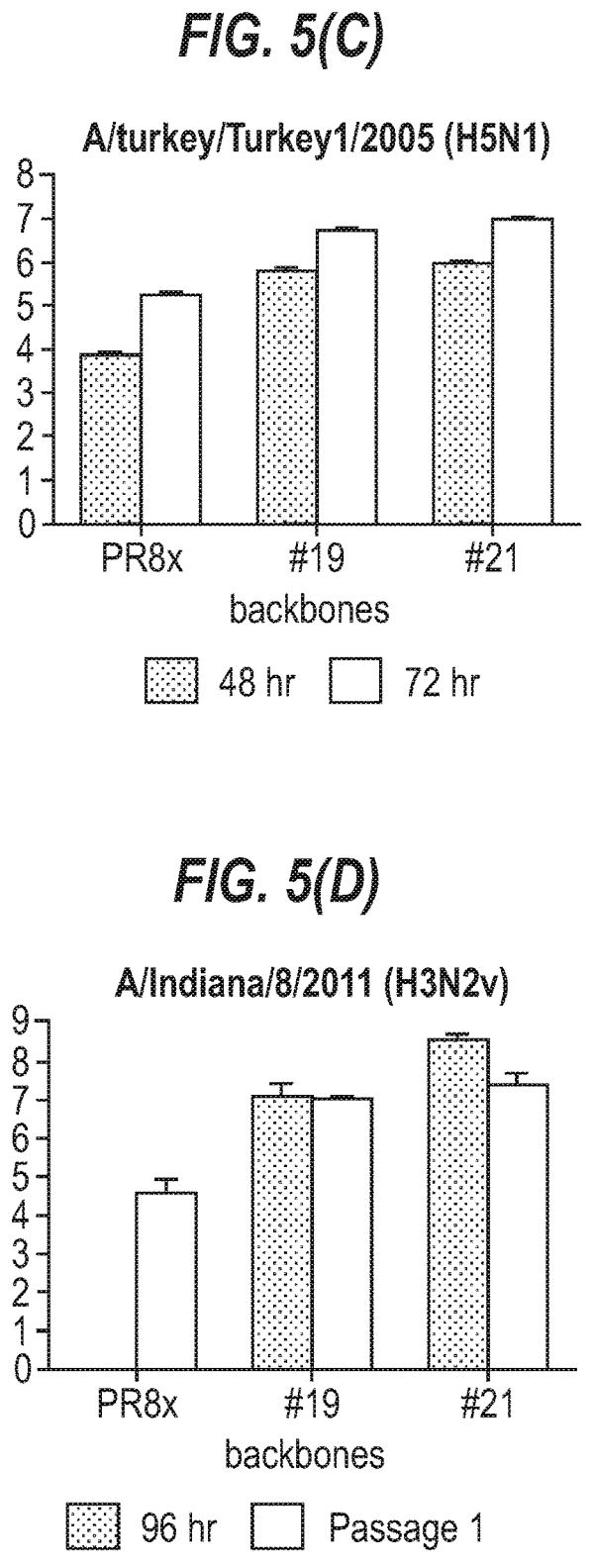

A/turkey/Turkey1/2005 (H5N1)

0 1 2 3 4 5 6 7 8

PR8x #19 #21 backbones 48 hr 72 hr

FIG. 5(D)

A/Indiana/8/2011 (H3N2v)

0 1 2 3 4 5 6 7 8 9

PR8x #19 #21 backbones 96 hr Passage 1

INFLUENZA VIRUS REASSORTMENT

The influenza virus sequence database used for UTR construction and the generation of a library of synthetic gene segments was funded in part by the National Institute of Allergy and Infectious Diseases, National Institutes of Health, Department of Health and Human Services under Contract No. HHSN272200900007C.

CROSS REFERENCE TO RELATED APPLICATIONS

This application is a U.S. National Phase patent application of PCT/IB2014/058501, filed Jan. 23, 2014; which is a continuation of U.S. patent application Ser. No. 13/841,752, filed Mar. 15, 2013, which also claims priority to U.S. Provisional Application No. 61/849,325, filed Jan. 23, 2013; and United Kingdom Application No. 1304827.7, filed Mar. 15, 2013, all of which are herein incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 529552005400SeqList.txt, date recorded: Jun. 18, 2015, size: 333 KB).

STATEMENT OF GOVERNMENT SUPPORT

This invention was supported in part with Government support under BARDA Contract No. HHSO100201000061C awarded by Office of Public Health Emergency Preparedness, Biomedical Advanced Research and Development Authority. The Government has certain rights in the invention.

TECHNICAL FIELD

This invention is in the field of influenza virus reassortment. Furthermore, it relates to manufacturing vaccines for protecting against influenza viruses.

BACKGROUND ART

The 2009 H1N1 influenza pandemic response was the fastest global vaccine development effort in history. Within six months of the pandemic declaration, vaccine companies had developed, produced, and distributed hundreds of millions of doses of licensed pandemic vaccines. Unfortunately, the response was not fast enough as substantial vaccine quantities were available only after the second pandemic wave had peaked. This delay was at least partially due to the late availability of a high-yielding influenza strain which could be used for vaccine production.

One way of obtaining a high-yielding influenza strain is to reassort the circulating vaccine strain with a faster-growing high-yield donor strain. This can be achieved by co-infecting a culture host with the circulating influenza strain and the high-yield donor strain and selecting for reassortant viruses which contain the hemagglutinin (HA) and neuraminidase (NA) segments from the vaccine strain and the other viral segments (i.e. those encoding PB1, PB2, PA, NP, $M_1$, $M_2$, $NS_1$ and $NS_2$) from the donor strain. Another approach is to reassort the influenza viruses by reverse genetics (see, for example references 1 and 2).

As the 2009 experience has shown, the traditional methods for reassorting influenza viruses may not be fast enough to provide sufficient amounts of influenza vaccine during a pandemic. In particular, valuable time is lost in preparing the high-yielding seed virus. There is therefore still a need in the art to provide methods which allow the rapid generation of high-yielding seed viruses in order to further decrease the time it takes between the emergence of an influenza pandemic and the provision of an influenza vaccine. The prior art had suggested solving this problem by preparing HA segments synthetically (see, for example, references 3, 4 and 5). The fastest reported time frame in which the influenza viruses can be prepared using these methods is nine days. Furthermore, these techniques rely on the use of 293T cells which have a high transfection efficacy but which are not approved for vaccine manufacture. There is therefore a need in the art to provide further and improved methods for preparing reassortant influenza viruses.

SUMMARY OF PREFERRED EMBODIMENTS

In some aspects, the invention provides methods which allow a faster preparation of influenza viruses. For example, the invention provides a method of preparing an influenza virus, comprising the steps of (a) preparing one or more expression construct(s) which comprise(s) coding sequences for expressing at least one segment of an influenza virus genome; (b) introducing into a cell which is not 293T one or more expression construct(s) which encode(s) the viral segments of an influenza virus, wherein at least one expression construct is the expression construct prepared in step (a); and (c) culturing the cell in order to produce a reassortant influenza virus from the expression construct(s) introduced in step (b); wherein steps (a) to (c) are performed in a time period of 124 hours or less. The cell is preferably a non-human cell or a human non-kidney cell.

Also provided is a method of preparing an influenza virus comprising the steps of (a) preparing one or more expression construct(s) which comprise(s) coding sequences for expressing at least one segment of an influenza virus genome; (b) introducing into a cell one or more expression construct(s) which encode(s) the viral segments of an influenza virus, wherein at least one expression construct is the expression construct prepared in step (a); and (c) culturing the cell in order to produce a reassortant influenza virus from the expression construct(s) introduced in step (b); wherein steps (a) to (c) are performed in a time period of 100 hours or less.

The invention also provides a method of preparing an influenza virus comprising the steps of (a) providing a synthetic expression construct which comprises coding sequences for expressing at least one segment of an influenza virus genome by (i) synthesising a plurality of overlapping fragments of the synthetic expression construct, wherein the overlapping fragments span the complete synthetic expression construct, and (ii) joining the fragments to provide the synthetic expression construct; (b) introducing into a cell which is not 293T one or more expression construct(s) which encode(s) the viral segments of an influenza virus, wherein at least one expression construct is the synthetic expression construct prepared in step (a); and (c) culturing the cell in order to produce a reassortant influenza virus from the viral segments introduced in step (b); wherein steps (a) to (c) are performed in a time period of 124 hours or less. The cell is preferably a non-human cell or a human non-kidney cell.

The methods may further comprise a step (d) contacting a cell which is of the same cell type as the cell used in step (c) with the virus produced in step (b) to produce further reassortant influenza virus.

The invention also provides a method of preparing an influenza virus, comprising the steps of (a) providing a synthetic expression construct which comprises coding sequences for expressing at least one segment of an influenza virus genome by (i) synthesising a plurality of overlapping fragments of the synthetic expression construct, wherein the overlapping fragments span the complete synthetic expression construct, and (ii) joining the fragments to provide the synthetic expression construct; (b) introducing into a cell one or more expression construct(s) which encode(s) the viral segments of an influenza virus, wherein at least one expression construct is the synthetic expression construct prepared in step (a); (c) culturing the cell in order to produce a reassortant influenza virus from the viral segments introduced in step (b); and (d) contacting a cell which is of the same cell type as the cell used in step (c) with the virus produced in step (c) to produce further reassortant influenza virus; wherein steps (a) to (c) are performed in a time period of 124 hours or less. The cell used is preferably not 293T.

Further provided is a method of preparing an influenza vaccine, comprising the steps of (a) contacting a cell with the reassortant influenza virus prepared by a method according to the invention; (b) culturing the cell in order to produce an influenza virus; and (c) preparing a vaccine from the influenza virus produced in step (b). The cell used in the method is preferably a human non-kidney cell or a non-human cell. Alternatively, or in addition, the cell used in step (a) is of the same cell type as the cell which was used to rescue the influenza virus in the methods discussed in the preceding paragraphs. This is preferred because it facilitates regulatory approval, avoids conflicting culture conditions and avoids the need to retain two different cell types. The cell used is preferably not 293T as this cell is not approved for human vaccine manufacture.

The invention also provides a method of preparing a synthetic expression construct which encodes a viral segment from an influenza virus, comprising: (a) providing the sequence of at least part of the coding region of the HA or NA segment from an influenza virus; (b) identifying the HA and/or NA subtype of the influenza virus from which the coding region is derived; (c) providing a UTR sequence from an influenza virus with the same HA or NA subtype as the subtype identified in step (b); and (d) preparing a synthetic expression construct which encodes a viral segment comprising the coding sequence and the UTR.

The Synthetic Expression Construct

The synthetic expression construct is a DNA molecule which comprises coding sequences for expressing one or more viral RNA segment(s) of an influenza virus genome. The encoded segments can be expressed and then function as viral RNAs which can be packaged into virions to give recombinantly expressed virus. Thus the synthetic expression construct is suitable for producing an influenza virus by reverse genetics, either alone or in combination with other expression constructs.

The synthetic expression construct can be produced by (i) synthesising a plurality of overlapping fragments of the synthetic expression construct, wherein the overlapping fragments span the complete synthetic expression construct, and (ii) joining the fragments to provide the synthetic expression construct.

The method can involve notionally splitting the desired DNA sequence into fragments which can be prepared by a chosen DNA synthesis method e.g. by phosphoramidite chemistry. References 6 and 7 report that the entire 16,299 base pair mouse mitochondrial genome could be synthesized from 600 overlapping 60-base oligonucleotides. The method uses Phusion DNA polymerase (New England Biolabs [NEB]), T5 exonuclease (Epicentre) and Taq DNA ligase (NEB) to join multiple DNA fragments during a brief 50° C. reaction (6). The inventors have discovered that this method can be used to generate synthetic DNA copies of the influenza virus genome and that the resulting method is particularly advantageous because it is rapid and readily automated. Joining the fragments in step (ii) of the methods described above can thus comprise contacting the fragments with a DNA polymerase and a DNA ligase. The method can be practised with any DNA polymerase which can amplify DNA, including Phusion™ DNA polymerase and Taq DNA™ polymerase. Preferably, the methods use a high fidelity DNA polymerase, such as Phusion™ DNA polymerase, PFU™, AccuPrime™ Taq DNA Polymerase, AMPLITAQ™ GOLD DNA pol, T5 DNA polymerase, phi29 DNA polymerase, VENTR™ DNA pol, Deep Vent DNA pol. etc. This is preferred because it decreases the error rate of the resulting DNA molecule. Suitable DNA ligases are also known to the skilled person and include Taq™ DNA ligase, AMPLIGASE thermostable DNA ligase, and Tfi ligase. Reference 8 also discusses suitable ligases which can be used.

Suitable buffers and reaction conditions are described in references 6 and 7 and are also known to the skilled person. The methods can be performed at a temperature between 40° C. and 60° C., for example at a temperature between 45° C. and 55° C. or at a temperature of about 50° C. Preferably, the fragments are incubated with the DNA polymerase and the DNA ligase for a time period of between 15 and 60 minutes.

The synthetic expression constructs may be assembled from fragments with a size of about 30 nucleotides, at least 30 nucleotides, 40-60 nucleotides or at least 61 nucleotides. The fragments may also have a length of less than 40 nucleotides, less than 50 nucleotides, less than 60 nucleotides, less than 100 nucleotides, less than 200 nucleotides, less than 500 nucleotides, less than 1000 nucleotides, less than 5000 nucleotides, or less than 10000 nucleotides. Preferably, the synthetic expression constructs are assembled from fragments with a size of between 61 and 100 nucleotides, for example between 61 and 74 nucleotides. Such fragments are longer than the fragments used in the prior art. For example, references 6 and 7 used fragments with a length of 60 nucleotides. By using longer fragments, the inventors found that the speed for obtaining synthetic expression constructs was increased. This was unexpected as a skilled person would have expected longer fragments to be thermodynamically unfavourable and that it would be harder for overlaps to anneal to each other.

The fragments are synthesised and joined to give the synthetic expression constructs. This can be achieved by performing more than one joining (e.g. ligation) step. For example, some of the DNA fragments may be joined to give longer fragments, and these longer fragments can then be joined again, etc. until the complete synthetic expression construct is eventually prepared. Where the molecule is assembled step-wise in this fashion, the fragments at each stage may be maintained as inserts in vectors e.g. in plasmids or BAC or YAC vectors.

The synthetic expression construct may also be assembled using a single joining step (e.g. a single ligation step) and this is preferred because it allows for a faster assembly of the synthetic expression construct. In these embodiments, fragments which span the entire synthetic expression construct are treated with a joining agent (e.g. a DNA ligase) which assembles the whole synthetic expression construct in a single reaction.

The fragments can be designed to overlap, thereby facilitating the assembly in the correct order and this is preferred when the synthetic expression construct is assembled in a single joining step. It is preferred that the fragments overlap by at least 15 nucleotides, at least 20 nucleotides, at least 40 nucleotides or at least 60 nucleotides. This is preferred because the inventors have found that this increased overlap allowed rapid synthesis of the fragments with high accuracy. Thus the method may involve the synthesis of a plurality of overlapping fragments of the desired synthetic expression construct, such that the overlapping fragments span the complete synthetic expression construct. Both ends of each fragment overlap with a neighbouring 5' or 3' fragment, except for the terminal fragments of a linear molecule where no overlap is required (but if a circular molecule is desired, the two terminal fragments may overlap). Assembly of fragments during the synthetic process can involve in vitro and/or in vivo recombination. For in vitro methods, digestion with a 3' exonuclease can be used to expose overhangs at the terminus of a fragment, and complementary overhangs in overlapping fragments can then be annealed, followed by joint repair ("chewback assembly"). For in vivo methods, overlapping clones can be assembled using e.g. the TAR cloning method disclosed in reference 9. For fragments <100 kbp (e.g. easily enough to encode all segments of an influenza virus genome) it is readily possible to rely solely on in vitro recombination methods.

Other synthetic methods may be used. For instance, reference 10 discloses a method in which fragments of about 5 kbp are synthesised and then assembled into longer sequences by conventional cloning methods. Unpurified 40 base synthetic oligonucleotides are built into 500-800 bp synthons by automated PCR-based gene synthesis, and these synthons joined into multisynthon 5 kbp segments using a small number of endonucleases and "ligation by selection." These large segments can subsequently be assembled into longer sequences by conventional cloning. This method can readily provide a 32 kbp DNA molecule, which is easily enough to encode a complete influenza virus. Similarly, reference 11 discloses a method where a 32 kb molecule was assembled from seven DNA fragments which spanned the complete sequence. The ends of the seven DNAs were engineered with unique junctions, thereby permitting assembly only of adjacent fragments. The interconnecting restriction site junctions at the ends of each DNA are systematically removed after assembly.

Following the assembly of the synthetic expression construct, it is possible to amplify the whole or part of the synthetic expression construct. Methods for DNA amplification are known in the art and include, for example, polymerase chain reaction (PCR). Where only part of the synthetic expression construct is amplified it is preferred to amplify the part of the expression construct which encodes the one or more viral segments.

One drawback of the reference 6 method is that only 3% of the synthetic products have the correct sequence. In the prior art this problem was solved by cloning and sequencing subassemblies, and sets of error-free sequences were selected for subsequent rounds of assembly. Whilst this addresses the problem of errors in the resulting DNA molecule, the method is time-consuming and thus not suitable for use in a method which requires high speed and accuracy. The inventors have thus addressed the problem of error correction differently. In particular, they have discovered that the error rate can be decreased significantly by including an alternative error correction step. The invention thus provides a method of preparing a synthetic expression construct, comprising the steps of (i) synthesising a plurality of overlapping fragments of the synthetic expression construct, wherein the overlapping fragments span the complete synthetic expression construct, (ii) joining the fragments to provide a DNA molecule; (iii) melting the DNA molecule; (iv) re-annealing the DNA in the presence of an agent which excises mismatched nucleotides from the DNA molecule; and (v) amplifying the DNA to produce the synthetic expression construct. By including this additional step, the inventors were able to obtain full-length sequences in which 80-100% had the correct sequence. The DNA in step (v) can be amplified using DNA polymerases, preferably high-fidelity DNA polymerases, as known in the art and described above.

Suitable conditions for melting (i.e. dissociating the DNA double helix into single strands) and re-annealing DNA are known in the art. For example, the DNA can be melted by heating it to a temperature of at least 90° C. Likewise, the DNA can be re-annealed by reducing the temperature. The agent used to excise mismatched nucleotides is usually an enzyme such as, for example, the Res 1 enzyme (which is available in the ErrASE™ error correction kit (Novici Biotech)), Cel I, T7 endonuclease I, S1 nuclease, T7 endonuclease, *E. coli* endo. V, Mung Bean endo., etc.

A synthetic expression construct may include one or more "watermark" sequences. These are sequences which can be used to identify or encode information in the DNA. It can be in either noncoding or coding sequences. Most commonly, it encodes information within coding sequences without altering the amino acid sequences. For DNAs encoding segmented RNA viral genomes, any watermark sequences are ideally included in intergenic sites because synonymous codon changes may have substantial biological effects for encoded RNA segments.

The synthetic expression construct may be linear (14) or circular. Circular synthetic expression constructs can be made by circularising linear constructs and vice versa. Methods for such circularisation are described in ref. 14. Linearisation of a circular molecule can be achieved in various easy ways e.g. by utilising one or more restriction enzyme(s), or by amplification from a template (including a circular template) using a nucleic acid amplification technique (e.g. by PCR).

Where the synthetic expression construct is circular, it is possible to contact the DNA following step (ii) with an agent (for example an enzyme) that degrades linear DNA. This has the advantage that linear synthetic expression constructs are selectively removed, thus selecting for the circular product. Suitable agents are known in the art and include, for example, T5 exonuclease, lambda exonuclease, and exonuclease III.

The synthetic expression construct may be incorporated into a vector, such as a plasmid or other episomal construct, using conventional techniques known in the art. The 3' and/or 5' terminal fragment of the synthetic expression construct may comprise an overhang which is complementary to an overhang on the vector, which facilitates the cloning of the synthetic expression construct (such that, for example, the synthetic expression construct may be cloned into an overhang created by a restriction enzyme). The vector may provide the regulatory sequences which are necessary to express the viral RNA segments from the DNA construct (e.g. RNA pol I promoter, RNA pol II promoter; RNA polymerase I transcription termination sequence, RNA polymerase II transcription termination sequence etc.). This can be advantageous because these sequences do then not need to be included in the synthetic expression construct. It is also possible to clone a synthetic expression construct without regulatory sequences into a vector that provides these sequences and subsequently amplifying a linear synthetic expression construct which comprises the original synthetic expression construct in conjunction with the regulatory sequences so that the resulting synthetic expression construct can then be used to express the viral segments.

Expression Constructs

The invention produces influenza viruses through reverse genetics techniques. In these techniques, the viruses may be produced in culture hosts using a synthetic expression construct which comprises coding sequences for expressing at least one segment of an influenza virus genome, as described in the preceding sections. The synthetic expression construct can drive expression in a eukaryotic cell of viral segments encoded therein. The expressed viral segment RNA can be translated into a viral protein that can be incorporated into a virion.

The term "synthetic expression construct" refers to an expression construct which has been prepared synthetically as described in the preceding sections, or which is derived from an expression construct prepared in this manner (for example by DNA amplification). It also encompasses vectors which comprise such an expression construct. The term "expression construct" encompasses both synthetic expression construct as well as expression constructs which were not prepared synthetically.

The synthetic expression construct may encode all the viral segments which are necessary to produce an influenza virus. Alternatively, it may encode one, two, three, four, five, six, or seven viral segments. Where the synthetic expression construct does not encode all the viral segments which are necessary to produce an influenza virus, the remaining viral segments are provided by one or more further expression construct(s). These one or more further expression constructs may also be synthetic expression constructs or they may be expression constructs which have been generated using alternative methods such as, for example, the methods described in reference 12.

Where the synthetic expression construct does not encode all the viral segments which are necessary to produce an influenza virus, the synthetic expression construct may encode the neuraminidase (NA) and/or hemagglutinin (HA) segments and the remaining vRNA encoding segments, excluding the HA and/or NA segment(s), are included on a different expression construct. This has the advantage that only the expression construct comprising the HA and/or NA segments needs to be replaced when a new influenza vaccine strain emerges (e.g. a new pandemic influenza virus or a new seasonal influenza virus).

The expression constructs may be uni-directional or bi-directional expression constructs. Where a host cell expresses more than one transgene (whether on the same or different expression constructs) it is possible to use uni-directional and/or bi-directional expression.

Bi-directional expression constructs contain at least two promoters which drive expression in different directions (i.e. both 5' to 3' and 3' to 5') from the same construct. The two promoters can be operably linked to different strands of the same double stranded DNA. Preferably, one of the promoters is a pol I promoter and at least one of the other promoters is a pol II promoter. This is useful as the pol I promoter can be used to express uncapped vRNAs while the pol II promoter can be used to transcribe mRNAs which can subsequently be translated into proteins, thus allowing simultaneous expression of RNA and protein from the same construct.

The pol I and pol II promoters used in the expression constructs may be endogenous to an organism from the same taxonomic order from which the host cell is derived. Alternatively, the promoters can be derived from an organism in a different taxonomic order than the host cell. The term "order" refers to conventional taxonomic ranking, and examples of orders are primates, rodentia, carnivora, marsupialia, cetacean, etc. Humans and chimpanzees are in the same taxonomic order (primates), but humans and dogs are in different orders (primates vs. carnivora). For example, the human pol I promoter can be used to express viral segments in canine cells (e.g. MDCK cells) [13]. Where more than one expression construct is used within an expression system, the promoters may be a mixture of endogenous and non-endogenous promoters.

The expression construct will typically include an RNA transcription termination sequence. The termination sequence may be an endogenous termination sequence or a termination sequence which is not endogenous to the host cell. Suitable termination sequences will be evident to those of skill in the art and include, but are not limited to, RNA polymerase I transcription termination sequence, RNA polymerase II transcription termination sequence, and ribozymes. Furthermore, the expression constructs may contain one or more polyadenylation signals for mRNAs, particularly at the end of a gene whose expression is controlled by a pol II promoter.

An expression construct may be a vector, such as a plasmid or other episomal construct. Such vectors will typically comprise at least one bacterial and/or eukaryotic origin of replication. Furthermore, the vector may comprise a selectable marker which allows for selection in prokaryotic and/or eukaryotic cells. Examples of such selectable markers are genes conferring resistance to antibiotics, such as ampicillin or kanamycin. The vector may further comprise one or more multiple cloning sites to facilitate cloning of a DNA sequence.

As an alternative, an expression construct may be a linear expression construct. Such linear expression constructs will typically not contain any amplification and/or selection sequences. However, linear constructs comprising such amplification and/or selection sequences are also within the scope of the present invention. An example of a method using such linear expression constructs for the expression of influenza virus is described in reference 14.

Where the expression construct is a linear expression construct, it is possible to linearise it before introduction into the host cell utilising a single restriction enzyme site. Alternatively, it is possible to excise the expression construct from a vector using at least two restriction enzyme sites. Furthermore, it is also possible to obtain a linear expression construct by amplifying it using a nucleic acid amplification technique (e.g. by PCR).

Where the expression construct is not a synthetic expression construct, it may be generated using methods known in the art. Such methods were described, for example, in reference 15.

The expression constructs of the invention can be introduced into host cells using any technique known to those of skill in the art. For example, expression constructs of the invention can be introduced into host cells by employing electroporation, DEAE-dextran, calcium phosphate precipitation, liposomes, microinjection, or microparticle-bombardment. Once transfected, the host cell will recognise genetic elements in the construct and will begin to express the encoded viral RNA segments.

The expression construct(s) can be introduced into the same cell type which is subsequently used for the propagation of the influenza viruses. Alternatively, the cells into which the expression constructs are introduced and the cells used for propagation of the influenza viruses may be different. In some embodiments, cells may be added following the introduction of the expression construct(s) into the cell, as described in reference 16. This is particularly preferred because it increases the rescue efficiency of the viruses further and can thus help to reduce the time required for viral rescue. The cells which are added may be of the same or a different cell type as the cell into which the expression construct(a) is/are introduced, but it is preferred to use cells of the same cell type as this facilitates regulatory approval and avoids conflicting culture conditions.

Where the expression host is a canine cell, such as a MDCK cell line, protein-coding regions may be optimised for canine expression e.g. using a promoter from a wild-type canine gene or from a canine virus, and/or having codon usage more suitable for canine cells than for human cells. For instance, whereas human genes slightly favour UUC as the codon for Phe (54%), in canine cells the preference is stronger (59%). Similarly, whereas there is no majority preference for Ile codons in human cells, 53% of canine codons use AUC for Ile. Canine viruses, such as canine parvovirus (a ssDNA virus) can also provide guidance for codon optimisation e.g. 95% of Phe codons in canine parvovirus sequences are UUU (vs. 41% in the canine genome), 68% of Ile codons are AUU (vs. 32%), 46% of Val codons are GUU (vs. 14%), 72% of Pro codons are CCA (vs. 25%), 87% of Tyr codons are UAU (vs. 40%), 87% of His codons are CAU (vs. 39%), 92% of Gln codons are CAA (vs. 25%), 81% of Glu codons are GAA (vs. 40%), 94% of Cys codons are UGU (vs. 42%), only 1% of Ser codons are UCU (vs. 24%), CCC is never used for Phe and UAG is never used as a stop codon. Thus protein-coding genes can be made more like genes which nature has already optimised for expression in canine cells, thereby facilitating expression.

Reverse Genetics

Reverse genetics for influenza viruses can be practised with 12 expression constructs to express the four proteins required to initiate replication and transcription (PB1, PB2, PA and NP) and all eight viral genome segments. To reduce the number of expression constructs, however, a plurality of RNA polymerase I transcription cassettes (for viral RNA synthesis) can be included on a single expression construct (e.g. sequences encoding 1, 2, 3, 4, 5, 6, 7 or all 8 influenza vRNA segments), and a plurality of protein-coding regions with RNA polymerase II promoters on another expression construct (e.g. sequences encoding 1, 2, 3, 4, 5, 6, 7 or 8 influenza mRNA transcripts) [17]. It is also possible to include one or more influenza vRNA segments under control of a pol I promoter and one or more influenza protein coding regions under control of another promoter, in particular a pol II promoter, on the same expression construct. This is preferably done by using bi-directional expression constructs.

Known reverse genetics systems involve expressing viral RNA (vRNA) molecules from pol I promoters, bacterial RNA polymerase promoters, bacteriophage polymerase promoters, etc. As influenza viruses require the presence of viral polymerase to initiate the life cycle, systems may also provide these proteins e.g. the system further comprises expression constructs that encode viral polymerase proteins such that expression of both types of DNA leads to assembly of a complete infectious virus. It is also possible to supply the viral polymerase as a protein.

Where reverse genetics is used for the expression of influenza vRNA, it will be evident to the person skilled in the art that precise spacing of the sequence elements with reference to each other is important for the polymerase to initiate replication. It is therefore important that the sequence encoding the viral RNA is positioned correctly between the pol I promoter and the termination sequence, but this positioning is well within the capabilities of those who work with reverse genetics systems.

In order to produce a recombinant virus, a cell must express all segments of the viral genome which are necessary to assemble a virion. The expression constructs preferably provide all of the viral RNA and proteins, but it is also possible to use a helper virus to provide some of the RNA and proteins, although systems which do not use a helper virus are preferred.

In some embodiments an expression construct will also be included which leads to expression of an accessory protein in the host cell. For instance, it can be advantageous to express a non-viral serine protease (e.g. trypsin) as part of a reverse genetics system.

Viral Segments

The synthetic expression construct encodes one or more viral segments. During the early days of an influenza pandemic it is not unusual to have sequences of the circulating strains available which include only the complete coding region but incomplete untranslated regions (UTRs). Awaiting the complete segment sequence (including the coding region and the UTRs) before commencing production of viruses costs time and delays the provision of the vaccines. The inventors have provided an improved method for preparing a synthetic expression construct encoding a viral segment, which method reduces the time required to obtain the viral segment. The method comprises the steps of: (a) providing the sequence of at least part of the coding region of the HA or NA segment from an influenza virus; (b) identifying the HA and/or NA subtype of the virus from which the coding region is derived; (c) providing a UTR sequence from an influenza virus with the same HA or NA subtype as the subtype identified in step (b); and (d) preparing a synthetic expression construct which encodes a viral segment comprising the coding sequence and the UTR.

The sequence of the coding region of the viral segment can be provided by sequencing the circulating strain. The sequence may also be obtained from other sources such as, for example, a health care authority. Preferably, the whole coding region is used in the method as this will facilitate the determination of the HA or NA subtype of the virus from which the coding region is derived. It is also possible to use at least part of the coding region provided the coding region is complete enough to allow the determination of the HA or NA subtype. This will generally be the case where a fragment covering at least 90%, at least 95%, or at least 99% of the full-length coding region is available. The viral segment used in the analysis is preferably the HA or NA segment.

The HA and/or NA subtype of the virus from which the coding sequence is derived can be determined using standard methods in the art. For example, the sequence of the coding region can be aligned to the sequences of coding regions from viruses with known HA and/or NA subtypes. The coding regions which are aligned need, of course, be the coding region of the same viral segment (e.g. the HA or NA segment). Influenza viral segments from viruses with the same HA and/or NA subtype will show the highest sequence identity between the sequences. Suitable programs for performing the analysis are known in the art and include BLAST™.

In order to provide a suitable UTR for the viral segment, the UTR of the viral strain which showed the highest sequence identity in step (a) can be used. Alternatively, the UTR can be identified by determining the consensus sequences of UTRs from viral strains with the same HA or NA subtype. This can be achieved by aligning two or more influenza strains with the same HA or NA subtype and determining the conserved residues in the UTRs. For example, the consensus sequence may be determined by aligning the UTRs from 2, 5, 10, 15, 20, 30 or more influenza strains with the same HA or NA subtype. The consensus UTR sequence can then be used to prepare the complete DNA molecule. Suitable programs for aligning multiple sequences are known in the art and include ClustalW2™.

Where the DNA molecules are prepared using a consensus UTR sequence, it is not necessary to determine this consensus sequence every time. Instead, the analysis can be performed for influenza virus strains with various HA and NA subtypes and the resulting UTRs for each HA and NA subtype can be kept in a database. Once the HA or NA subtype of the circulating strain has been determined it is then necessary only to choose the UTR of an influenza strain with the same HA or NA subtype from the database.

The DNA molecule comprising the coding sequence and the identified UTRs can be prepared by any of the methods described herein.

The Culture Host

The influenza viruses are typically produced using a cell line, although primary cells may be used as an alternative. The cell will typically be mammalian, although avian or insect cells can also be used. Suitable mammalian cells include, but are not limited to, human, hamster, cattle, primate and dog cells. In some embodiments, the cell is a human non-kidney cell or a non-human cell. Various cells may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [18-20]. Suitable dog cells are e.g. kidney cells, as in the CLDK and MDCK cell lines. Suitable avian cells include the EBx cell line derived from chicken embryonic stem cells, EB45, EB14, and EB14-074 [21].

Further suitable cells include, but are not limited to: CHO; MRC 5; PER.C6 [22]; FRhL2; WI-38; etc. Suitable cells are widely available e.g. from the American Type Cell Culture (ATCC) collection [23], from the Coriell Cell Repositories [24], or from the European Collection of Cell Cultures (ECACC). For example, the ATCC supplies various different Vero cells under catalogue numbers CCL 81, CCL 81.2, CRL 1586 and CRL-1587, and it supplies MDCK cells under catalogue number CCL 34. PER.C6 is available from the ECACC under deposit number 96022940.

Preferred cells for use in the invention are MDCK cells [25-27], derived from Madin Darby canine kidney. The original MDCK cells are available from the ATCC as CCL 34. It is preferred that derivatives of these or other MDCK cells are used. Such derivatives were described, for instance, in reference 25 which discloses MDCK cells that were adapted for growth in suspension culture ('MDCK 33016' or '33016-PF', deposited as DSM ACC 2219). Furthermore, reference 28 discloses MDCK-derived cells that grow in suspension in serum free culture ('B-702', deposited as FERM BP-7449). In some embodiments, the MDCK cell line used may be tumorigenic, but it is also envisioned to use non-tumorigenic MDCK cells. For example, reference 29 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (ATCC PTA-6503). Reference 30 discloses MDCK cells with high susceptibility to infection, including 'MDCK.5F1' cells (ATCC CRL 12042).

It is possible to use a mixture of more than one cell type in the methods of the invention, but it is preferred to use a single cell type e.g. using monoclonal cells. Where a mixture of cells is used, it is preferred that the mixture does not contain 293T cells as these cells are not approved for vaccine manufacture.

The cells used in the methods of the invention are preferably cells which are suitable for producing an influenza vaccine that can be used for administration to humans. Such cells must be derived from a cell bank system which is approved for vaccine manufacture and registered with a national control authority, and must be within the maximum number of passages permitted for vaccine production (see reference 31 for a summary). Examples of suitable cells which have been approved for vaccine manufacture include MDCK cells (like MDCK 33016; see reference 25), CHO cells, Vero cells, and PER.C6 cells. The methods of the invention preferably do not use 293T cells as these cells are not approved for vaccine manufacture.

Preferably, the cells used for preparing the virus and for preparing the vaccine are of the same cell type. For example, the cells may both be MDCK, Vero or PerC6 cells. This is preferred because it facilitates regulatory approval as approval needs to be obtained only for a single cell line. It also has the further advantage that competing culture selection pressures or different cell culture conditions can be avoided. The methods of the invention may also use the same cell line throughout, for example MDCK 33016.

The influenza viruses prepared according to the methods of the invention may subsequently be propagated in eggs. The current standard method for influenza virus growth for vaccines uses embryonated SPF hen eggs, with virus being purified from the egg contents (allantoic fluid). It is also possible to passage a virus through eggs and subsequently propagate it in cell culture and vice versa.

Preferably, the cells are cultured in the absence of serum, to avoid a common source of contaminants. Various serum-free media for eukaryotic cell culture are known to the person skilled in the art e.g. Iscove's medium, ultra CHO medium (BioWhittaker), EX-CELL (JRH Biosciences). Furthermore, protein-free media may be used e.g. PF-CHO (JRH Biosciences). Otherwise, the cells for replication can also be cultured in the customary serum-containing media (e.g. MEM or DMEM medium with 0.5% to 10% of fetal calf serum).

The cells may be in adherent culture or in suspension.

Reassortant Viruses

The reassortant influenza strains produced by the methods of the invention contain viral segments from a vaccine strain and one or more donor strain(s). The vaccine strain is the influenza strain which provides the HA segment of the reassortant influenza strain. The vaccine strain can be any strain and can vary from season to season.

A donor strain is an influenza strain which provides one or more of the backbone segments (i.e. those encoding PB1, PB2, PA, NP, $M_1$, $M_2$, $NS_1$ and $NS_2$) of the influenza strain. The NA segment may also be provided by a donor strain or it may be provided by the vaccine strain. The reassortant influenza strains of the invention may also comprise one or more, but not all, of the backbone segments from the vaccine strain. As the reassortant influenza virus contains a total of eight segments, it will therefore contain x (wherein x is from 1-7) viral segments from the vaccine strain and 8-x viral segments from the one or more donor strain(s).

The reassortant influenza virus strains may grow to higher or similar viral titres in cell culture and/or in eggs in the same time (for example 12 hours, 24 hours, 48 hours or 72 hours) and under the same growth conditions compared to the wild-type vaccine strain. In particular, they can grow to higher or similar viral titres in MDCK cells (such as MDCK 33016) in the same time and under the same growth conditions compared to the wild-type vaccine strain. The viral titre can be determined by standard methods known to those of skill in the art. Usefully, the reassortant viruses of the invention may achieve a viral titre which is at least 5% higher, at least 10% higher, at least 20% higher, at least 50% higher, at least 100% higher, at least 200% higher, or at least 500% higher than the viral titre of the wild-type vaccine strain in the same time frame and under the same conditions. The reassortant influenza viruses may also grow to similar viral titres in the same time and under the same growth conditions compared to the wild-type vaccine strain. A similar titre in this context means that the reassortant influenza viruses grow to a titre which is within 3% of the viral titre achieved with the wild-type vaccine strain in the same time and under the same growth conditions (i.e. wild-type titre±3%).

The reassortant viruses of the invention can contain the backbone segments from two or more donor strains, or at least one (i.e. one, two, three, four, five or six) backbone viral segment from a donor strain as described herein. The backbone viral segments are those which do not encode HA or NA. Thus, backbone segments will typically encode the PB1, PB2, PA, NP, $M_1$, $M_2$, $NS_1$ and $NS_2$ polypeptides of the influenza virus.

When the reassortant viruses of the invention are reassortants comprising the backbone segments from a single donor strain, the reassortant viruses will generally include segments from the donor strain and the vaccine strain in a ratio of 1:7, 2:6, 3:5, 4:4, 5:3, 6:2 or 7:1. Having a majority of segments from the donor strain, in particular a ratio of 6:2, is typical. When the reassortant viruses comprise backbone segments from two donor strains, the reassortant virus will generally include segments from the first donor strain, the seconds donor strain and the vaccine strain in a ratio of 1:1:6, 1:2:5, 1:3:4, 1:4:3, 1:5:2, 1:6:1, 2:1:5, 2:2:4, 2:3:3, 2:4:2, 2:5:1, 3:1:2, 3:2:1, 4:1:3, 4:2:2, 4:3:1, 5:1:2, 5:2:1 or 6:1:1. The reassortant influenza viruses may also comprise viral segments from more than two, for example from three, four, five or six donor strains.

Where the reassortant influenza virus comprises backbone segments from two or three donor strains, each donor strain may provide more than one of the backbone segments of the reassortant influenza virus, but one or two of the donor strains can also provide only a single backbone segment.

Where the reassortant influenza virus comprises backbone segments from two, three, four or five donor strains, one or two of the donor strains may provide more than one of the backbone segments of the reassortant influenza virus. In general the reassortant influenza virus cannot comprise more than six backbone segments. Accordingly, for example, if one of the donor strains provides five of the viral segments, the reassortant influenza virus can only comprise backbone segments from a total of two different donor strains.

In general a reassortant influenza virus will contain only one of each backbone segment. For example, when the influenza virus comprises the NP segment from B/Brisbane/60/08 it will not at the same time comprise the NP segment from another influenza strain.

Strains which can be used as vaccine strains include strains which are resistant to antiviral therapy (e.g. resistant to oseltamivir [32] and/or zanamivir), including resistant pandemic strains [33].

The reassortant influenza strains produced by the methods of the invention may comprise segments from a vaccine strain which is an inter-pandemic (seasonal) influenza vaccine strain. It may also comprise segments from a vaccine strain which is a pandemic strain or a potentially pandemic strain. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. A vaccine strain with H5 hemagglutinin type is preferred where the reassortant virus is used in vaccines for immunizing against pandemic influenza, such as a H5N1 strain. Other possible strains include H5N3, H9N2, H2N2, H7N1 and H7N7, and any other emerging potentially pandemic strains. The invention is particularly suitable for producing reassortant viruses for use in vaccine for protecting against potential pandemic virus strains that can or have spread from a non-human animal population to humans, for example a swine-origin H1N1 influenza strain.

The methods of the invention can be used to prepare reassortant influenza A strains and reassortant influenza B strains.

Reassortant Influenza A Viruses

Where the methods are used to prepare reassortant influenza A strains, the strains may contain the influenza A virus HA subtypes H1, H2, H3, H4, H5, H6, H7, H8, H9, H10, H11, H12, H13, H14, H15, H16 or H17. They may contain the influenza A virus NA subtypes N1, N2, N3, N4, N5, N6, N7, N8 or N9. Where the vaccine strain is a seasonal influenza strain, it may have a H1 or H3 subtype. In one aspect of the invention the vaccine strain is a H1N1 or H3N2 strain.

The reassortant influenza A viruses preferably comprise at least one backbone viral segment from the donor strain PR8-X. Thus, the influenza viruses of the invention may comprise one or more genome segments selected from: a PA segment having at least 95%, at least 96%, at least 97%, at least 98%, at least 99% or 100% identity to the sequence of SEQ ID NO: 9, a PB1 segment having at least 95%, at least 96%, at least 97%, at least 98%, at least 99% or 100% identity to the sequence of SEQ ID NO: 10, a PB2 segment having at least 95%, at least 96%, at least 97%, at least 98%, at least 99% or 100% identity to the sequence of SEQ ID NO: 11, a M segment having at least 95%, at least 96%, at least 97%, at least 98%, at least 99% or 100% identity to the sequence of SEQ ID NO: 13, a NP segment having at least 95%, at least 96%, at least 97%, at least 98%, at least 99% or 100% identity to the sequence of SEQ ID NO: 12, and/or a NS segment having at least 95%, at least 96%, at least 97%, at least 98%, at least 99% or 100% identity to the sequence of SEQ ID NO: 14. The reassortant influenza A virus may comprise all of these backbone segments.

Alternatively, or in addition, the reassortant influenza A virus may comprise one or more backbone viral segments from the 105p30 strain. Thus, where the reassortant influenza A virus comprises one or more genome segments from the 105p30 strain, the viral segments may have sequences selected from: a PA segment having at least 95%, at least 96%, at least 97%, at least 98%, at least 99% or 100% identity to the sequence of SEQ ID NO: 42, a PB1 segment having at least 95%, at least 96%, at least 97%, at least 98%, at least 99% or 100% identity to the sequence of SEQ ID NO: 43, a PB2 segment having at least 95%, at least 96%, at least 97%, at least 98%, at least 99% or 100% identity to the sequence of SEQ ID NO: 44, a M segment having at least 95%, at least 96%, at least 97%, at least 98%, at least 99% or 100% identity to the sequence of SEQ ID NO: 46, a NP segment having at least 95%, at least 96%, at least 97%, at least 98%, at least 99% or 100% identity to the sequence of SEQ ID NO: 45, and/or a NS segment having at least 95%, at least 96%, at least 97%, at least 98%, at least 99% or 100% identity to the sequence of SEQ ID NO: 47. The reassortant influenza A virus may comprise all of these backbone segments.

The reassortant influenza viruses may comprise backbone segments from two or more influenza donor strains. The inventors have found that such reassortant influenza A viruses grow particularly well in culture hosts. For example, the inventors have found that a reassortant influenza A virus comprising the NP, PB1 and PB2 segments from 105p30 and the M, NS and PA segments from PR8-X provided a higher rescue efficiency and grew faster compared to reassortant influenza A viruses which comprise all backbone segments from PR8-X. Likewise, a reassortant influenza A strain comprising the PB1 segment from A/California/4/09 and the other backbone segments from PR8-X often had greater rescue efficiencies and HA yields than reassortant influenza A viruses which comprise all backbone segments from PR8-X. Such reassortant influenza A viruses are particularly suitable for use in the methods of the invention because the increased rescue efficiency increases the speed further by which seed viruses for vaccine manufacture can be obtained.

Reassortant influenza A viruses with backbone segments from two or more influenza donor strains may comprise the HA segment and the PB1 segment from different influenza A strains. In these reassortant influenza viruses the PB1 segment may be from donor viruses with the same influenza virus HA subtype as the vaccine strain. For example, the PB1 segment and the HA segment may both be from influenza viruses with a H1 subtype. The reassortant influenza A viruses may also comprise the HA segment and the PB1 segment from different influenza A strains with different influenza virus HA subtypes, wherein the PB1 segment is not from an influenza virus with a H3 HA subtype and/or wherein the HA segment is not from an influenza virus with a H1 or H5 HA subtype. For example, the PB1 segment may be from a H1 virus and/or the HA segment may be from a H3 influenza virus. Where the reassortants contain viral segments from more than one influenza donor strain, the further donor strain(s) can be any donor strain. For example, some of the viral segments may be derived from the A/Puerto Rico/8/34 or A/Ann Arbor/6/60 influenza strains. Reassortants containing viral segments from the A/Ann Arbor/6/60 strain may be advantageous, for example, where the reassortant virus is to be used in a live attenuated influenza vaccine.

The reassortant influenza A virus may also comprise backbone segments from two or more influenza donor strains, wherein the PB1 segment is from the A/California/07/09 influenza strain. This segment may have at least 95% identity, at least 96% identity, at least 97% identity, at least 98% identity, at least 99% identity or 100% identity with the sequence of SEQ ID NO: 24. The reassortant influenza A virus may have the H1 HA subtype. It will be understood that a reassortant influenza virus according to this aspect of the invention will not comprise the HA and/or NA segments from A/California/07/09.

The reassortant influenza strains may comprise the HA segment and/or the NA segment from an A/California/4/09 strain. Thus, for instance, the HA gene segment may encode a H1 hemagglutinin which is more closely related to SEQ ID NO: 70 than to SEQ ID NO: 50 (i.e. has a higher degree sequence identity when compared to SEQ ID NO: 70 than to SEQ ID NO: 50 using the same algorithm and parameters). SEQ ID NOs: 70 and 50 are 80% identical. Similarly, the NA gene may encode a N1 neuraminidase which is more closely related to SEQ ID NO: 99 than to SEQ ID NO: 51. SEQ ID NOs: 99 and 51 are 82% identical.

The reassortant influenza A virus may also comprise at least one backbone viral segment from the A/California/07/09 influenza strain. When the at least one backbone viral segment is the PA segment it may have a sequence having at least 95%, at least 96%, at least 97% or at least 99% identity with the sequence of SEQ ID NO: 23. When the at least one backbone viral segment is the PB1 segment, it may have a sequence having at least 95%, at least 96%, at least 97% or at least 99% identity with the sequence of SEQ ID NO: 24. When the at least one backbone viral segment is the PB2 segment, it may have a sequence having at least 95%, at least 96%, at least 97% or at least 99% identity with the sequence of SEQ ID NO: 25. When the at least one backbone viral segment is the NP segment it may have a sequence having at least 95%, at least 96%, at least 97% or at least 99% identity with the sequence of SEQ ID NO: 26. When the at least one backbone viral segment is the M segment it may have a sequence having at least 95%, at least 96%, at least 97% or at least 99% identity with the sequence of SEQ ID NO: 27. When the at least one backbone viral segment is the NS segment it may have a sequence having at least 95%, at least 96%, at least 97% or at least 99% identity with the sequence of SEQ ID NO: 28.

Where a reassortant influenza A virus comprises the PB1 segment from A/Texas/1/77, it preferably does not comprise the PA, NP or M segment from A/Puerto Rico/8/34. Where a reassortant influenza A virus comprises the PA, NP or M segment from A/Puerto Rico/8/34, it preferably does not comprise the PB1 segment from A/Texas/1/77. In some embodiments, the invention does not encompass reassortant influenza A viruses which have the PB1 segment from A/Texas/1/77 and the PA, NP and M segments from A/Puerto Rico/8/34. The PB1 protein from A/Texas/1/77 may have the sequence of SEQ ID NO: 29 and the PA, NP or M proteins from A/Puerto Rico/8/34 may have the sequence of SEQ ID NOs 30, 31 or 32, respectively.

The backbone viral segments may be optimized for culture in the specific culture host. For example, where the reassortant influenza viruses are cultured in mammalian cells, it is advantageous to adapt at least one of the viral segments for optimal growth in the culture host. For example, where the expression host is a canine cell, such as a MDCK cell line, the viral segments may have a sequence which optimises viral growth in the cell. Thus, the reassortant influenza viruses of the invention may comprise a PB2 genome segment which has lysine in the position corresponding to amino acid 389 of SEQ ID NO: 3 when aligned to SEQ ID NO: 3 using a pairwise alignment algorithm, and/or asparagine in the position corresponding to amino acid 559 of SEQ ID NO: 3 when aligned to SEQ ID NO: 3 using a pairwise alignment algorithm. Also provided are reassortant influenza viruses in accordance with the invention in which the PA genome segment has lysine in the position corresponding to amino acid 327 of SEQ ID NO: 1 when aligned to SEQ ID NO: 1 using a pairwise alignment algorithm, and/or aspartic acid in the position corresponding to amino acid 444 of SEQ ID NO: 1 when aligned to SEQ ID NO: 1, using a pairwise alignment algorithm, and/or aspartic acid in the position corresponding to amino acid 675 of SEQ ID NO: 1 when aligned to SEQ ID NO: 1, using a pairwise alignment algorithm. The reassortant influenza strains of the invention may also have a NP genome segment with threonine in the position corresponding to amino acid 27 of SEQ ID NO: 4 when aligned to SEQ ID NO: 4 using a pairwise alignment algorithm, and/or asparagine in the position corresponding to amino acid 375 of SEQ ID NO: 4 when aligned to SEQ ID NO: 4, using a pairwise alignment algorithm. Variant influenza strains may also comprise two or more of these mutations. It is preferred that the variant influenza virus contains a variant PB2 segment with both of the amino acids changes identified above, and/or a PA which contains all three of the amino acid changes identified above, and/or a NP segment which contains both of the amino acid changes identified above. The influenza A virus may be a H1 strain.

Alternatively, or in addition, the reassortant influenza A viruses may comprise a PB1 segment which has isoleucine in the position corresponding to amino acid 200 of SEQ ID NO: 2 when aligned to SEQ ID NO: 2 using a pairwise alignment algorithm, and/or asparagine in the position corresponding to amino acid 338 of SEQ ID NO: 2 when aligned to SEQ ID NO: 2 using a pairwise alignment algorithm, and/or isoleucine in the position corresponding to amino acid 529 of SEQ ID NO: 2 when aligned to SEQ ID NO: 2 using a pairwise alignment algorithm, and/or isoleucine in the position corresponding to amino acid 591 of SEQ ID NO: 2 when aligned to SEQ ID NO: 2 using a pairwise alignment algorithm, and/or histidine in the position corresponding to amino acid 687 of SEQ ID NO: 2 when aligned to SEQ ID NO: 2 using a pairwise alignment algorithm, and/or lysine in the position corresponding to amino acid 754 of SEQ ID NO: 2 when aligned to SEQ ID NO: 2 using a pairwise alignment algorithm.

The preferred pairwise alignment algorithm is the Needleman-Wunsch global alignment algorithm [34], using default parameters (e.g. with Gap opening penalty=10.0, and with Gap extension penalty=0.5, using the EBLOSUM62 scoring matrix). This algorithm is conveniently implemented in the needle tool in the EMBOSS package [35].

The choice of donor strain for use in the methods of the invention can depend on the vaccine strain which is to be reassorted. As reassortants between evolutionary distant strains might not replicate well in cell culture, it is possible that the donor strain and the vaccine strain have the same HA and/or NA subtype. In other embodiments, however, the vaccine strain and the donor strain can have different HA and/or NA subtypes, and this arrangement can facilitate selection for reassortant viruses that contain the HA and/or NA segment from the vaccine strain. Therefore, although the 105p30 and PR8-X strains contain the H1 influenza subtype these donor strains can be used for vaccine strains which do not contain the H1 influenza subtype.

Reassortants of the donor strains wherein the HA and/or NA segment has been changed to another subtype can also be used. The H1 influenza subtype of the 105p30 or PR8-X strain may be changed, for example, to a H3 or H5 subtype.

Thus, an influenza A virus may comprises one, two, three, four, five, six or seven viral segments from the 105p30 or PR8-X strains and a HA segment which is not of the H1 subtype. The reassortant donor strains may further comprise an NA segment which is not of the N1 subtype.

The reassortant donor strains may comprise at least one, at least two, at least three, at least four, at least five, at least six or at least seven viral segments from the 105p30 or PR8-X strains of the invention and a H1 HA segment which is derived from a different influenza strain.

The 'second influenza strain' used in the methods of the invention is different to the donor strain which is used.

Reassortant Influenza B Viruses

The invention can also be used to prepare reassortant influenza B strains.

For example, the methods can be used to produce a reassortant influenza B virus which comprises the HA segment from a first influenza B virus and the NP and/or PB2 segment from a second influenza B virus which is a B/Victoria/2/87-like strain. The B/Victoria/2/87-like strain may be B/Brisbane/60/08.

The methods can also be used to produce reassortant influenza B viruses comprising the HA segment from a first influenza B virus and the NP segment from a second influenza B virus which is not B/Lee/40 or B/Ann Arbor/1/66 or B/Panama/45/90. For example, the reassortant influenza B virus may have a NP segment which does not have the sequence of SEQ ID NOs: 80, 100, 103 or 104. The reassortant influenza B virus may also have a NP segment which does not encode the protein of SEQ ID NOs: 19, 23, 44 or 45. The reassortant influenza B virus may comprise both the NP and PB2 segments from the second influenza B virus. The second influenza B virus is preferably a B/Victoria/2/87-like strain. The B/Victoria/2/87-like strain may be B/Brisbane/60/08.

The invention can also be used to produce a reassortant influenza B virus comprising the HA segment from a B/Yamagata/16/88-like strain and at least one backbone segment from a B/Victoria/2/87-like strain. The reassortant influenza B virus may comprise two, three, four, five or six backbone segments from the B/Victoria/2/87-like strain. In a preferred embodiment, the reassortant influenza B virus comprises all the backbone segments from the B/Victoria/2/87-like strain. The B/Victoria/2/87-like strain may be B/Brisbane/60/08.

The methods are also suitable for producing a reassortant influenza B virus comprising viral segments from a B/Victoria/2/87-like strain and a B/Yamagata/16/88-like strain, wherein the ratio of segments from the B/Victoria/2/87-like strain and the B/Yamagata/16/88-like strain is 1:7, 2:6, 4:4, 5:3, 6:2 or 7:1. A ratio of 7:1, 6:2, 4:4, 3:4 or 1:7, in particular a ratio of 4:4, is preferred because such reassortant influenza B viruses grow particularly well in a culture host. The B/Victoria/2/87-like strain may be B/Brisbane/60/08. The B/Yamagata/16/88-like strain may be B/Panama/45/90. In these embodiments, the reassortant influenza B virus usually does not comprise all backbone segments from the same influenza B donor strain.

The methods can also be used to produce a reassortant influenza B virus which comprises:

a) the PA segment of SEQ ID NO: 71, the PB1 segment of SEQ ID NO: 72, the PB2 segment of SEQ ID NO: 73, the NP segment of SEQ ID NO: 74, the NS segment of SEQ ID NO: 76 and the M segment of SEQ ID NO: 75; or b) the PA segment of SEQ ID NO: 71, the PB1 segment of SEQ ID NO: 78, the PB2 segment of SEQ ID NO: 73, the NP segment of SEQ ID NO: 74, the NS segment of SEQ ID NO: 82 and the M segment of SEQ ID NO: 81; or c) the PA segment of SEQ ID NO: 71, the PB1 segment of SEQ ID NO: 78, the PB2 segment of SEQ ID NO: 79, the NP segment of SEQ ID NO: 74, the NS segment of SEQ ID NO: 76 and the M segment of SEQ ID NO: 75; or d) the PA segment of SEQ ID NO: 30, the PB1 segment of SEQ ID NO: 72, the PB2 segment of SEQ ID NO: 73, the NP segment of SEQ ID NO: 74, the NS segment of SEQ ID NO: 76 and the M segment of SEQ ID NO: 75, or e) the PA segment of SEQ ID NO: 71, the PB1 segment of SEQ ID NO: 72, the PB2 segment of SEQ ID NO: 73, the NP segment of SEQ ID NO: 74, the NS segment of SEQ ID NO: 82 and the M segment of SEQ ID NO: 81.

Influenza B viruses currently do not display different HA subtypes, but influenza B virus strains do fall into two distinct lineages. These lineages emerged in the late 1980s and have HAs which can be antigenically and/or genetically distinguished from each other [36]. Current influenza B virus strains are either B/Victoria/2/87-like or B/Yamagata/16/88-like. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [37]. In some embodiments, the reassortant influenza B viruses of the invention may comprise viral segments from a B/Victoria/2/87-like strain. They may comprise viral segments from a B/Yamagata/16/88-like strain. Alternatively, they may comprise viral segments from a B/Victoria/2/87-like strain and a B/Yamagata/16/88-like strain.

Where the reassortant influenza B virus comprises viral segments from two or more influenza B virus strains, these viral segments may be derived from influenza strains which have related neuraminidases. For instance, the influenza strains which provide the viral segments may both have a B/Victoria/2/87-like neuraminidase [38] or may both have a B/Yamagata/16/88-like neuraminidase. For example, two B/Victoria/2/87-like neuraminidases may both have one or more of the following sequence characteristics: (1) not a serine at residue 27, but preferably a leucine; (2) not a glutamate at residue 44, but preferably a lysine; (3) not a threonine at residue 46, but preferably an isoleucine; (4) not a proline at residue 51, but preferably a serine; (5) not an arginine at residue 65, but preferably a histidine; (6) not a glycine at residue 70, but preferably a glutamate; (7) not a leucine at residue 73, but preferably a phenylalanine; and/or (8) not a proline at residue 88, but preferably a glutamine. Similarly, in some embodiments the neuraminidase may have a deletion at residue 43, or it may have a threonine; a deletion at residue 43, arising from a trinucleotide deletion in the NA gene, which has been reported as a characteristic of B/Victoria/2/87-like strains, although recent strains have regained Thr-43 [38]. Conversely, of course, the opposite characteristics may be shared by two B/Yamagata/16/88-like neuraminidases e.g. S27, E44, T46, P51, R65, G70, L73, and/or P88. These amino acids are numbered relative to the 'Lee40' neuraminidase sequence [39]. The reassortant influenza B virus may comprise a NA segment with the characteristics described above. Alternatively, or in addition, the reassortant influenza B virus may comprise a viral segment (other than NA) from an influenza strain with a NA segment with the characteristics described above.

The backbone viral segments of an influenza B virus which is a B/Victoria/2/87-like strain can have a higher level of identity to the corresponding viral segment from B/Victoria/2/87 than it does to the corresponding viral segment of B/Yamagata/16/88 and vice versa. For example, the NP segment of B/Panama/45/90 (which is a B/Yamagata/16/88-like strain) has 99% identity to the NP segment of B/Yamagata/16/88 and only 96% identity to the NP segment of B/Victoria/2/87. Where the reassortant influenza B virus of the invention comprises a backbone viral segment from a B/Victoria/2/87-like strain, the viral segments may encode proteins with the following sequences.

The PA protein may have at least 97% identity, at least 98%, at least 99% identity or 100% identity to the sequence of SEQ ID NO: 83. The PB1 protein may have at least 97% identity, at least 98%, at least 99% identity or 100% identity to the sequence of SEQ ID NO: 84. The PB2 protein may have at least 97%, at least 98%, at least 99% or 100% identity with the sequence of SEQ ID NO: 85. The NP protein may have at least 97% identity, at least 98%, at least 99% identity or 100% identity to the sequence of SEQ ID NO: 86. The $M_1$ protein may have at least 97% identity, at least 98%, at least 99% identity or 100% identity to the sequence of SEQ ID NO: 87. The $M_2$ protein may have at least 97% identity, at least 98%, at least 99% identity or 100% identity to the sequence of SEQ ID NO: 88. The $NS_1$ protein may have at least 97% identity, at least 98%, at least 99% identity or 100% identity to the sequence of SEQ ID NO: 89. The $NS_2$ protein may have at least 97% identity, at least 98%, at least 99% identity or 100% identity to the sequence of SEQ ID NO: 90. In some embodiments, the reassortant influenza B virus may also comprise all of these backbone segments.

Where the reassortant influenza B viruses of the invention comprise a backbone viral segment from a B/Yamagata/16/88-like strain, the viral segment may encode proteins with the following sequences. The PA protein may have at least 97% identity, at least 98%, at least 99% identity or 100% identity to the sequence of SEQ ID NO: 91. The PB1 protein may have at least 97% identity, at least 98%, at least 99% identity or 100% identity to the sequence of SEQ ID NO: 92. The PB2 protein may have at least 97%, at least 98%, at least 99% or 100% identity with the sequence of SEQ ID NO: 93. The NP protein may have at least 97% identity, at least 98%, at least 99% identity or 100% identity to the sequence of SEQ ID NO: 94. The $M_1$ protein may have at least 97% identity, at least 98%, at least 99% identity or 100% identity to the sequence of SEQ ID NO: 95. The $M_2$ protein may have at least 97% identity, at least 98%, at least 99% identity or 100% identity to the sequence of SEQ ID NO: 96. The $NS_1$ protein may have at least 97% identity, at least 98%, at least 99% identity or 100% identity to the sequence of SEQ ID NO: 97. The $NS_2$ protein may have at least 97% identity, at least 98%, at least 99% identity or 100% identity to the sequence of SEQ ID NO: 98.

The invention can be practised with donor strains having a viral segment that has at least about 70%, at least about 75%, at least about 80%, at least about 85%, at least about 90%, at least about 95% or at least about 99%, or 100% identity to a sequence of SEQ ID NOs 71-76 or 77-82. Due to the degeneracy of the genetic code, it is possible to have the same polypeptide encoded by several nucleic acids with different sequences. For example, the nucleic acid sequences of SEQ ID NOs: 33 and 34 have only 73% identity even though they encode the same viral protein. Thus, the invention may be practised with viral segments that encode the same polypeptides as the sequences of SEQ ID NOs 71-76 or 77-82.

Reassortant viruses which contain an NS segment that does not encode a functional NS protein are also within the scope of the present invention. NS1 knockout mutants are described in reference 40. These NS1-mutant virus strains are particularly suitable for preparing live attenuated influenza vaccines.

The 'second influenza strain' used in the methods of the invention is different to the donor strain which is used.

Backbone Libraries

In order to supply influenza vaccines rapidly during a pandemic it is important that the reassortant influenza viruses can grow to high viral titres in a short time frame. The inventors have discovered that it can be useful to test a number of reassortant influenza viruses comprising the HA and NA segments of the vaccine strain in combination with different backbones in order to identify the fastest growing reassortants. The invention thus provides a library comprising two or more influenza backbones. For example, the library may comprise 5, 10, 15, 20, 30, 40, 50, 100 or 200 different influenza backbones. The backbones may be included on expression constructs in the library. In some embodiments, the library may not comprise expression constructs which encode the HA and/or NA segments of influenza viruses as these segments will come from the circulating influenza strain. The library may comprise at least one influenza backbone as described in the preceding sections.

Each expression construct in the library may encode all the backbone segments of an influenza virus. It is also possible to include expression constructs which do not encode all the backbone segments.

For example, the library may comprise expression constructs which encode one, two, three, four, five, six or seven viral backbone segment(s).

When a new circulating strain is identified, the HA and NA segments of that strain may be included in an expression construct (which may be a synthetic expression construct). This expression construct and the expression constructs in the library can be co-transfected into host cells (which are preferably all of the same cell line or the same cell type). Cells which receive expression constructs that encode all the viral segments of an influenza virus will produce reassortant influenza viruses from these expression constructs. In this manner, it is possible to produce a number of different reassortant influenza viruses which all comprise the same HA and NA segments but which will have different backbone segments. The growth rate of these reassortant influenza viruses can be determined using standard methods in the art and the fastest growing reassortant can be selected for vaccine production.

Virus Preparation

In one embodiment, the invention provides a method for producing influenza viruses comprising steps of (a) infecting a culture host with a reassortant virus of the invention; (b) culturing the host from step (a) to produce the virus; and optionally (c) purifying the virus produced in step (b).

The culture host may be cells or embryonated hen eggs, as described above. Where cells are used as a culture host in this aspect of the invention, it is known that cell culture conditions (e.g. temperature, cell density, pH value, etc.) are variable over a wide range subject to the cell line and the virus employed and can be adapted to the requirements of the application. The following information therefore merely represents guidelines.

As mentioned above, cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. When culturing the infected cells (step b), the cells are preferably cultured at a temperature of between 30° C. and 36° C. or between 32° C. and 34° C. or at 33° C. This is particularly preferred, as it has been shown that incubation of infected cells in this temperature range results in production of a virus that results in improved efficacy when formulated into a vaccine [41].

Oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8\text{-}25\times10^5$ cells/mL in the batch system or preferably about $5\text{-}20\times10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Virus may be grown on cells in adherent culture or in suspension. Microcarrier cultures can be used. In some embodiments, the cells may thus be adapted for growth in suspension.

The methods according to the invention also include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

The culture host may be eggs. The current standard method for influenza virus growth for vaccines uses embryonated SPF hen eggs, with virus being purified from the egg contents (allantoic fluid). It is also possible to passage a virus through eggs and subsequently propagate it in cell culture and vice versa.

Vaccine

The invention utilises virus produced according to the method to produce vaccines.

Vaccines (particularly for influenza virus) are generally based either on live virus or on inactivated virus. Inactivated vaccines may be based on whole virions, split virions, or on purified surface antigens. Antigens can also be presented in the form of virosomes. The invention can be used for manufacturing any of these types of vaccine.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 42-47, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [48] (nucleic acid free viral-like liposomal particles). Virosomes can be prepared by solubilization of virus with a detergent followed by removal of the nucleocapsid and reconstitution of the membrane containing the viral glycoproteins.

An alternative method for preparing virosomes involves adding viral membrane glycoproteins to excess amounts of phospholipids, to give liposomes with viral proteins in their membrane.

The methods of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 49). Live virus vaccines include MedImmune's FLUMIST™ product (trivalent live virus vaccine).

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [50,51]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

As well as being suitable for immunizing against inter-pandemic strains, the compositions of the invention are particularly useful for immunizing against pandemic or potentially-pandemic strains. The invention is suitable for vaccinating humans as well as non-human animals.

Other strains whose antigens can usefully be included in the compositions are strains which are resistant to antiviral therapy (e.g. resistant to oseltamivir [52] and/or zanamivir), including resistant pandemic strains [53].

Compositions of the invention may include antigen(s) from one or more (e.g. 1, 2, 3, 4 or more) influenza virus strains, including influenza A virus and/or influenza B virus provided that at least one influenza strain is a reassortant influenza strain of the invention. Compositions wherein at least two, at least three or all of the antigens are from reassortant influenza strains of the invention are also envisioned. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [54], including antigens from two influenza A virus strains and two influenza B virus strains, or three influenza A virus strains and one influenza B virus strain.

Pharmaceutical Compositions

Vaccine compositions manufactured according to the invention are pharmaceutically acceptable. They usually include components in addition to the antigens e.g. they typically include one or more pharmaceutical carrier(s) and/or excipient(s). As described below, adjuvants may also be included. A thorough discussion of such components is available in reference 55.

Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e. less than 5 μg/ml) mercurial material e.g. thiomersal-free [46, 56]. Vaccines containing no mercury are more preferred.

An α-tocopherol succinate can be included as an alternative to mercurial compounds [46]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [57], but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide (CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Host Cell DNA

Where virus has been isolated and/or grown on a cell line, it is standard practice to minimize the amount of residual cell line DNA in the final vaccine, in order to minimize any potential oncogenic activity of the DNA.

Thus a vaccine composition prepared according to the invention preferably contains less than 10 ng (preferably less than ing, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 58 & 59, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [60].

Adjuvants

Compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below).

Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy(oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines [61].

Preferred emulsions have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [62-64], as described in more detail in Chapter 10 of ref. 65 and chapter 12 of ref 66. The MF59 emulsion advantageously includes citrate ions e.g. 10 mM sodium citrate buffer.
- An emulsion comprising squalene, a tocopherol, and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g. 0.90) as this can provide a more stable emulsion. Squalene and polysorbate 80 may be present in a volume ratio of about 5:2 or at a weight ratio of about 11:5. Thus the three components (squalene, tocopherol, polysorbate 80) may be present at a weight ratio of 1068:1186:485 or around 55:61:25. One such emulsion ('AS03') can be made by dissolving Tween 80 in PBS to give a 2% solution, then mixing 90 ml of this solution with a mixture of (5 g of DL a tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [67] e.g. in the ratios discussed above.
- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [68] (0.05-1% Thr-MDP, 5% squalane, 2.5% Pluronic L121 and 0.2% polysorbate 80). It can also be used without the Thr-MDP, as in the "AF" adjuvant [69] (5% squalane, 1.25% Pluronic L121 and 0.2% polysorbate 80). Microfluidisation is preferred.

- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [70]. The emulsion may also include one or more of: alditol; a cryoprotective agent (e.g. a sugar, such as dodecylmaltoside and/or sucrose); and/or an alkylpolyglycoside. The emulsion may include a TLR4 agonist [71]. Such emulsions may be lyophilized.
- An emulsion of squalene, poloxamer 105 and Abil-Care [72]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).
- An emulsion having from 0.5-50% of an oil, 0.1-10% of a phospholipid, and 0.05-5% of a non-ionic surfactant. As described in reference 73, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 74, produced by addition of aliphatic amine to desacylsaponin via the carboxyl group of glucuronic acid), dimethyidioctadecylammonium bromide and/or N,N-dioctadecyl-N,N-bis(2-hydroxyethyl)propanediamine.
- An emulsion in which a saponin (e.g. QuilA or QS21) and a sterol (e.g. a cholesterol) are associated as helical micelles [75].
- An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [76].
- An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [76].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form.

The antigen will generally be in an aqueous form, such that the vaccine is finally prepared by mixing two liquids. The volume ratio of the two liquids for mixing can vary (e.g. between 5:1 and 1:5) but is generally about 1:1 and this is most preferred. Where concentrations of components are given in the above descriptions of specific emulsions, these concentrations are typically for an undiluted composition, and the concentration after mixing with an antigen solution will thus decrease (e.g. it will be half the concentration where the antigen and the adjuvant are mixed at a ratio of 1:1).

Packaging of Vaccine Compositions

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccine compositions are suitable for administration to human or non-human animal subjects, such as pigs or birds, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [77]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [78-80], oral [81], intradermal [82,83], transcutaneous, transdermal [84], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (≥60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

Other Biologicals

Whilst the invention has been described with reference to influenza viruses and influenza vaccines, the invention can also be used for the production of other viruses which can be produced by reverse genetics, as well as other viral vaccines. For example, the methods of the invention are particularly suitable for producing viruses such as dengue virus, rotaviruses, measles virus, rubella virus, coronaviruses.

Other biologicals which can be produced recombinantly can also be produced by the methods of the invention. Suitable examples include antibodies, growth factors, cytokines, lymphokines, receptors, hormones, diagnostic antigens, etc.

The method steps described herein will apply mutatis mutandis to these viruses, vaccines or biologicals.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

The various steps of the methods may be carried out at the same or different times, in the same or different geographical locations, e.g. countries, and by the same or different people or entities.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 85. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 86.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 85. A preferred alignment program is GCG Gap (Genetics Computer Group, Wisconsin, Suite Version 10.1), preferably using default parameters, which are as follows: open gap=3; extend gap=1.

BRIEF DESCRIPTION OF THE DRAWINGS

FIG. 3. Performance of synthetic H7N9 reassortant viruses from the simulated pandemic response. (A) Titers of influenza viruses in culture fluid harvested from MDCK-supplemented 293T cells 48 hours (dotted columns) and 72 hours (white columns) after co-transfection with the indicated backbone plasmids and synthetic HA and NA gene constructs. Viral titers were determined by a focus formation assay using MDCK cell monolayers. (B) Replication kinetics of synthetic H7N9 reassortant viruses in MDCK 33016PF suspension cultures. (C) HA yields from synthetic H7N9 viruses in MDCK suspension cultures, determined by RP-HPLC after purification of viruses on sucrose density gradients. The y-axis in FIGS. 3(A) and (B) shows infectious units (log 10 IU/mL). The y-axis in FIG. 3(C) shows HA yield in μg/mL.

FIG. 7. Replication kinetics of synthetic H7N9 reassortant viruses with alternative NA UTRs in MDCK 33016PF suspension cultures. Replication kinetics of synthetic H7N9 viruses with alternative NA UTRs and different backbones, (A) PR8x, (B) #19, and (C) #21, in MDCK suspension cultures. Starting m.o.i. was 0.001. The x-axis indicates the hours post infection. The y-axis indicates infectious units (log 10 IU/mL).

FIG. 8. HA yield by turkey RBC agglutination by synthetic H7N9 viruses with alternative NA UTRs. The y-axis indicates the HA units.

FIG. 9 compares the HA content (determined by lectin-capture ELISA) of sucrose gradient-purified viruses harvested at 60 h post-infection from MDCK cell cultures infected with reverse genetics-derived 6:2 reassortants containing either the PR8-X or #21 backbone with the HA and NA segments from (A) a pandemic-like H1 strain (strain 1) or (B) a second pandemic-like strain (strain 2).

FIG. 10 compares the HA content (determined by a lectin-capture ELISA) of unpurified viruses harvested at 60 h post-infection from MDCK cell cultures infected with reverse genetics-derived 6:2 reassortants containing either the PR8-X or #21 backbone with the HA and NA segments from (A) a pre-pandemic H1 strain (strain 1) and (B) a second pre-pandemic H1 strain (strain 2).

FIG. 12 compares virus titers (determined by focus formation assay (FFA); In FIG. 12A, the individual dots represent data from single eggs. The line represents the average of the individual data points. The y-axis indicates infectious units/ml. In FIG. 12B, the black bar represents the reference vaccine strain (derived from WHO-Collaborating Centre-supplied strain), the grey bar represents a reassortant virus containing the PR8-X backbone, and the white bar represents a reassortant virus containing the #21 backbone. The y-axis indicates HA yield in μg/ml for pooled egg samples.

MODES FOR CARRYING OUT THE INVENTION

Figure 1A:
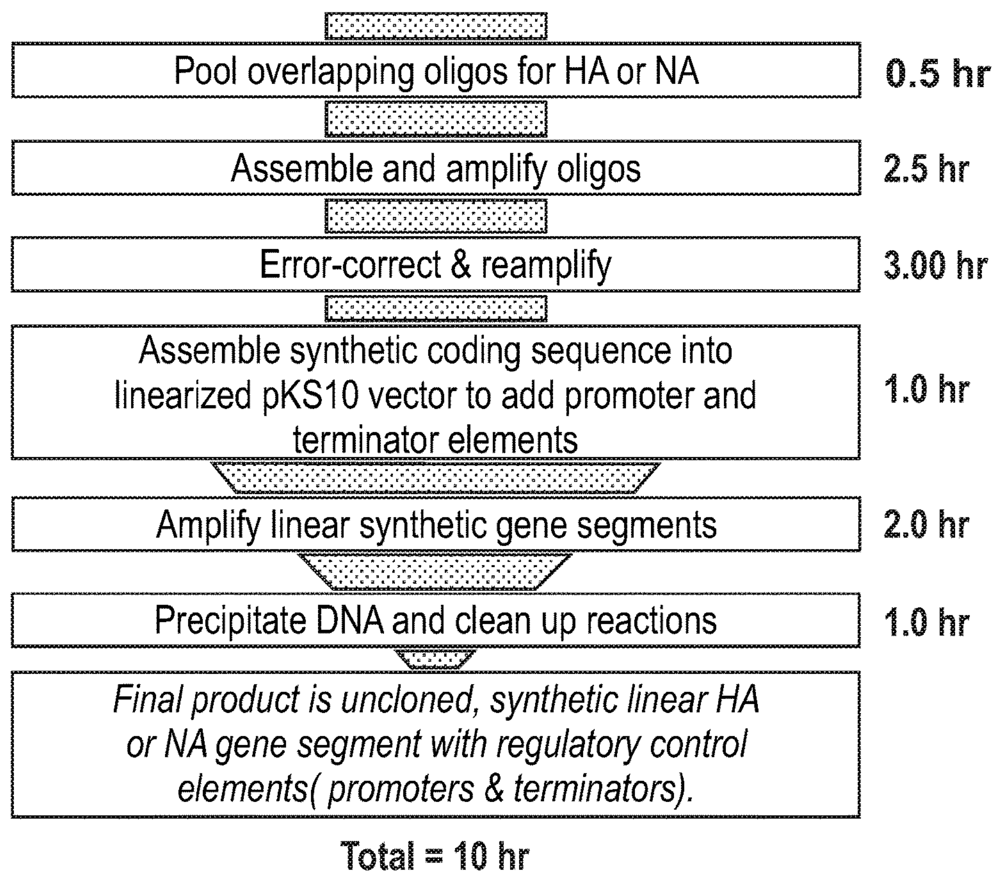
FIG. 1. Method of synthetic gene segment assembly and error correction. (A) Process flow. Time for performance of each step is indicated on the right. (B) Schematic diagram of process. "X" indicates sites of oligonucleotide synthesis errors. In the circular DNA and final assembled gene diagrams (the bottom two), pKS10 sequences are white, and influenza coding sequences are black. (C) Ethidium bromide stained agarose gel of linear synthetic HA and NA genes, including regulatory elements used for virus rescue. MW—molecular weight marker.

Increased Gene Synthesis Speed and Accuracy Through Enzymatic Assembly and In Vitro Error Correction.

A purely enzymatic one-step, isothermal assembly method of gene assembly, previously used to synthesize the entire 16,299 base pair mouse mitochondrial genome from 600 overlapping 60-base oligonucleotides (6), was adapted for the generation of synthetic DNA copies of influenza virus genome segments. The method uses 5' T5 exonuclease (Epicentre), Phusion DNA polymerase (New England Biolabs [NEB]) and Taq DNA ligase (NEB) to join multiple DNA fragments during a brief 50° C. reaction (7). The method was selected to assemble genes for synthetic vaccine seeds because it is rapid and readily automated. All bases of the resulting synthetic genes have their origin in chemically synthesized oligonucleotides. Using current techniques, DNA oligonucleotide synthesis has an error rate of about 1 per 325 bases, typically due to missing bases from failed chemical coupling, and the error rate increases with the length of the oligonucleotide synthesized (6). When DNA copies of the 1.7 kb HA and 1.5 kb NA viral RNA genome segments are synthesized by this technique using oligonucleotides approximately 60 bases in length with 30 bases of overlap between oligonucleotides on opposite strands, only 3% of the synthetic products have the correct sequence. During the mouse mitochondrial genome synthesis, subassemblies were cloned and sequenced, and sets of error-free sequences were selected for subsequent rounds of assembly (6). For the purpose of rapid influenza vaccine seed virus generation, this method of error correction would introduce unacceptable delays.

The problem of synthesizing DNA copies of HA and NA genome segments with both accuracy and speed was solved by (i) increasing the overlap between oligonucleotides, (ii) introducing an enzymatic error correction step, and (iii) increasing the number of oligonucleotides assembled at once, eliminating the need for stepwise assembly via subassemblies (FIGS. 1*a* and *b*). Specifically, the length of oligonucleotides was increased to 60-74 bases, and full length genes (including 5' and 3' un-translated regions) were assembled from staggered sets of oligonucleotides that contained all residues of a double-stranded DNA molecule so that, prior to ligation, the full double-stranded gene can be annealed. In practice, a software algorithm generates a set of sequences for oligonucleotides (a maximum of 96 oligonucleotides per HA, NA pair) that meet these criteria. After chemical synthesis of the oligonucleotides, enzymatic isothermal assembly, and PCR amplification, error-containing DNA is removed enzymatically by treating melted and re-annealed DNA with the commercially available ErrASE error correction kit (Novici Biotech), which excises areas of base mismatch in double-stranded DNA molecules before another round of PCR amplification.

After agarose gel verification of the products' sizes, the control sequences (including Pol I and Pol II promoters and their terminator and polyadenylation signals) needed to generate RNA genome segments and mRNA for virus rescue are added by isothermally coupling the synthetic DNA with a linearized plasmid (pKS10) that contains these regulatory sequences (87). Nucleotide identity between the ends of the linearized plasmid and the 5' and 3' primers used for gene synthesis guide this assembly. The assembled molecule is the substrate for a round of high fidelity PCR amplification using primers outside the transcription control regions.

After purification and concentration of the amplicons, approximately 10 μg of assembled linear DNA cassettes that contain the influenza gene flanked by control sequences are obtained, ready for transfection into the MDCK 33016PF cell line for influenza virus rescue (FIG. 1*c*). The time from receipt of oligonucleotides to a purified HA or NA-encoding DNA cassette ready for transfection is approximately 10 hours. While virus rescue is underway using the enzymatically assembled, error corrected, and amplified DNA, parallel cloning and sequencing verifies the sequence of the assembled genes. Typically, 80-100% of the full-length sequences obtained are correct.

Optimized Rescue of Influenza Viruses from Synthetic DNA on a Vaccine Manufacturing Cell Line.

The rescue protocol for synthetic seed virus generation is adapted from a previously described eight-plasmid ambisense system in which each expression plasmid has a cDNA copy of a viral gene segment bounded at the 5' end by a Pol II promoter to drive transcription of messenger RNA and at the 3' end by a human Pol I promoter to drive transcription of negative-stranded influenza RNA genome segments (88). The manufacturing-qualified MDCK 33016PF cell line is a less efficient substrate for transfection and influenza virus rescue by reverse genetics than 293T cells (which are not qualified for vaccine production). Influenza virus reverse genetic rescue has been described using Vero cells (some banks of which are qualified for vaccine production) (89, 90). However, using one cell line for vaccine virus rescue and a different cell line for antigen production would add adventitious agent risk and regulatory and manufacturing complexity. Therefore, we elected to increase the efficiency of reverse genetic DNA rescue in MDCK 33016PF cells so that a single cell line can be used for seed generation and vaccine antigen production. Although Pol I promoters are generally species specific, human Pol I efficiently drives transcription in MDCK 33016PF cells, which are of canine origin.

Figure 4A:
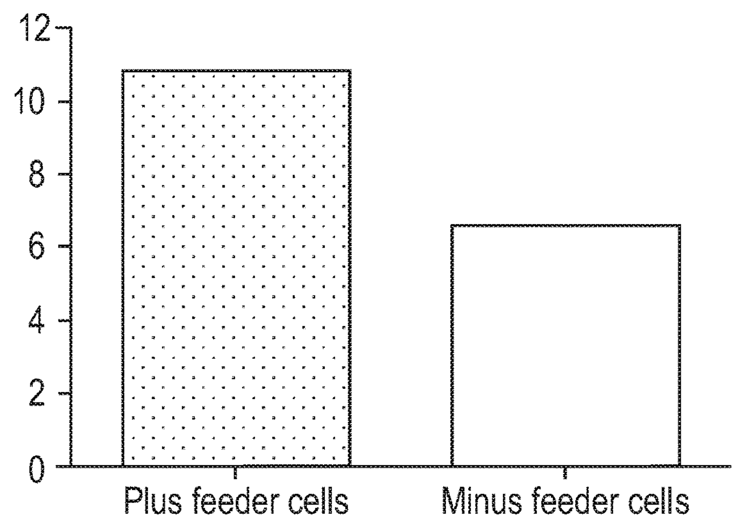
FIG. 4. Effect of MDCK feeder cell addition 24 hours after transfection of MDCK cells on rescue efficiency. Titers of recombinant viruses containing the PR8x backbone with HA and NA segments from either (A) A/WSN/1933 (H1N1) or (B) A/California/04/2009 were measured 72 hours after transfection by a focus formation assay. The dotted column shows the results with additional cells whilst the white column shows the results without additional cells. The y-axis indicates infectious units (log 10 IU/mL).
Figure 4B:
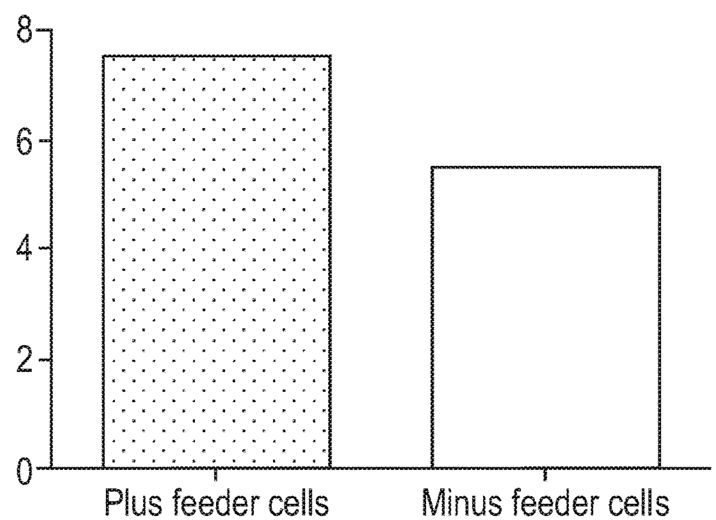
Figure 5A:
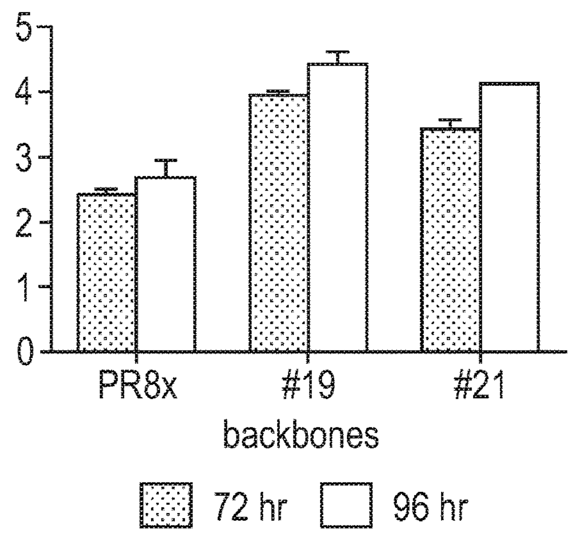
FIG. 5. Synthetic influenza virus rescue efficiencies. Representative data showing effect of optimized backbones on virus rescue efficiency from transfected cultures of MDCK cells. Detection of influenza viruses in culture fluid harvested at different time points after transfection with the indicated backbone plasmids and synthetic HA and NA constructs, or 24-48 hours after a blind passage using 500 μl of the culture fluid on fresh MDCK cell monolayers (Passage 1). Viral titers were determined using a focus formation assay for (A) an H1N1 strain, (B) an H3N2 strain, (C) an attenuated H5N1 strain, (D) a swine origin H3N2v strain, (E) a B/Yamagata lineage strain, and (F) a B/Victoria lineage strain. The y-axis indicates infectious units (log 10 IU/mL).
Figure 5B:
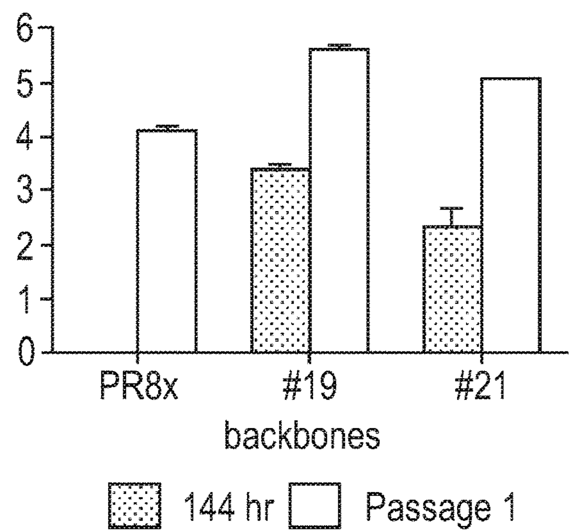
Figure 5E:
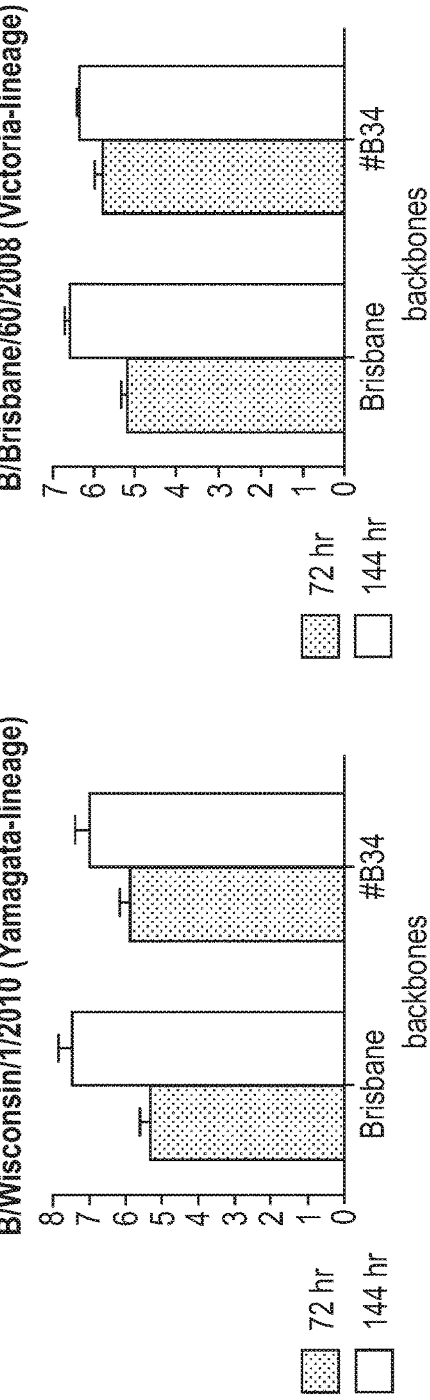
Figure 5F:
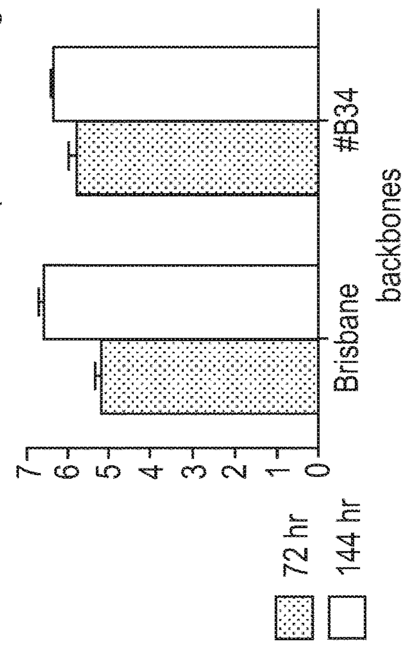

One μg of each linear synthetic cassette encoding HA or NA is co-transfected into MDCK 33016PF cells together with 1 μg of each ambisense plasmid that encodes PA, PB1, PB2, NP, NS, or M and a helper plasmid that encodes the protease TMPRSS2 (91). To increase rescue efficiency, we add cultures of fresh (un-transfected) MDCK 33016PF cells after transfection, which increases the probability of virus recovery, presumably by providing a healthier population of cells in which rescued viruses can further amplify (FIG. 4). Viruses are detected in cell culture medium within 72 hours after transfection (approximately 24 hours later than after transfection of Vero or 293T cells), using a focus-formation assay in which the medium from the transfected culture is added to a fresh MDCK cell monolayer, and infectious virus is detected by immuno-staining for expressed NP.

and NA). The initial backbone improvement resulted from using genes from a PR8 variant (designated PR8x) that had been adapted over five passages to growth in MDCK 33016PF cells. Additional improvements resulted from combining backbone genome segments of multiple strains. During pilot manufacturing of influenza vaccines using MDCK 33016PF cells, several human influenza viruses, such as strain 105p30 (an A/New Caledonia/20/1999 (H1N1)-like strain that was passaged 30 times in MDCK 33016PF cells), were adapted to grow efficiently in cultured cells, although not as efficiently as strain PR8x. Synthesized viruses with HA and NA genes from historical H3N2 strains and a backbone (designated #19) composed of NP, PB1, and PB2 genome segments from strain 105p30 and M, NS, and PA genome segments from strain PR8x often outperformed equivalent viruses with entirely PR8x backbones in reverse genetic rescue efficiency and yield of HA (table 1 and FIG. 5). Similarly, synthesized viruses with HA and NA genes from H1N1 strains and a backbone (designated #21) with the PB1 genome segment of A/California/7/2009 and the other genome segments from strain PR8x often had greater rescue efficiencies and HA yields than equivalent viruses with entirely PR8x backbones (table 1 and FIG. 5). This finding is consistent with a report that the A/California PB1 genome segment is preferentially found in the reassortant progeny of co-infections of chicken eggs with A/California/7/2009 and a donor strain that has a PR8 backbone (18).

TABLE 1

Representative data showing virus titers and HA yields (in mass per volume of cell culture medium before purification) from synthetic influenza viruses relative to conventional vaccine viruses (reference strains obtained from the US CDC or the UK National Institute for Biological Standards and Control) in MDCK 33016PF cells.

| | Reference strain | FFA titer | HA yield by RP-HPLC | HA yield by ELISA | Best backbone |
|---|---|---|---|---|---|
| Synthetic H1N1 strain | | | | | |
| A/Christchurch/16/2010[a,b] | NIB74[b] | 4.9 | 1.6 | 2.3 | #21 |
| A/Brisbane/10/2010[a] | wild-type | 19 | 2.1 | 7.2 | #21 |
| A/Brisbane/59/2007 | IVR-148 | 5.5 | 1.9 | 2.9 | #21 |
| A/Solomon/3/2006 | IVR-145 | 3.4 | 1.8 | 5.9 | #21 |
| Synthetic H3N2 strain | | | | | |
| A/Victoria/361/2011[a,b] | IVR-165[b] | 2.6 | 2.5 | 1.4 | PR8x |
| A/Victoria/210/2009[a] | X187 | 2.6 | 2.3 | 1.7 | PR8x |
| A/Wisconsin/15/2009[b] | X183[b] | 35 | below detection | 15 | #19 |
| A/Uruguay/716/2007[b] | X175C[b] | 2.0 | 1.3 | 1.4 | #19 |
| Synthetic H5N1 strain | | | | | |
| A/turkey/Turkey/1/2005[a,b] | NIBRG23[b] | 1.9 | 1.6 | n/a | #19 |
| Synthetic H3N2v strain | | | | | |
| A/Indiana/8/2011[a,b] | X213[b] | 1.9 | 2.3 | n/a | #21 |
| Synthetic B-Yamagata strain | | | | | |
| B/Wisconsin/1/2010[a,b] | wild-type[b] | 1.7 | 1.4 | 1.7 | Brisbane |
| B/Brisbane/3/2007 | wild-type | 0.88 | 3.5 | 5.2 | #B34 |
| Synthetic B-Victoria strain | | | | | |
| B/Brisbane/60/2008[a] | wild-type | 0.72 | 1.8 | 0.67 | Brisbane |

Data values are normalized and shown as fold-improvement over reference strains, where values of the reference strains are set to 1.0. RP-HPLC or lectin-capture ELISA was used to detect HA antigen directly from the culture medium of virus-infected MDCK cells (m.o.i = 0.001 or 0.0001), unless specified.

[a]= recombinant viruses containing synthetic HA and NA segments

[b]= viruses from culture medium were purified by sucrose-density gradient prior to characterization n/a = data not available because strain-specific anti-sera were not available for ELISA below detection = data not available because the reference strain had undetectable HA levels by RP-HPLC Improved Backbones for Synthetic Virus Rescue.

A significant increase in rescue efficiency was provided by using improved influenza backbones (sets of genome segments encoding influenza virus proteins other than HA Historically, most influenza type B vaccine seeds have been wild type viruses, not reassortants, because wild type influenza B viruses generally provide adequate yields. To use the synthetic procedures for influenza B viruses more readily, two optimized type B backbones that provide consistent rescue of synthetic influenza B viruses were developed (table 1 and FIG. 5). In the first (designated Brisbane), all backbone genome segments originate from B/Brisbane/60/2008; in the second (designated #B34), the genome segments encoding PA, PB1, PB2, and NP originate from B/Brisbane/60/2008, and those encoding M and NS originate from B/Panama/45/1990.

Overall, the use of optimized backbones for A strains increased rescue efficiencies up to 1000-fold (as measured by infectious titers obtained after transfection, FIG. 5) and increased HA yields in research scale infections of MDCK 33016PF cells by 30% to 15-fold, depending on the strain and assay used for HA detection (table 1). In general, yields of HA from these viruses are also increased relative to those from viruses with PR8 backbones when the viruses are propagated in embryonated chicken eggs (table 2). To make use of such strain-specific differences, an optimal synthetic seed generation strategy would combine the HAs and NAs from circulating strains of interest with a panel of alternative backbones to maximize the chances of isolating a high-yielding vaccine virus.

UTRs for H7 and N9 genomic segments created from high quality sequence data in GenBank. This analysis revealed heterogeneity in the non-coding regions of NA genes of H7N9 strains (U/C at 1434 in the positive-sense orientation). So, alternative sets of 5' NA oligonucleotides were used to construct two variants of the NA cassettes.

Figure 2:
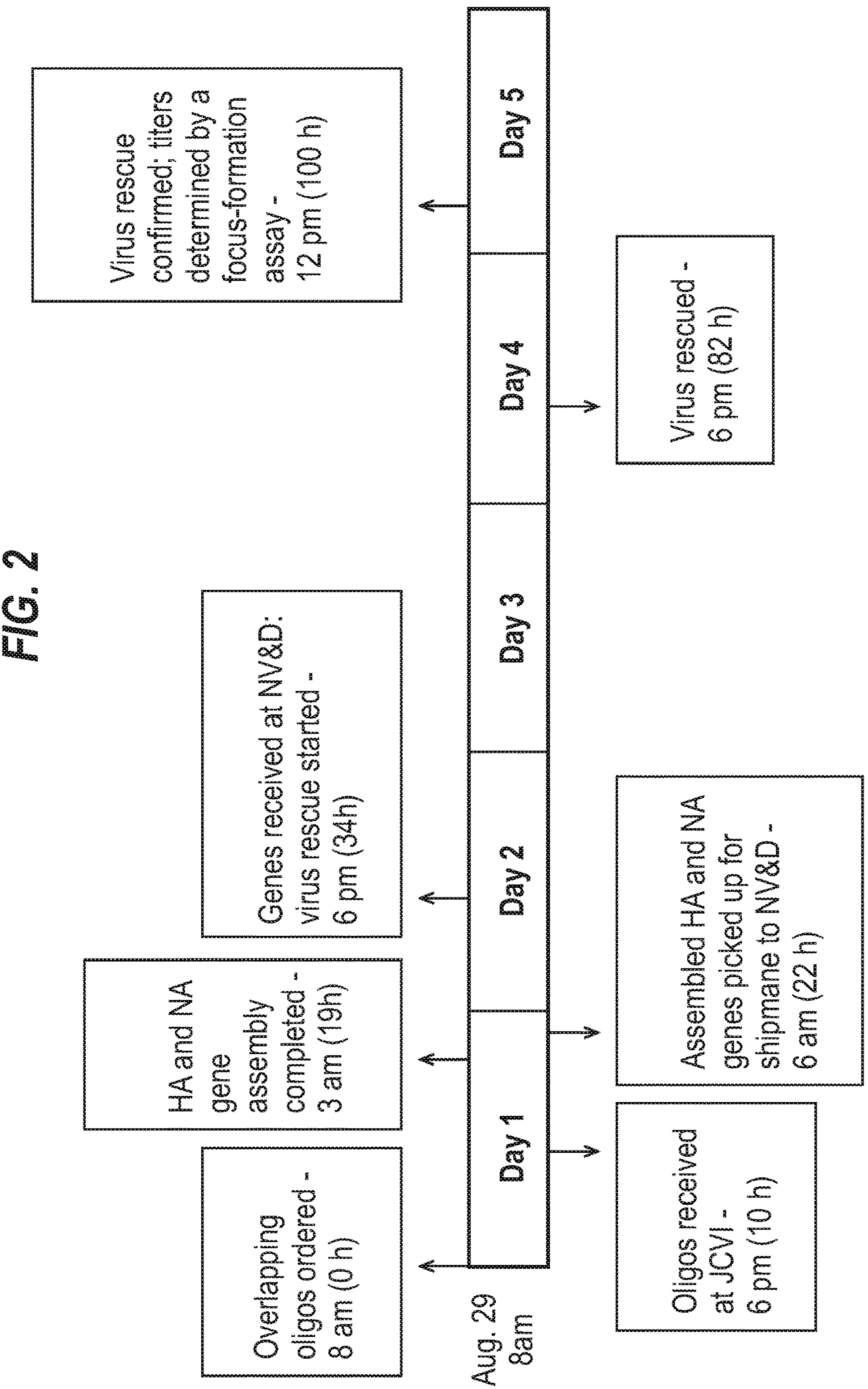
FIG. 2. Timeline of rescue of synthetic H7N9 influenza viruses from transmission of oligonucleotide sequence information to confirmation of recovered viruses.
Figure 6:
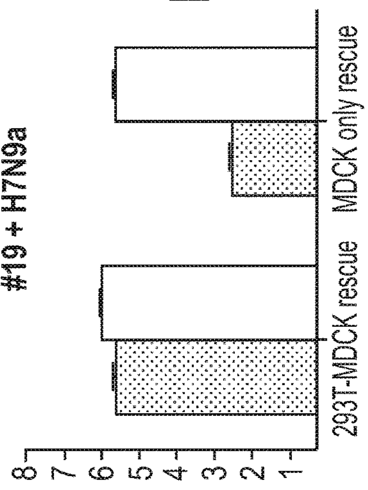
FIG. 6. Rescue of synthetic H7N9a viruses from either MDCK-supplemented 293T cells or from MDCK cells only. Detection of influenza viruses in culture fluid harvested 48 hours (dotted columns) and 72 hours (white columns) after transfection with the #19 backbone plasmids and synthetic H7 and N9 constructs. Viral titers were determined on MDCK cell monolayers using a focus formation assay. The y-axis indicates infectious units (log 10 IU/mL).

Oligonucleotide synthesis began at 8:00 am EDT on Monday, Aug. 29, 2011 (FIG. 2). By noon on Friday, September 4, immunostaining of a secondary culture confirmed that the virus had been rescued. The 4 days and 4 hours from start of synthesis to detection of rescued virus included time spent shipping DNA from the oligonucleotide synthesis and gene assembly laboratories in California to the virus rescue laboratory in Massachusetts. When all functions are consolidated in one location, the potential for delays and mishaps due to shipping will be reduced. The original proof-of-concept rescues were conducted using 293T cells; rescue of the strains using MDCK cells, as would be done during an actual pandemic response, slows detection of rescued virus by approximately 24 hours (FIG. 6). The sequences of the HA and NA genome segments of the synthetic H7N9 reassortant viruses from the proof-of-concept exercise were determined following two rounds of virus amplification in MDCK 33016PF cells and were identical to those used to program oligonucleotide synthesis. Two-way hemagglutination inhibition (HI) testing (reciprocal HI assays using antigen from the synthetic and natural strains and ferret sera drawn after synthetic and natural virus infection) (19, 20) demonstrated antigenic identity of the synthetic virus to A/goose/Nebraska/17097-4/2011 (H7N9), which had subsequently been revealed as the wild type virus from which the sequences that were electronically transmitted to the virus synthesis group had been obtained (Table 1).

TABLE 2

Representative data showing virus titers and HA yields (in mass per volume of egg allantoic fluid before purification) from synthetic influenza viruses relative to conventional vaccine viruses (reference strains obtained from the US CDC or the UK National Institute for Biological Standards and Control) in chicken eggs.

| Synthetic strain | Reference strains | FFA titer | HA titer by GP-RBC agglutination | HA yield by RP-HPLC | HA yield by ELISA | Best backbone |
|---|---|---|---|---|---|---|
| A/H1N1/Christchurch/16/2010[b] | NIB74 | 3.0 | 3.5 | 18 | 8.4 | #21 |
| A/H3N2/Victoria/210/2009[b] | X187 | 0.94 | 1.3 | not tested | 1.2 | PR8x |
| A/H3N2/Victoria/361/2011[a] | IVR-165 | 6.4 | 2.6 | not tested | 3.4 | #21 |
| A/H3N2v/Indiana/8/2011[a, b] | X213 | not tested | 3.0 | 1.6 | n/a | PR8x |
| B/Yam/Wisconsin/1/2010[a] | wild-type | 4.7 | 3.4 | not tested | 3.5 | Brisbane |
| B/Vic/Brisbane/60/2008[a] | wild-type | 1.1 | 0.82 | not tested | 0.79 | Brisbane |

Data values are normalized and shown as fold-improvement over reference strains, where values of the reference strains are set to 1.0. GP-RBC agglutination, RP-HPLC or lectin-capture ELISA was used to detect HA antigen directly from the allantoic fluid of virus-infected chicken eggs, unless specified.

[a]= recombinant viruses containing synthetic HA and NA genome segments

[b]= viruses from egg allantoic fluid were purified by sucrose density gradient before characterization n/a = data not available because strain-specific antisera were not available for ELISA not tested = data not available because assay was not performed Speed of Synthetic Vaccine Virus Generation in a Simulated Pandemic Response.

Figures 3A, 3B:
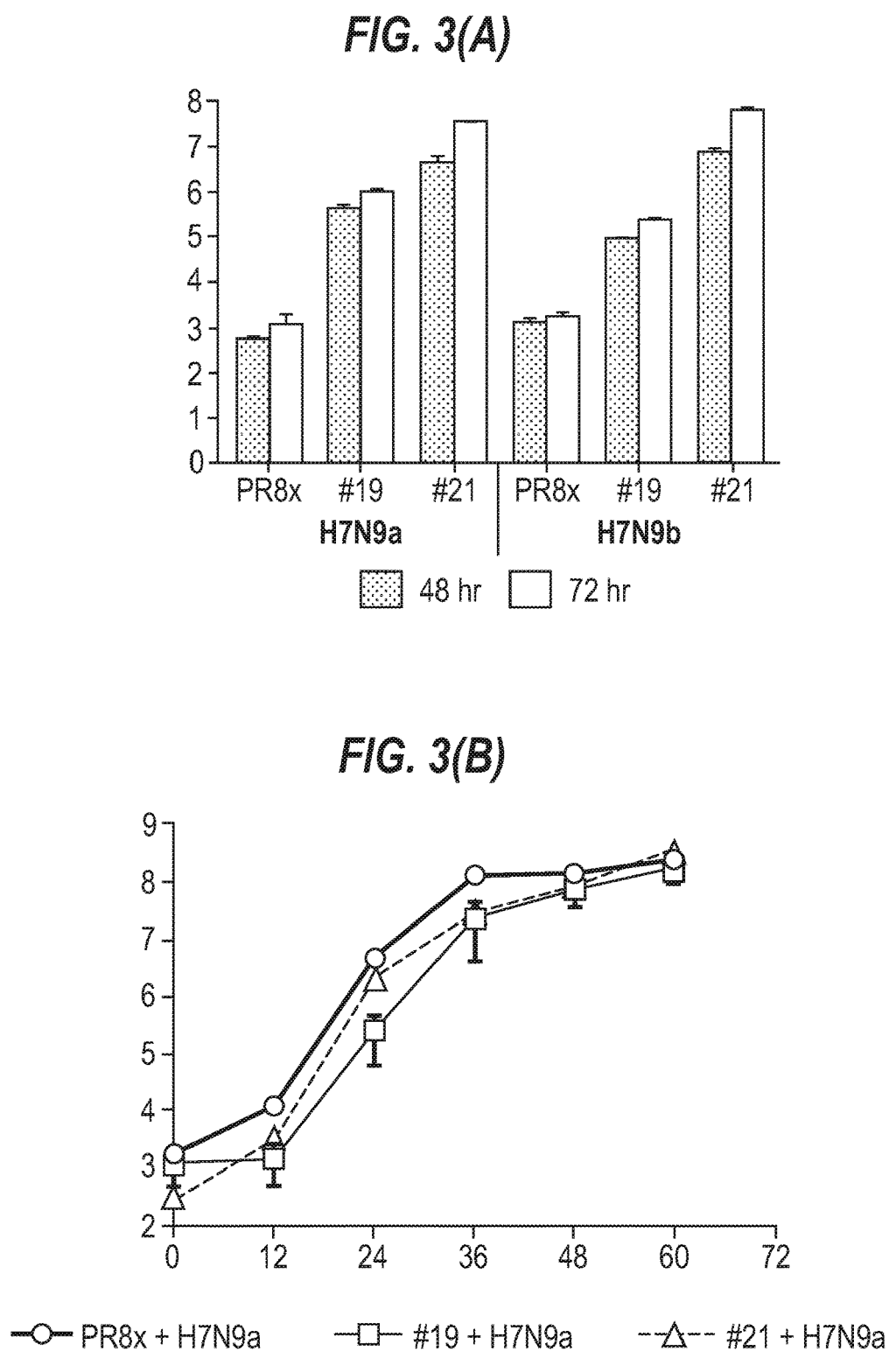
Figure 3C:
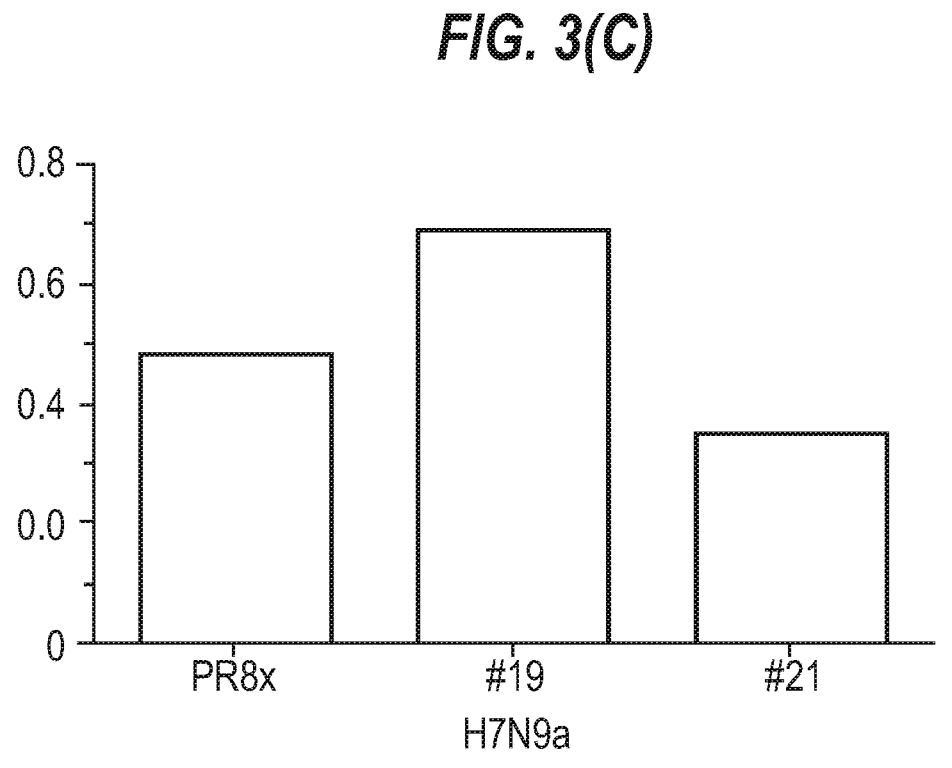
Figures 7A, 7B, 7C:
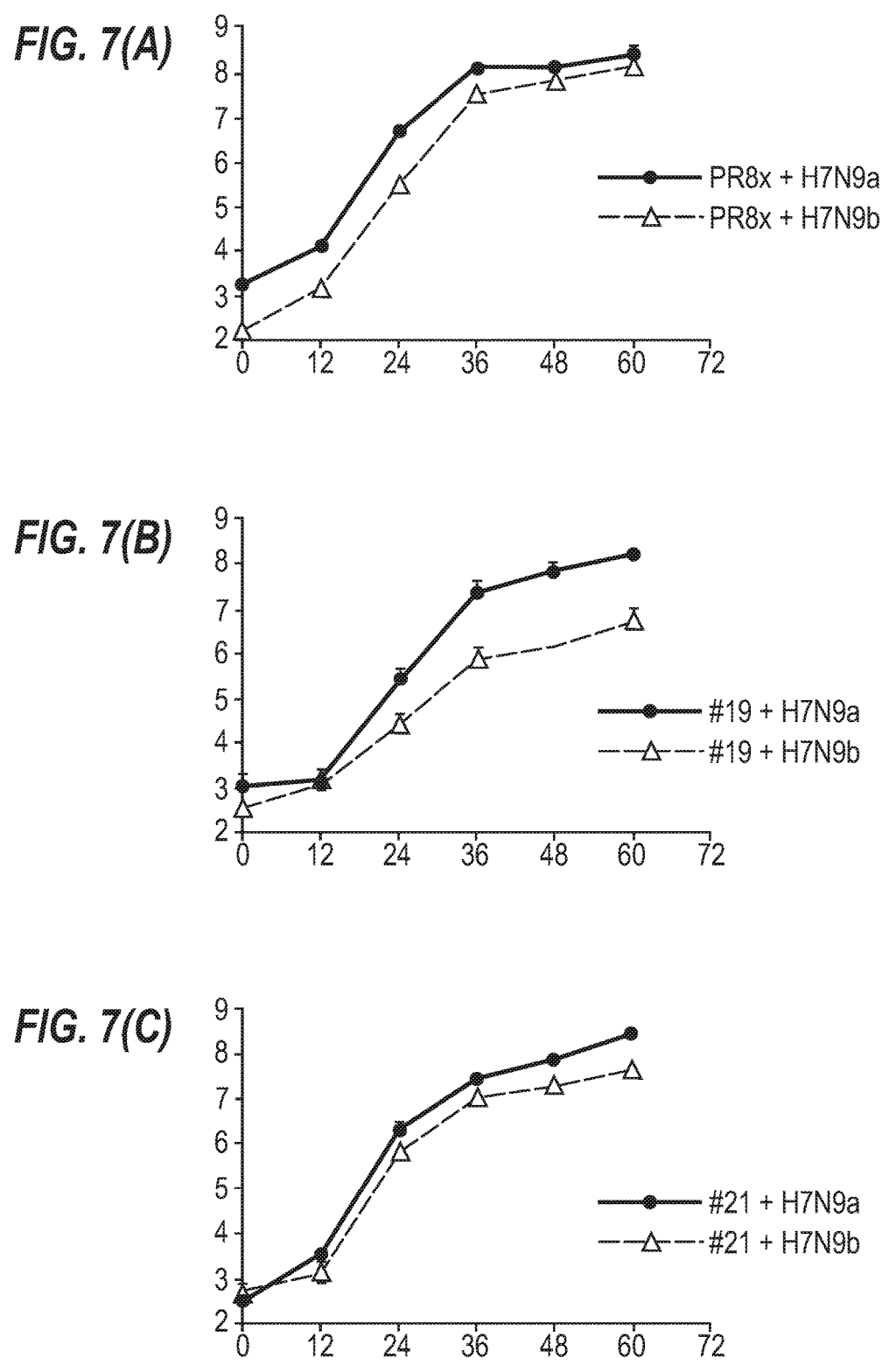
Figure 8:
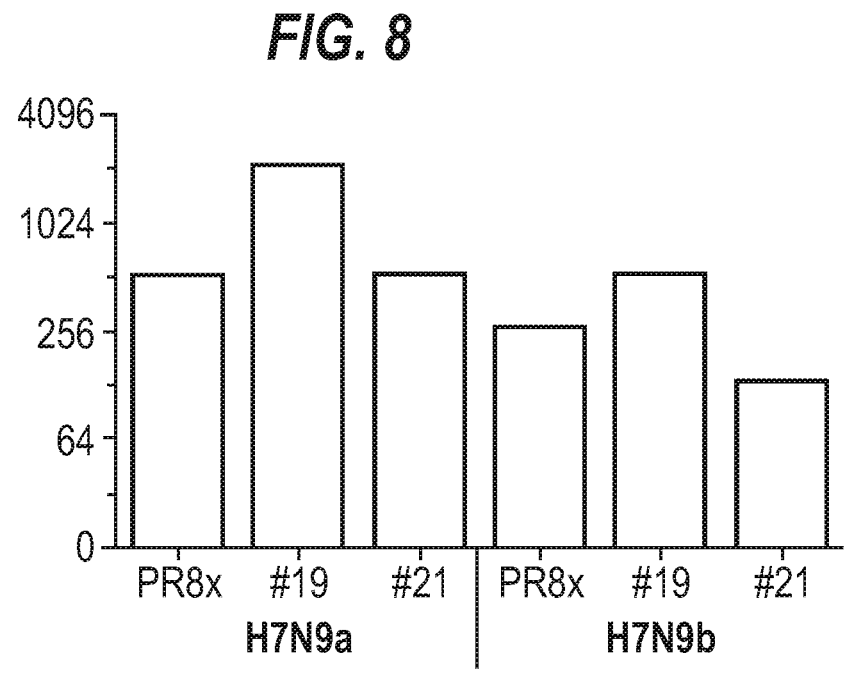

In a timed proof-of-concept test of the synthetic system's first iteration, the virus synthesis group was provided with unidentified HA and NA genome segment sequences by collaborators not directly involved in the synthesis (17). The sequences included complete coding regions but incomplete un-translated regions (UTRs), mimicking the information likely to be available in the early days of a pandemic. Sequence analysis of the HA genome segment showed that it was very dosely related (96% nucleotide sequence identity by Blast to GenBank) to a low pathogenicity North American avian H7N3 virus (A/Canada goose/BC/3752/2007), and that the NA genome segment was very closely related (96% nucleotide sequence identity by Blast to GenBank) to a low pathogenicity North American avian H10N9 virus (A/king eider/Alaska/44397-858/2008). Although our software generates the sequences of the oligonucleotides used for rescue, user intervention is needed when there are ambiguities in the available sequence data. In this case, the unknown terminal UTR sequences were generated based on sequence alignments with a limited number of related full-length H7 sequences and by comparison with consensus The A/goose/Nebraska/17097-4/2011 HA and NA genes were rescued with PR8x, #19, and #21 backbones. Virus rescue was more efficient using the #19 and #21 backbones than the PR8x backbone, based on the titers of viruses harvested 48 and 72 hours after transfection (FIG. 3*a*). To test growth characteristics, the synthetic viruses were amplified once in MDCK 33016 PF monolayers and then used to infect suspension MDCK 33016PF cultures at a multiplicity-of-infection (m.o.i.) of 0.001. Despite differences in the efficiency of virus recovery, viruses exhibited similar growth characteristics, regardless of backbone (FIG. 3*b*). The H7N9a set of viruses (C1434 positive sense NA) achieved infectious titers approximately 10-fold higher than their H7N9b counterparts (U1434 positive sense NA; FIG. 7). The viruses with the highest infectious yields also produced the most HA per volume of infected MDCK suspension culture (FIG. 3*c*). Thus, the single nucleotide substitution in the 5' NA non-coding region of the genomic RNA strongly influenced both infectious titer and HA yield (FIG. 8). The H7N9a virus with the #19 backbone produced 1.5-fold more HA than a virus with the same HA and NA in the context of the standard PR8x backbone (FIG. 3*c*). This demonstration confirmed the importance of rescuing multiple HA or NA variants with multiple backbones to increase the probability of identifying high yielding vaccine virus strains early in the vaccine seed generation process. Simultaneous rescue of multiple variants is faster and more easily accomplished using the synthetic approach than standard plasmid mutagenesis approaches. This example also indicates the importance for pandemic response of including as complete genome segment sequences as possible in genetic databases and of clearly delineating terminal sequences originating from viral genome segments from those originating from sequencing primers.

Robustness of the Synthetic Approach to Vaccine Virus Generation.

By combining gene synthesis, enzymatic error correction, optimized rescue protocols, and optimized backbones, the synthetic approach provides a robust tool to obtain influenza vaccine viruses. To date, the team has not encountered any influenza virus strain that cannot be rescued synthetically. The synthetic process has been used to generate a wide variety of influenza strains, including H1N1 (pre- and post-2009 variants), seasonal H3N2, swine origin H3N2v, B (Yamagata and Victoria lineages), attenuated H5N1, and H7N9 strains (table 3). The robustness of synthetic influenza virus recovery on MDCK cells is in striking contrast to the unreliability of conventional vaccine virus isolation using eggs, particularly for recent H3N2 strains (21).

TABLE 3

Diversity of synthetic influenza virus strains rescued.

| SEASONAL SEROTYPE A VIRUSES | Backbone | | |
|---|---|---|---|
| Source of synthetic HA NA | PR8X | #19 | #21 |
| A/H1N1/Brisbane/10/2010 | + | + | + |
| A/H1N1/Christchurch/16/2010 (NIB74) | + | + | + |
| A/H1N1/Christchurch/16/2010 NIB74-K170E | n/a | n/a | + |
| A/H1N1/Christchurch/16/2010 NIB74-K171E | n/a | n/a | + |
| A/H1N1/Christchurch/16/2010 NIB74-G172E | n/a | n/a | + |
| A/H1N1/Christchurch/16/2010 NIB74-G173D | n/a | n/a | + |
| A/H3N2/Uruguay/716/2007 | + | + | + |
| A/H3N2/Victoria/210/2009 (X187) | + | + | + |
| A/H3N2/Victoria/361/2011 (CDC E3) | + | + | + |
| A/H3N2/Victoria/361/2011 (WHO E3) | + | + | + |
| A/H3N2/Victoria/361/2011 (MDCK) | + | + | + |
| A/H3N2/Berlin/93/2011 (egg-derived) | + | + | + |
| A/H3N2/Berlin/93/2011 (cell-derived) | + | + | + |
| A/H3N2/Brisbane/402/2011 | + | + | + |
| A/H3N2/Victoria/304/2011 NVD p2/E3 | − | − | + |
| A/H3N2/Brisbane/256/2011 MDCK P2 | + | + | + |
| A/H3N2/Brisbane/256/2011 P2/E3 | − | + | + |
| A/H3N2/South Australia/34/2011 | − | + | + |
| A/H3N2/Brisbane/299/2011 (IVR164) | + | + | + |
| A/H3N2/Brisbane/299/2011 (E5) | + | + | + |
| A/H3N2/South Australia/3/2011 | + | + | + |
| A/H3N2/Wisconsin/1/2011 | + | + | + |

TABLE 3-continued

Diversity of synthetic influenza virus strains rescued.

| SEASONAL SEROTYPE B VIRUSES | Backbone | |
|---|---|---|
| Source of synthetic HA NA | Bris | #B34 |
| B/Yam/Hubei-Wujiangang/158/2009 | + | + |
| B/Yam/Wisconsin/1/2010 | + | + |
| B/Yam/Brisbane/3/2007 | + | + |
| B/Yam/Jiangsu/10/2003 | + | + |
| B/Yam/Johannesburg/05/1999 | + | + |
| B/Yam/Yamanashi/166/1998 | + | + |
| B/Yam/Yamagata/16/1998 | + | + |
| B/Yam/Texas/6/2011 | + | − |
| B/Vic/New Hampshire/1/2012 | + | + |
| B/Vic/Malaysia/2506/2004 | + | + |
| B/Vic/Brisbane/32/2002 | + | + |
| B/Vic/Brisbane/60/2008 (cell) | + | + |
| B/Vic/Brisbane/60/2008 (egg) | + | n/a |
| B/Vic/Nevada/3/2011 | + | + |

| PANDEMIC VIRUSES | Backbone | | |
|---|---|---|---|
| Source of synthetic HA NA | PR8X | #19 | #21 |
| A/H5N1/Hubei/1/2010 | + | + | + |
| A/H5N1/Egypt/N03072/2010 | + | + | + |
| A/H5N1/Turkey/Turkey/1/2005 | + | + | + |
| A/H7N9/goose/Nebraska/11-017097-4/2011 | + | + | + |
| A/H3N2v/Indiana/8/2011 | + | + | + |

n/a = not attempted;
+ = virus recovered in ≤6 days post-transfection;
− = virus not recovered by 6 days post-transfection.

Implications for the Global Strain Change and Pandemic Response Systems.

The speed, ease, and accuracy with which higher yielding influenza vaccine seeds can be produced using synthetic techniques promises more rapid future pandemic responses and a more reliable supply of better matched seasonal and pandemic influenza vaccines. The potential for propagation of adventitious agents from the human nasal secretions used for original influenza virus isolation will be eliminated when such materials are used only to generate sequence information, not for propagation into viruses used to seed vaccine production bioreactors or eggs. The speed of the technical steps of synthesis and virus rescue is actually a relatively minor component of the potential acceleration of seed generation based on synthetic technology. If the performance of synthetic vaccine viruses is sufficient, much greater time savings will result from the ability of synthetic technology to alleviate the need to ship viruses and clinical specimens between laboratories and use a classic reassortment approach to generate high-yielding vaccine strains.

Today, the more than 120 National Influenza Centers (NICs) that conduct influenza surveillance periodically ship clinical specimens to WHO Collaborating Centers, where attempts are made to propagate the wild type viruses in MDCK cells. With synthetic vaccine viruses, the system could realize increased efficiency. Sequence data obtained by directly sequencing HA and NA genomic RNAs in clinical specimens at the NICs could be posted on publically accessible websites, where they can be downloaded immediately by manufacturers, public health agencies, and other researchers worldwide. Continuous comparison of the stream of sequence data to databases of sequence and HI data by algorithms now under development could identify those emerging viruses that are most likely to have significant antigenic differences from current vaccine strains. Efficient primary synthetic rescue with a panel of high growth backbones will simultaneously generate the viruses needed for antigenic testing and the best vaccine seed candidates to be used if a virus is found to be antigenically distinct and epidemiologically important.

Today, vaccine viruses are only shipped from WHO Collaborating Centers or reassortant generating laboratories to manufacturers after they are fully tested, and testing often takes longer than the generation of the vaccine strains. The decentralization of seed generation permitted by these synthetic techniques could allow manufacturers to undertake scale up and process development at risk for strains that they could generate immediately after the NICs post sequences. Carrying out these manufacturing activities simultaneously with seed testing would cut additional weeks from pandemic response times. Libraries of synthetic influenza genes could further accelerate pandemic responses, if the pre-synthesized genes in the libraries match future pandemic strains.

Growth Characteristics of Reassortant Viruses Containing PR8-X or Canine Adapted PR8-X Backbones In order to provide high-growth donor strains, the inventors found that a reassortant influenza virus comprising the PB1 segment of A/California/07/09 and all other backbone segments from PR8-X shows improved growth characteristics compared with reassortant influenza viruses which contain all backbone segments from PR8-X. This influenza backbone is referred to as #21.

In order to test the suitability of the #21 strain as a donor strain for virus reassortment, reassortant influenza viruses are produced by reverse genetics which contain the HA and NA proteins from various influenza strains (including zoonotic, seasonal, and pandemic-like strains) and the other viral segments from either PR8-X or the #21 backbone. The HA content, HA yield and the viral titres of these reassortant viruses are determined. As a control a reference vaccine strain which does not contain any backbone segments from PR8-X or A/California/07/09 is used. These viruses are cultured either in embyronated chicken eggs or in MDCK cells.

The results indicate that reassortant viruses which contain the #21 backbone consistently give higher viral titres and HA yields compared with the control virus and the virus which contains all backbone segments from PR8-X in both eggs and cell culture. This difference is due to the PB1 segment because this is the only difference between #21 reassortants and PR8-X reassortants (see FIGS. 8 to 11).

In order to test the effect of canine-adapted mutations on the growth characteristics of PR8-X, the inventors introduce mutations into the PA segment (E327K, N444D, and N675D), or the NP segment (A27T, E375N) of PR8-X. These backbones are referred to as PR8-X(cPA) and PR8-X(cNP), respectively. Reassortant influenza viruses are produced containing the PR8-X(cPA) and PR8-X(cNP) backbones and the HA and NA segments of a pandemic-like H1 influenza strain (strain 1) or a H3 influenza strain (strain 2). As a control a reference vaccine strain which does not contain any backbone segments from PR8-X is used. The reassortant influenza viruses are cultured in MDCK cells.

Figure 9A:
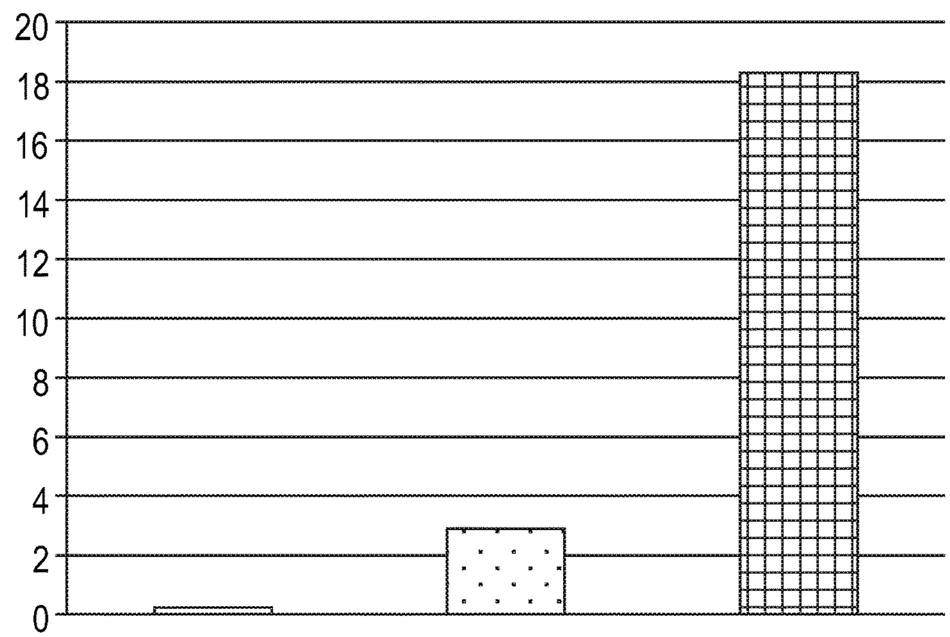
In FIGS. 9A and 9B, the black bar represents a reference vaccine strain (derived from WHO-Collaborating Centre-supplied strain) as control, the grey bar represents a reassortant virus containing the PR8-X backbone, and the white bar represents a reassortant virus containing the #21 backbone. The y-axis indicates HA yield in μg/ml.
Figure 9B:
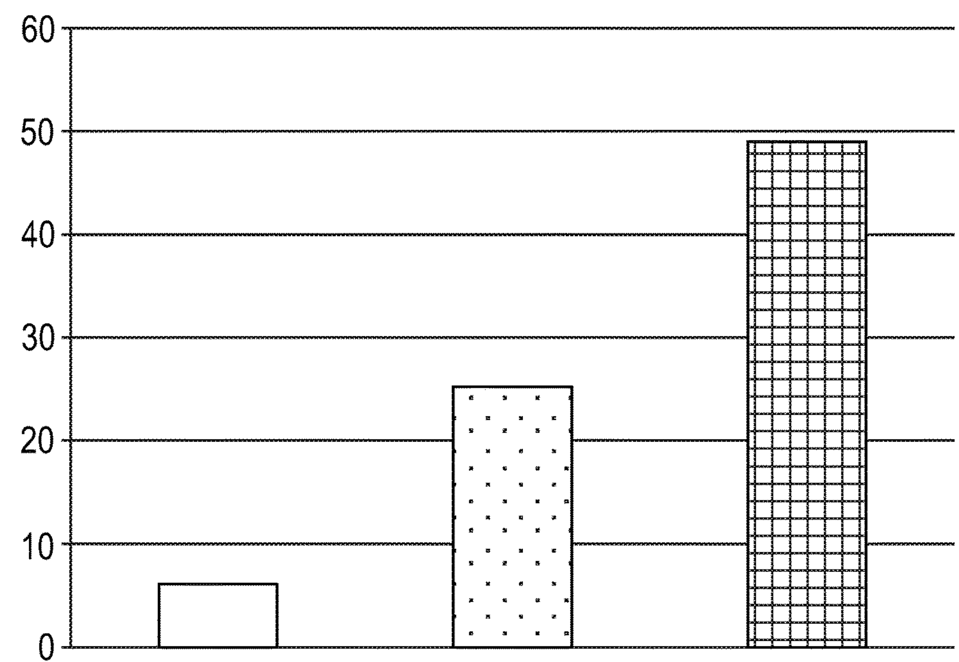
Figure 10A:
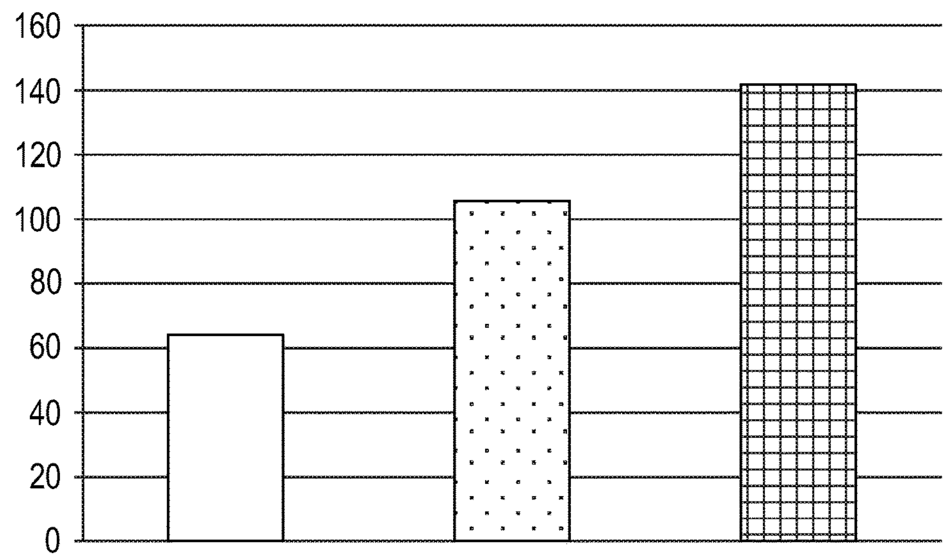
In FIGS. 10A and 10B, the black bar represents a reference vaccine strain (derived from WHO-Collaborating Centre-supplied strain) as control, the grey bar represents a reassortant virus containing the PR8-X backbone, and the white bar represents a reassortant virus containing the #21 backbone. The y-axis indicates HA yield in μg/ml.
Figure 10B:
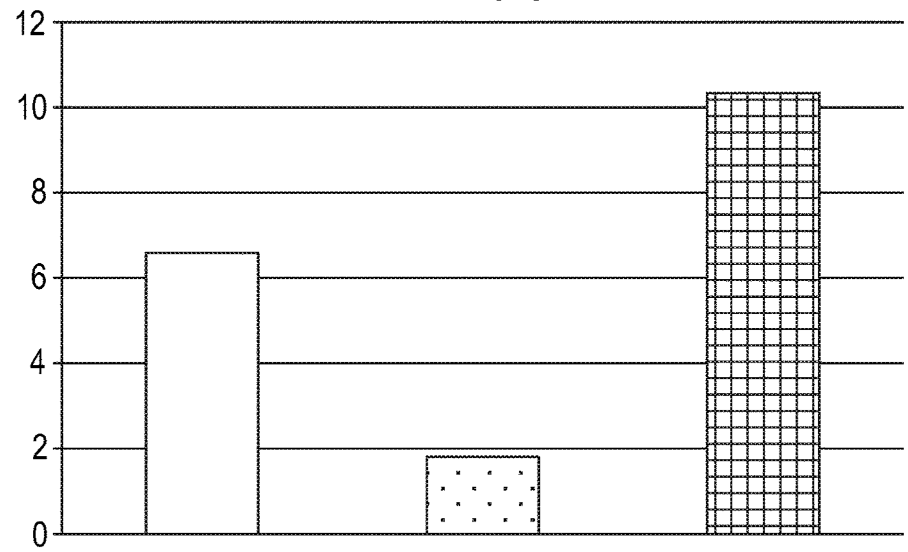
Figure 11:
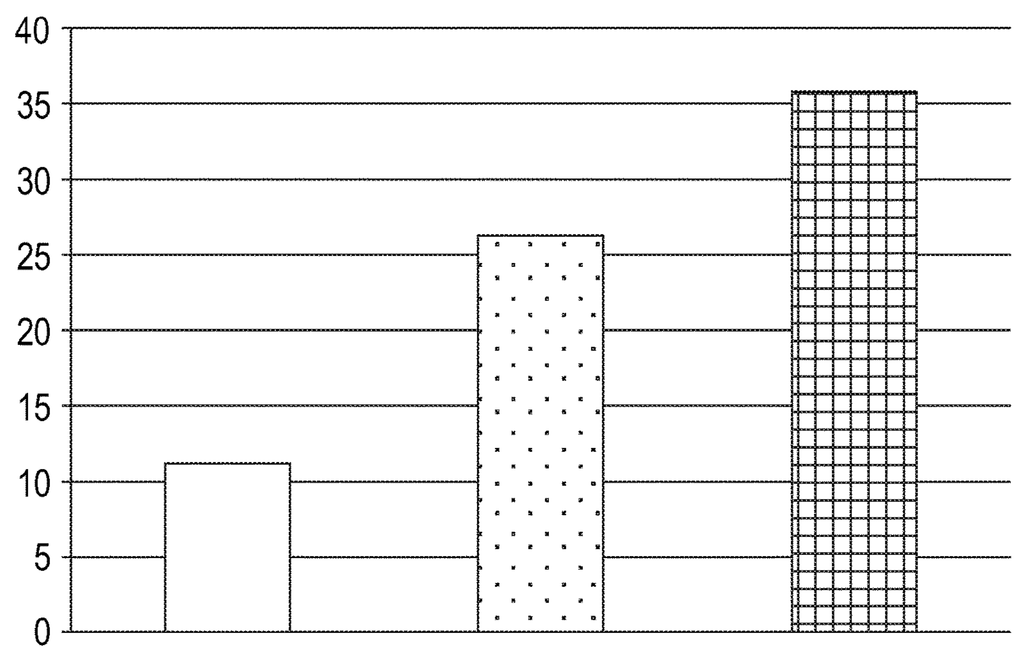
FIG. 11 compares the HA yield (determined by HPLC) of sucrose-purified viruses harvested at 60 h post-infection from MDCK cell cultures infected with reverse genetics-derived 6:2 reassortants containing either the PR8-X or #21 backbone with the HA and NA segments from an H3 strain (strain 1). The black bar represents a reference vaccine strain (derived from WHO-Collaborating Centre-supplied strain) as control, the grey bar represents a reassortant virus containing the PR8-X backbone, and the white bar represents a reassortant virus containing the #21 backbone. The y-axis indicates HA yield in μg/ml.
Figure 12A:
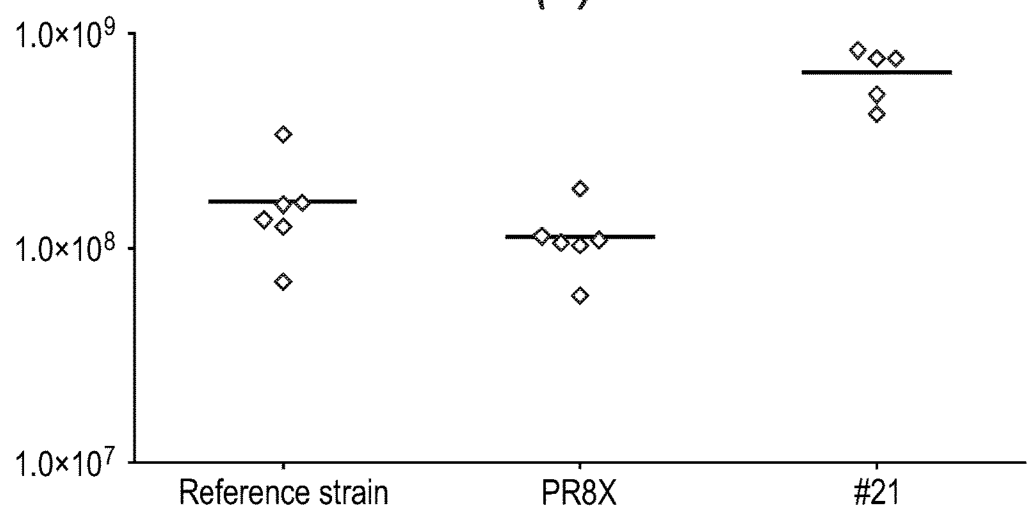
FIG. 12A) and HA titers (determined by lectin-capture ELISA.
Figure 12B:
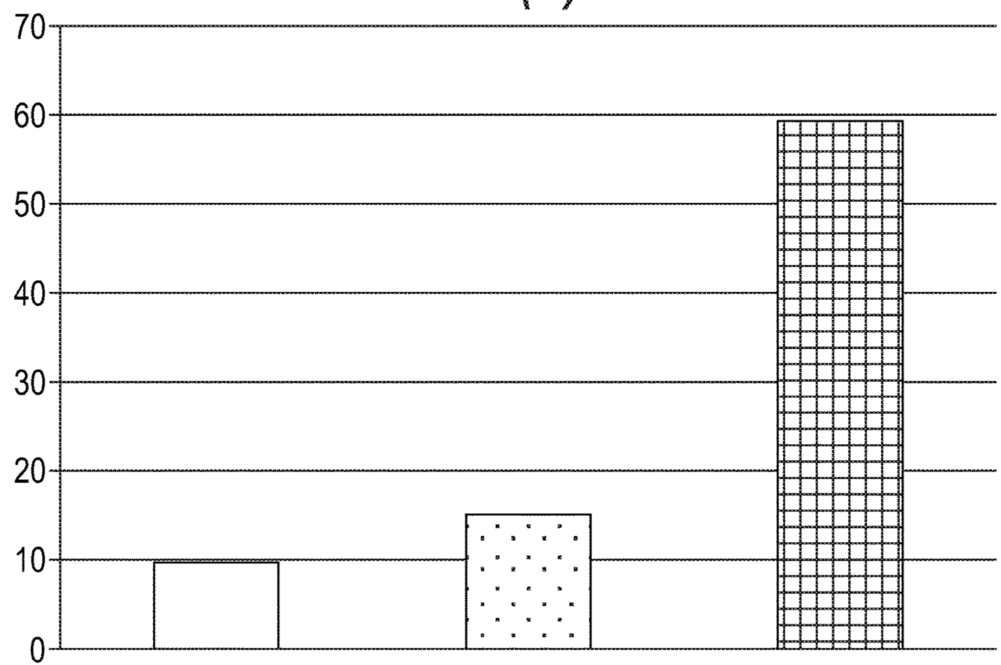
FIG. 12B) of viruses harvested from embyronated chicken eggs at 60 h post-infection with a reference vaccine strain or reverse genetics-derived 6:2 reassortant viruses made with either the PR8-X or #21 backbone and the HA and NA segments from a pandemic-like H1 strain (strain 2).

The results show that reassortant influenza viruses which contain canine-adapted backbone segments consistently grow to higher viral titres compared with reassortant influenza viruses which contain unmodified PR8-X backbone segments (see FIGS. 8 and 9).

Growth Characteristics of Reassortant Viruses Containing PR8-X, #21 or #21C Backbones In order to test whether canine-adapted mutations in the backbone segments improve the growth characteristics of the #21 backbone, the inventors modify the #21 backbone by introducing mutations into the PR8-X PB2 segment (R389K, T559N). This backbone is referred to as #21C. Reassortant influenza viruses are produced by reverse genetics which contain the HA and NA proteins from two different pandemic-like H1 strains (strains 1 and 2) and the other viral segments from either PR8-X, the #21 backbone or the #21C backbone. As a control a reference vaccine strain which does not contain any backbone segments from PR8-X or A/California/07/09 is used. These viruses are cultured in MDCK cells. The virus yield of these reassortant viruses is determined. For reassortant influenza viruses containing the HA and NA segments from the pandemic-like H1 strain (strain 1) and the PR8-X or #21C backbones the HA titres are also determined.

The results show that reassortant influenza viruses which contain the #21C backbone consistently grow to higher viral titres compared with reassortant influenza viruses which contain only PR8-X backbone segments or the #21 backbone (see FIGS. 5, 6 and 7). Reassortant influenza viruses comprising the #21C backbone also show higher HA titres compared with PR8-X reassortants.

Growth Characteristics of Reassortant Influenza B Viruses

Reassortant influenza B viruses are produced by reverse genetics which contain the HA and NA proteins from various influenza strains and the other viral segments from B/Brisbane/60/08 and/or B/Panama/45/90. As a control the corresponding wild-type influenza B strain is used. These viruses are cultured either in embyronated chicken eggs or in MDCK cells. The following influenza B strains are used:

TABLE 4

| | Backbone segments | | | | | | Antigenic determinants | |
|---|---|---|---|---|---|---|---|---|
| combo # | PA | PB1 | PB2 | NP | NS | M | HA | NA |
| 1 (WT) | Brisbane | Brisbane | Brisbane | Brisbane | Brisbane | Brisbane | Brisbane | Brisbane |
| 2 | Panama | Brisbane | Brisbane | Brisbane | Brisbane | Brisbane | Brisbane | Brisbane |
| 3 | Brisbane | Panama | Brisbane | Brisbane | Brisbane | Brisbane | Brisbane | Brisbane |
| 4 | Brisbane | Brisbane | Panama | Brisbane | Brisbane | Brisbane | Brisbane | Brisbane |
| 5 | Brisbane | Brisbane | Brisbane | Panama | Brisbane | Brisbane | Brisbane | Brisbane |
| 6 | Panama | Panama | Brisbane | Brisbane | Brisbane | Brisbane | Brisbane | Brisbane |
| 7 | Panama | Brisbane | Panama | Brisbane | Brisbane | Brisbane | Brisbane | Brisbane |
| 8 | Panama | Brisbane | Brisbane | Panama | Brisbane | Brisbane | Brisbane | Brisbane |
| 9 | Brisbane | Panama | Panama | Brisbane | Brisbane | Brisbane | Brisbane | Brisbane |
| 10 | Brisbane | Panama | Brisbane | Panama | Brisbane | Brisbane | Brisbane | Brisbane |
| 11 | Brisbane | Brisbane | Panama | Panama | Brisbane | Brisbane | Brisbane | Brisbane |
| 12 | Panama | Panama | Panama | Brisbane | Brisbane | Brisbane | Brisbane | Brisbane |
| 13 | Panama | Panama | Brisbane | Panama | Brisbane | Brisbane | Brisbane | Brisbane |
| 14 | Panama | Brisbane | Panama | Panama | Brisbane | Brisbane | Brisbane | Brisbane |
| 15 | Brisbane | Panama | Panama | Panama | Brisbane | Brisbane | Brisbane | Brisbane |
| 16 | Panama | Panama | Panama | Panama | Brisbane | Brisbane | Brisbane | Brisbane |

TABLE 4-continued

| | Backbone segments | | | | | | Antigenic determinants | |
|---|---|---|---|---|---|---|---|---|
| combo # | PA | PB1 | PB2 | NP | NS | M | HA | NA |
| 17 | Panama | Panama | Panama | Panama | Panama | Panama | Brisbane | Brisbane |
| 20 | Brisbane | Panama | Panama | Panama | Panama | Panama | Panama | Panama |
| 21 | Panama | Brisbane | Panama | Panama | Panama | Panama | Panama | Panama |
| 22 | Panama | Panama | Brisbane | Panama | Panama | Panama | Panama | Panama |
| 23 | Panama | Panama | Panama | Brisbane | Panama | Panama | Panama | Panama |
| 24 | Brisbane | Brisbane | Panama | Panama | Panama | Panama | Panama | Panama |
| 25 | Brisbane | Panama | Brisbane | Panama | Panama | Panama | Panama | Panama |
| 26 | Brisbane | Panama | Panama | Brisbane | Panama | Panama | Panama | Panama |
| 27 | Panama | Brisbane | Brisbane | Panama | Panama | Panama | Panama | Panama |
| 28 | Panama | Brisbane | Panama | Brisbane | Panama | Panama | Panama | Panama |
| 29 | Panama | Panama | Brisbane | Brisbane | Panama | Panama | Panama | Panama |
| 30 | Brisbane | Brisbane | Brisbane | Panama | Panama | Panama | Panama | Panama |
| 31 | Brisbane | Brisbane | Panama | Brisbane | Panama | Panama | Panama | Panama |
| 32 | Brisbane | Panama | Brisbane | Brisbane | Panama | Panama | Panama | Panama |
| 33 | Panama | Brisbane | Brisbane | Brisbane | Panama | Panama | Panama | Panama |
| 34 | Brisbane | Brisbane | Brisbane | Brisbane | Panama | Panama | Panama | Panama |
| 35 | Brisbane | Brisbane | Brisbane | Brisbane | Brisbane | Brisbane | Panama | Panama |

Figure 13:
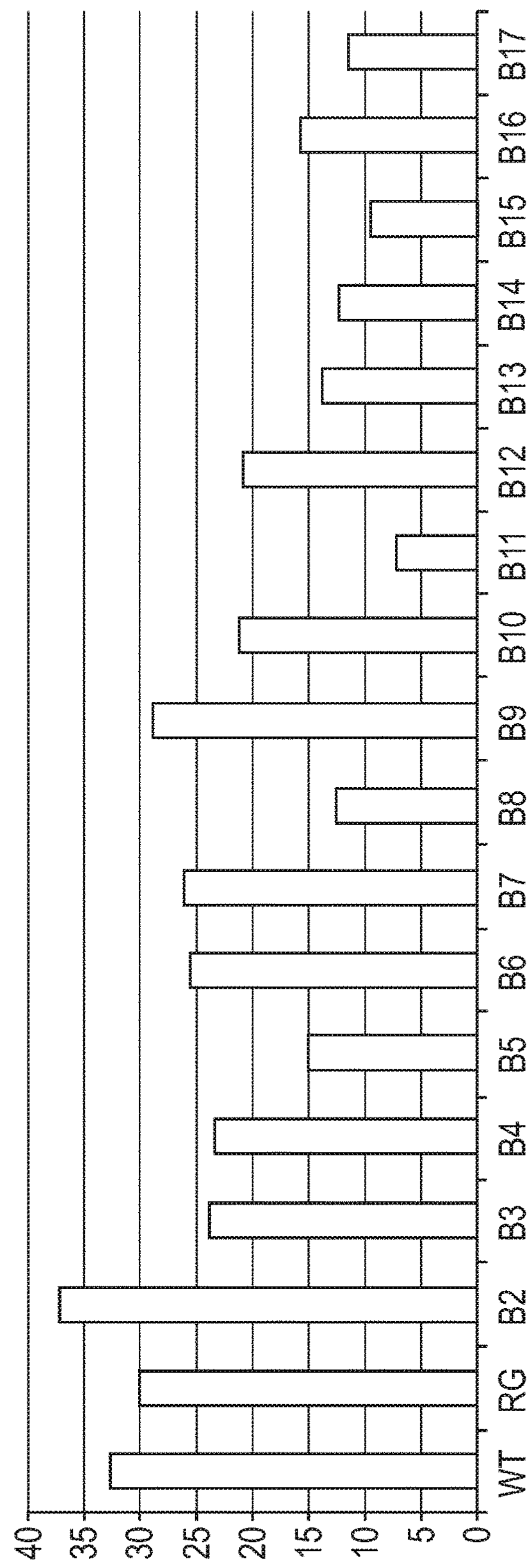
FIG. 13 compares the HA yield of different reassortant influenza B strains in MDCK cells relative to the wild-type (WT) or reverse genetics-derived (RG) B/Brisbane/60/08 strain. The viral segments of the tested influenza B viruses are shown in Table 1. The y-axis indicates the HA yield in μg/mL.
Figure 14:
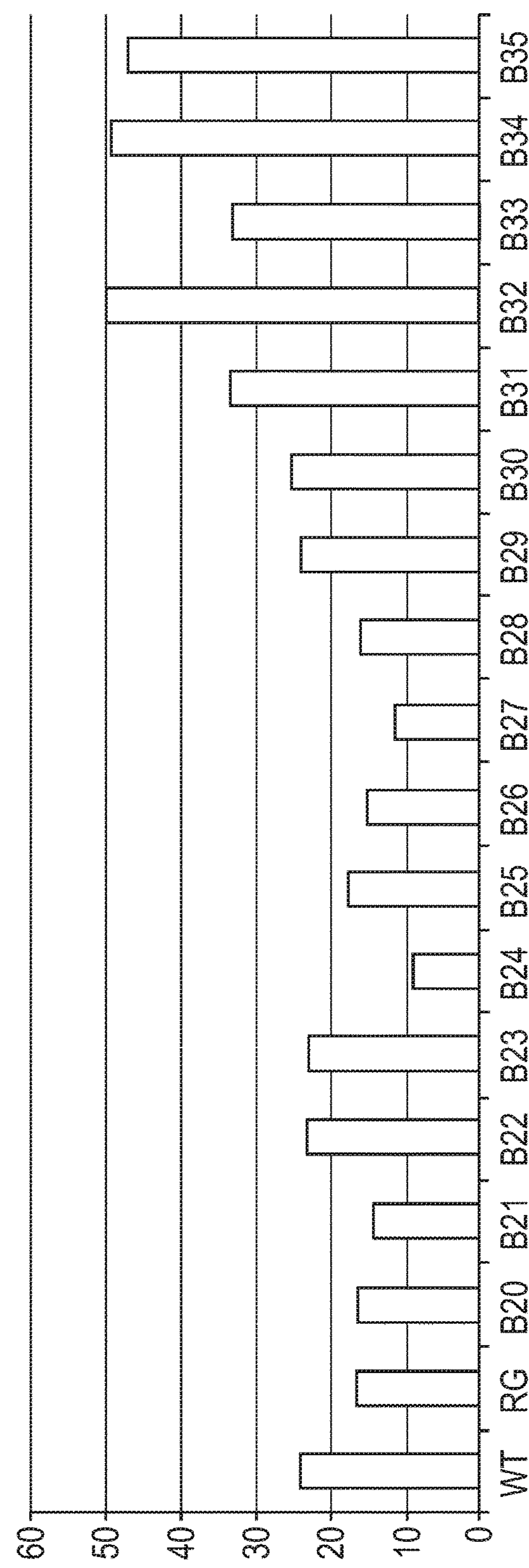
FIG. 14 compares the HA yield of different reassortant influenza B strains in MDCK cells relative to the wild-type (WT) or reverse genetics-derived (RG) B/Panama/45/90 strain. The viral segments of the tested influenza B viruses are shown in Table 1. The y-axis indicates the HA yield in μg/mL.

The results indicate that reassortant viruses #2, #9, #30, #31, #32, #33, #34 and #35 grow equally well or even better in the culture host (see FIGS. 13 and 14) than the corresponding wild-type strain. Most of these strains comprise the NP segment from B/Brisbane/60/08 and some (in particular those which grew best) further contain the PB2 segment from B/Brisbane/60/08. All of these viruses also contain viral segments from the B/Victoria/2/87-like strain and the B/Yamagata/16/88-like strain at a ratio 7:1, 6:2, 4:4, 3:4 or 1:7.

It will be understood that the invention has been described by way of example only and modifications may be made whilst remaining within the scope and spirit of the invention.

REFERENCES

[1] WO2007/002008
[2] WO2007/124327
[3] WO2011/012999
[4] Verity et al. (2012); Influenza Other Respi Viruses; 6(2):101-9.
[5] Zhou et al. (2009) J Virol.; 83(19):10309-13
[6] Gibson et at (2010); *Nature Methods* 7, 901-903.
[7] Gibson et al. (2009) *Nature Methods* 6, 343-345.
[8] U.S. Pat. No. 6,576,453
[9] Yount et al. (2002) J Virol 76:11065-78.
[10] Kodumal et al. (2004) Proc Natl Acad Sci USA. 101(44):15573-8.
[11] Yount et al. (2002) *J Virol* 76:11065-78.
[12] Sambrook et al, Molecular Cloning: A Laboratory Manual, 2 ed., 1989, Cold Spring Harbor Press, Cold Spring Harbor, N. Y
[13] WO2010/133964
[14] WO2009/000891
[15] Sambrook et al, Molecular Cloning: A Laboratory Manual, 2 ed., 1989, Cold Spring Harbor Press, Cold Spring Harbor, N. Y
[16] WO2011048560
[17] Neumann et al. (2005) Proc Natl Acad Sci USA 102: 16825-9
[18] Kistner et al. (1998) *Vaccine* 16:960-8.
[19] Kistner et al. (1999) *Dev Biol Stand* 98:101-110.
[20] Bruhl et al. (2000) Vaccine 19:1149-58.
[21] WO2006/108846.
[22] Pau et al. (2001) Vaccine 19:2716-21.
[23] http://www.atcc.org/
[24] http://locus.umdnj.edu/
[25] WO97/37000.
[26] Brands et al. (1999) Dev Biol Stand 98:93-100.
[27] Halperin et al. (2002) Vaccine 20:1240-7.
[28] EP-A-1260581 (WO01/64846).
[29] WO2006/071563.
[30] WO2005/113758.
[31] Grachev et al. (1998) Biologicals; 26(3):175-93.
[32] Herlocher et al (2004) *J Infect Dis* 190(9):1627-30.
[33] Le et al. (2005) *Nature* 437(7062):1108.
[34] Needleman & Wunsch (1970) *J Mol. Biol.* 48, 443-453.
[35] Rice et al (2000) *Trends Genet* 16:276-277.
[36] Rota et al. (1992) *J Gen Virol* 73:2737-42.
[37] GenBank sequence GI:325176.
[38] McCullers et al. (1999) *J Virol* 73:7343-8.
[39] GenBank sequence GI:325237.
[40] U.S. Pat. No. 6,468,544.
[41] WO97/37001
[42] WO02/28422.
[43] WO02/067983.
[44] WO02/074336.
[45] WO01/21151.
[46] WO02/097072.
[47] WO2005/113756.
[48] Huckriede et al. (2003) *Methods Enzymol* 373:74-91.
[49] Vaccines. (eds. Plotkins & Orenstein). 4th edition, 2004, ISBN: 0-7216-9688-0
[50] Treanor et al. (1996) *J Infect Dis* 173:1467-70.
[51] Keitel et al. (1996) *Clin Diagn Lab Immunol* 3:507-10.
[52] Herlocher et al. (2004) *J Infect Dis* 190(9):1627-30.
[53] Le et al. (2005) *Nature* 437(7062):1108.
[54] WO2008/068631.
[55] Gennaro (2000) *Remington: The Science and Practice of Pharmacy.* 20th edition, ISBN: 0683306472.
[56] Banzhoff (2000) *Immunology Letters* 71:91-96.
[57] Nony et al. (2001) *Vaccine* 27:3645-51.
[58] EP-B-0870508.
[59] U.S. Pat. No. 5,948,410.
[60] WO2007/052163.
[61] WO2007/052061
[62] WO90/14837.
[63] Podda & Del Giudice (2003) *Expert Rev Vaccines* 2:197-203.
[64] Podda (2001) *Vaccine* 19: 2673-2680.

[65] *Vaccine Design: The Subunit and Adjuvant Approach* (eds. Powell & Newman) Plenum Press 1995 (ISBN 0-306-44867-X).
[66] *Vaccine Adjuvants: Preparation Methods and Research Protocols* (Volume 42 of *Methods in Molecular Medicine* series). ISBN: 1-59259-083-7. Ed. O'Hagan.
[67] WO2008/043774.
[68] Allison & Byars (1992) *Res Immunol* 143:519-25.
[69] Hariharan et al. (1995) *Cancer Res* 55:3486-9.
[70] US-2007/014805.
[71] US-2007/0191314.
[72] Suli et al. (2004) *Vaccine* 22(25-26):3464-9.
[73] WO95/11700.
[74] U.S. Pat. No. 6,080,725.
[75] WO2005/097181.
[76] WO2006/113373.
[77] Potter & Oxford (1979) *Br Med Bull* 35: 69-75.
[78] Greenbaum et al. (2004) *Vaccine* 22:2566-77.
[79] Zurbriggen et al (2003) *Expert Rev Vaccines* 2:295-304.
[80] Piascik (2003) *J Am Pharm Assoc* (Wash D.C.). 43:728-30.
[81] Mann et al. (2004) *Vaccine* 22:2425-9.
[82] Halperin et al (1979) *Am J Public Health* 69:1247-50.
[83] Herbert et al. (1979) *J Infect Dis* 140:234-8.
[84] Chen et al. (2003) *Vaccine* 21:2830-6.
[85] *Current Protocols in Molecular Biology* (F. M. Ausubel et al., eds., 1987) Supplement 30.
[86] Smith & Waterman (1981) *Adv. Appl. Math.* 2: 482-489.
[87] Suphaphiphat et al. (2010), *Virology J.* 7, 157.
[88] Hoffmann et al. (2000) *PNAS* 97, 6108-6113.
[89] Nicolson et al. (2005) *Vaccine* 23, 2943-2952.
[90] Ozaki et al (2004) *J. Virol.* 78, 1851-1857.
[91] Boettcher et al. (2006) *J. Virol.* 80, 9896-9898.

The invention claimed is:

1. A method of preparing an influenza virus, comprising:

a) preparing a synthetic expression construct which encodes a viral segment from an influenza virus by (i) providing a sequence of at least part of a coding region of a hemagglutinin (HA) or a neuraminidase (NA) segment from an influenza virus; (ii) identifying a subtype of an influenza virus that comprises the HA or NA from which the coding region is derived; (iii) providing an untranslated region (UTR) sequence from an influenza virus with the same HA or NA subtype as the subtype identified in step (ii); and (iv) preparing a synthetic expression construct which encodes a viral segment comprising the coding sequence and the UTR;

b) introducing into a cell the synthetic expression construct prepared in step (a); and c) culturing the cell in order to produce a reassortant influenza virus from the synthetic expression construct introduced in step (b);

wherein the UTR sequence provided in step (iii) is identified by determining the consensus sequence of UTRs from viral strains with the same HA and NA subtype.

2. The method of claim 1, wherein the cell is a non-human cell or a human non-kidney cell.

3. The method of claim 1, further comprising (d) contacting a cell which is of the same cell type as the cell used in step (c) with the virus produced in step (c) to produce further reassortant influenza virus.

4. The method of claim 3, wherein the cell used in steps (c) and (d) is not a 293T cell.

5. The method of claim 3, wherein the cell used in steps (c) and (d) is a non-human cell or a human non-kidney cell.

6. The method of claim 1, wherein the synthetic expression construct comprises coding sequences for the HA and/or NA segment.

7. The method of claim 1, wherein the synthetic expression construct is linear.

8. The method of claim 1, wherein at least part of the synthetic expression construct obtained in step (a) is amplified.

9. The method of claim 1, wherein the step of preparing the synthetic expression construct comprises: (i) synthesizing a plurality of overlapping fragments of the synthetic expression construct, wherein the overlapping fragments span the complete synthetic expression construct; (ii) joining the fragments to provide a DNA molecule; (iii) melting the DNA molecule; (iv) re-annealing the DNA in the presence of an agent which excises mismatched nucleotides from the DNA molecule; and (v) amplifying the DNA to produce the synthetic expression construct.

10. The method of claim 1, wherein the reassortant influenza virus is a reassortant influenza A virus.

11. The method of claim 10, wherein the reassortant influenza A virus comprises one or more backbone segments having at least 95%, at least 96%, at least 97%, at least 98%, at least 99% or 100% identity to the sequence of SEQ ID NOs 9 to 14 or one or more backbone segments having at least 95%, at least 96%, at least 97%, at least 98%, at least 99% or 100% identity to the sequence of SEQ ID NOs 42 to 47.

12. The method of claim 10, wherein the reassortant influenza A virus comprises backbone segments from two or more influenza A strains.

13. The method of claim 10, wherein the reassortant influenza A virus comprises the PB1 segment of SEQ ID NO: 43; the PB2 segment of SEQ ID NO: 44; the PA segment of SEQ ID NO: 9; the NP segment of SEQ ID NO: 45; the M segment of SEQ ID NO: 13; and the NS segment of SEQ ID NO: 14 or the PB1 segment of SEQ ID NO: 18; the PB2 segment of SEQ ID NO: 11; the PA segment of SEQ ID NO: 9; the NP segment of SEQ ID NO: 12; the M segment of SEQ ID NO: 13; and the NS segment of SEQ ID NO: 14.

14. The method of claim 1, wherein the reassortant influenza virus is a reassortant influenza B virus.

15. The method of claim 14, wherein the reassortant influenza B virus comprises the PA segment of SEQ ID NO: 71, the PB1 segment of SEQ ID NO: 72, the PB2 segment of SEQ ID NO: 73, the NP segment of SEQ ID NO: 74, the NS segment of SEQ ID NO: 76 and the M segment of SEQ ID NO: 75 or SEQ ID NO: 81.

16. The method of claim 1, further comprising preparing an influenza vaccine, comprising the steps:

d) contacting a cell with the reassortant influenza virus prepared by the method of any preceding claim;

e) culturing the cell in order to produce an influenza virus; and f) preparing a vaccine from the influenza virus produced in step (b).

17. The method of claim 16, wherein the cell is a human non-kidney cell or a non-human cell.

18. The method of claim 16, wherein the cell used in step (d) is of the same cell type as the cell used to prepare the reassortant influenza virus.

19. The method of claim 16, wherein step (f) involves inactivating the virus.

20. The method of claim 16, wherein the vaccine is a whole virion vaccine, a split virion vaccine, a surface antigen vaccine, or a virosomal vaccine.

21. The method of claim 16, wherein the vaccine contains less than 10 ng of residual host cell DNA per dose.

22. The method of claim 1, wherein the cell is a mammalian cell or an avian cell.

23. The method of claim 22, wherein the cell is an MDCK (optionally cell line MDCK 33016 (DSM ACC2219)), Vero or PerC6 cell.

24. The method of claim 1, wherein the cell grows in suspension or adherently.

25. The method of claim 9, wherein the fragments have a length between 61 and 100 nucleotides.

26. The method of claim 25, wherein the fragments have a length between 61 and 74 nucleotides.

27. The method of claim 9, wherein the fragments have an overlap of about 40 nucleotides.

28. The method of claim 1, wherein the whole coding region of the HA or NA segment from an influenza virus is provided in step (i).

29. The method of claim 1, further comprising ranking the percent sequence identity of the virus(es) identified in step (iii) as compared to the virus of step (i) and providing the UTR from the highest ranked virus in said method.

30. The method of claim 1, wherein the consensus sequence is determined by aligning the UTRs from 2, 5, 10, 15, 20, 30 or more influenza strains with the same HA or NA subtype.

31. A reassortant influenza virus obtainable by the method of claim 1.

32. A vaccine obtainable by the method of claim 16.

33. The method of claim 23, wherein the MDCK cell comes from an MDCK 33016 cell line (DSM ACC2219).

* * * * *

```
                         SEQUENCE LISTING


<160> NUMBER OF SEQ ID NOS: 104

<210> SEQ ID NO 1
<211> LENGTH: 716
<212> TYPE: PRT
<213> ORGANISM: Influenza virus

<400> SEQUENCE: 1

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255
```

```
Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670
```

```
Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715


<210> SEQ ID NO 2
<211> LENGTH: 757
<212> TYPE: PRT
<213> ORGANISM: Influenza virus

<400> SEQUENCE: 2

Met Asp Val Asn Pro Thr Leu Leu Phe Leu Lys Val Pro Thr Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Met Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335
```

```
Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750
```

Leu Arg Arg Gln Lys
755

<210> SEQ ID NO 3
<211> LENGTH: 759
<212> TYPE: PRT
<213> ORGANISM: Influenza virus

<400> SEQUENCE: 3

Met Glu Arg Ile Lys Glu Leu Arg Asn Leu Met Ser Gln Ser Arg Thr
1 5 10 15

Arg Glu Ile Leu Thr Lys Thr Thr Val Asp His Met Ala Ile Ile Lys
20 25 30

Lys Tyr Thr Ser Gly Arg Gln Glu Lys Asn Pro Ala Leu Arg Met Lys
35 40 45

Trp Met Met Ala Met Lys Tyr Pro Ile Thr Ala Asp Lys Arg Ile Thr
50 55 60

Glu Met Ile Pro Glu Arg Asn Glu Gln Gly Gln Thr Leu Trp Ser Lys
65 70 75 80

Met Asn Asp Ala Gly Ser Asp Arg Val Met Val Ser Pro Leu Ala Val
85 90 95

Thr Trp Trp Asn Arg Asn Gly Pro Ile Thr Asn Thr Val His Tyr Pro
100 105 110

Lys Ile Tyr Lys Thr Tyr Phe Glu Arg Val Glu Arg Leu Lys His Gly
115 120 125

Thr Phe Gly Pro Val His Phe Arg Asn Gln Val Lys Ile Arg Arg Arg
130 135 140

Val Asp Ile Asn Pro Gly His Ala Asp Leu Ser Ala Lys Glu Ala Gln
145 150 155 160

Asp Val Ile Met Glu Val Val Phe Pro Asn Glu Val Gly Ala Arg Ile
165 170 175

Leu Thr Ser Glu Ser Gln Leu Thr Ile Thr Lys Glu Lys Lys Glu Glu
180 185 190

Leu Gln Asp Cys Lys Ile Ser Pro Leu Met Val Ala Tyr Met Leu Glu
195 200 205

Arg Glu Leu Val Arg Lys Thr Arg Phe Leu Pro Val Ala Gly Gly Thr
210 215 220

Ser Ser Val Tyr Ile Glu Val Leu His Leu Thr Gln Gly Thr Cys Trp
225 230 235 240

Glu Gln Met Tyr Thr Pro Gly Gly Glu Val Arg Asn Asp Asp Val Asp
245 250 255

Gln Ser Leu Ile Ile Ala Ala Arg Asn Ile Val Arg Arg Ala Ala Val
260 265 270

Ser Ala Asp Pro Leu Ala Ser Leu Leu Glu Met Cys His Ser Thr Gln
275 280 285

Ile Gly Gly Ile Arg Met Val Asp Ile Leu Arg Gln Asn Pro Thr Glu
290 295 300

Glu Gln Ala Val Asp Ile Cys Lys Ala Ala Met Gly Leu Arg Ile Ser
305 310 315 320

Ser Ser Phe Ser Phe Gly Gly Phe Thr Phe Lys Arg Thr Ser Gly Ser
325 330 335

Ser Val Lys Arg Glu Glu Glu Val Leu Thr Gly Asn Leu Gln Thr Leu
340 345 350

Lys Ile Arg Val His Glu Gly Tyr Glu Glu Phe Thr Met Val Gly Arg
355 360 365

```
Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Arg Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Ile Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 4
<211> LENGTH: 498

```
<212> TYPE: PRT
<213> ORGANISM: Influenza virus

<400> SEQUENCE: 4

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400
```

```
Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 5
<211> LENGTH: 252
<212> TYPE: PRT
<213> ORGANISM: Influenza virus

<400> SEQUENCE: 5

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 6
```

```
<211> LENGTH: 230
<212> TYPE: PRT
<213> ORGANISM: Influenza virus

<400> SEQUENCE: 6

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230


<210> SEQ ID NO 7
<211> LENGTH: 565
<212> TYPE: PRT
<213> ORGANISM: Influenza virus

<400> SEQUENCE: 7

Met Lys Ala Asn Leu Leu Val Leu Leu Cys Ala Leu Ala Ala Ala Asp
1               5                   10                  15

Ala Asp Thr Ile Cys Ile Gly Tyr His Thr Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110
```

-continued

```
Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Glu Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525
```

```
Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 8
<211> LENGTH: 454
<212> TYPE: PRT
<213> ORGANISM: Influenza virus

<400> SEQUENCE: 8

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser His Ser Ile Gln Thr Gly Ser Gln Asn His Thr Gly Ile
        35                  40                  45

Cys Asn Gln Asn Ile Ile Thr Tyr Lys Asn Ser Thr Trp Val Lys Asp
    50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
            100                 105                 110

Glu Cys Arg Thr Phe Phe Leu Thr Gln Gly Ala Leu Leu Asn Asp Lys
        115                 120                 125

His Ser Ser Gly Thr Val Lys Asp Arg Ser Pro Tyr Arg Ala Leu Met
    130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
            180                 185                 190

Tyr Asn Gly Ile Ile Thr Glu Thr Ile Lys Ser Trp Arg Lys Lys Ile
        195                 200                 205

Leu Arg Thr Gln Glu Ser Glu Cys Ala Cys Val Asn Gly Ser Cys Phe
    210                 215                 220

Thr Ile Met Thr Asp Gly Pro Ser Asp Gly Leu Ala Ser Tyr Lys Ile
225                 230                 235                 240

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Asp Thr Asp Lys
            260                 265                 270

Val Met Cys Val Cys Arg Asp Asn Trp His Gly Ser Asn Arg Pro Trp
        275                 280                 285

Val Ser Phe Asp Gln Asn Leu Asp Tyr Gln Ile Gly Tyr Ile Cys Ser
    290                 295                 300

Gly Val Phe Gly Asp Asn Pro Arg Pro Glu Asp Gly Thr Gly Ser Cys
305                 310                 315                 320

Gly Pro Val Tyr Val Asp Gly Ala Asn Gly Val Lys Gly Phe Ser Tyr
                325                 330                 335
```

```
Arg Tyr Gly Asn Gly Val Trp Ile Gly Arg Thr Lys Ser His Ser Ser
            340                 345                 350

Arg His Gly Phe Glu Met Ile Trp Asp Pro Asn Gly Trp Thr Glu Thr
        355                 360                 365

Asp Ser Lys Phe Ser Val Arg Gln Asp Val Val Ala Met Thr Asp Trp
    370                 375                 380

Ser Gly Tyr Ser Gly Ser Phe Val Gln His Pro Glu Leu Thr Gly Leu
385                 390                 395                 400

Asp Cys Met Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
            420                 425                 430

Val Asn Ser Asp Thr Val Asp Trp Ser Trp Pro Asp Gly Ala Glu Leu
        435                 440                 445

Pro Phe Ser Ile Asp Lys
    450
```

<210> SEQ ID NO 9
<211> LENGTH: 2233
<212> TYPE: DNA
<213> ORGANISM: Influenza virus

<400> SEQUENCE: 9

```
agcgaaagca ggtactgatc caaaatggaa gattttgtgc gacaatgctt caatccgatg     60

attgtcgagc ttgcggaaaa aacaatgaaa gagtatgggg aggacctgaa aatcgaaaca    120

aacaaatttg cagcaatatg cactcacttg gaagtatgct tcatgtattc agattttcac    180

ttcatcaatg agcaaggcga gtcaataatc gtagaacttg gtgatccaaa tgcacttttg    240

aagcacagat ttgaaataat cgagggaaga gatcgcacaa tggcctggac agtagtaaac    300

agtatttgca acactacagg ggctgagaaa ccaaagtttc taccagattt gtatgattac    360

aaggagaata gatttatcga aattggagta acaaggagag aagttcacat atactatctg    420

gaaaaggcca ataaaattaa atctgagaaa acacacatcc acattttctc gttcactggg    480

gaagaaatgg ccacaaaggc agactacact ctcgatgaag aaagcagggc taggatcaaa    540

accagactat tcaccataag acaagaaatg gccagcagag gcctctggga ttcctttcgt    600

cagtccgaga gaggagaaga gacaattgaa gaaaggtttg aaatcacagg aacaatgcgc    660

aagcttgccg accaaagtct cccgccgaac ttctccagcc ttgaaaattt tagagcctat    720

gtggatggat tcgaaccgaa cggctacatt gagggcaagc tgtctcaaat gtccaaagaa    780

gtaaatgcta gaattgaacc tttttgaaa acaacaccac gaccacttag acttccgaat    840

gggcctccct gttctcagcg gtccaaattc ctgctgatgg atgccttaaa attaagcatt    900

gaggacccaa gtcatgaagg agagggaata ccgctatatg atgcaatcaa atgcatgaga    960

acattctttg gatggaagga acccaatgtt gttaaaccac acgaaaaggg aataaatcca   1020

aattatcttc tgtcatggaa gcaagtactg gcagaactgc aggacattga gaatgaggag   1080

aaaattccaa agactaaaaa tatgaagaaa acaagtcagc taaagtgggc acttggtgag   1140

aacatggcac cagaaaaggt agactttgac gactgtaaag atgtaggtga tttgaagcaa   1200

tatgatagtg atgaaccaga attgaggtcg cttgcaagtt ggattcagaa tgagtttaac   1260

aaggcatgcg aactgacaga ttcaagctgg atagagctcg atgagattgg agaagatgtg   1320

gctccaattg aacacattgc aagcatgaga aggaattatt tcacatcaga ggtgtctcac   1380
```

```
tgcagagcca cagaatacat aatgaagggg gtgtacatca atactgcctt gcttaatgca   1440

tcttgtgcag caatggatga tttccaatta attccaatga taagcaagtg tagaactaag   1500

gagggaaggc gaaagaccaa cttgtatggt ttcatcataa aggaagatc ccacttaagg    1560

aatgacaccg acgtggtaaa ctttgtgagc atggagtttt ctctcactga cccaagactt   1620

gaaccacata aatgggagaa gtactgtgtt cttgagatag gagatatgct tataagaagt   1680

gccataggcc aggtttcaag gcccatgttc ttgtatgtga gaacaaatgg aacctcaaaa   1740

attaaaatga aatggggaat ggagatgagg cgttgcctcc tccagtcact tcaacaaatt   1800

gagagtatga ttgaagctga gtcctctgtc aaagagaaag acatgaccaa agagttcttt   1860

gagaacaaat cagaaacatg gcccattgga gagtccccca aaggagtgga ggaaagttcc   1920

attgggaagg tctgcaggac tttattagca aagtcggtat tcaacagctt gtatgcatct   1980

ccacaactag aaggattttc agctgaatca agaaaactgc ttcttatcgt tcaggctctt   2040

agggacaacc ttgaacctgg gacctttgat cttggggggc tatatgaagc aattgaggag   2100

tgcctgatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                      2233
```

<210> SEQ ID NO 10
<211> LENGTH: 2341
<212> TYPE: DNA
<213> ORGANISM: Influenza virus

<400> SEQUENCE: 10

```
agcgaaagca ggcaaaccat ttgaatggat gtcaatccga ccttactttt cttaaaagtg     60

ccaacacaaa atgctataag cacaactttc ccttatactg gagaccctcc ttacagccat    120

gggacaggaa caggatacac catggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaggcgatg    300

gctttccttg aggaatccca tcctggtatt tttgaaaact cgtgtattga aacgatggag    360

gttgttcagc aaacacgagt agacaagctg acacaaggcc gacagaccta tgactggact    420

ctaaatagaa accaacctgc tgcaacagca ttggccaaca caatagaagt gttcagatca    480

aatggcctca cggccaatga gtctggaagg ctcatagact tccttaagga tgtaatggag    540

tcaatgaaca aagaagaaat ggggatcaca actcattttc agagaaagag acgggtgaga    600

gacaatatga ctaagaaaat gataacacag agaacaatgg gtaaaaagaa gcagagattg    660

aacaaaagga gttatctaat tagagcattg accctgaaca caatgaccaa agatgctgag    720

agagggaagc taaaacggag agcaattgca accccaggga tgcaaataag gggtttgta     780

tactttgttg agacactggc aaggagtata tgtgagaaac ttgaacaatc agggttgcca    840

gttggaggca atgagaagaa agcaaagttg gcaaatgttg taaggaagat gatgaccaat    900

tctcaggaca ccgaactttc tttcaccatc actggagata acaccaaatg gaacgaaaat    960

cagaatcctc ggatgttttt ggccatgatc acatatatga ccagaaatca gcccgaatgg   1020

ttcagaaatg ttctaagtat tgctccaata atgttctcaa acaaaatggc gagactggga   1080

aaagggtata tgtttgagag caagagtatg aaacttagaa ctcaaatacc tgcagaaatg   1140

ctagcaagca tcgatttgaa atatttcaat gattcaacaa gaaagaagat tgaaaaaatc   1200

cgaccgctct taatagaggg gactgcatca ttgagccctg gaatgatgat gggcatgttc   1260
```

```
aatatgttaa gcactgtatt aggcgtctcc atcctgaatc ttggacaaaa gagatacacc   1320

aagactactt actggtggga tggtcttcaa tcctctgacg attttgctct gattgtgaat   1380

gcacccaatc atgaagggat tcaagccgga gtcgacaggt tttatcgaac ctgtaagcta   1440

cttggaatca atatgagcaa gaaaaagtct tacataaaca gaacaggtac atttgaattc   1500

acaagttttt tctatcgtta tgggtttgtt gccaatttca gcatggagct tcccagtttt   1560

ggggtgtctg ggatcaacga gtcagcggac atgagtattg gagttactgt catcaaaaac   1620

aatatgataa acaatgatct tggtccagca acagctcaaa tggcccttca gttgttcatc   1680

aaagattaca ggtacacgta ccgatgccat agaggtgaca cacaaataca aacccgaaga   1740

tcatttgaaa taaagaaact gtgggagcaa acccgttcca aagctggact gctggtctcc   1800

gacggaggcc caaatttata caacattaga aatctccaca ttcctgaagt ctgcctaaaa   1860

tgggaattga tggatgagga ttaccagggg cgtttatgca acccactgaa cccatttgtc   1920

agccataaag aaattgaatc aatgaacaat gcagtgatga tgccagcaca tggtccagcc   1980

aaaaacatgg agtatgatgc tgttgcaaca acacactcct ggatccccaa aagaaatcga   2040

tccatcttga atacaagtca aagaggagta cttgaggatg aacaaatgta ccaaaggtgc   2100

tgcaatttat ttgaaaaatt cttccccagc agttcataca gaagaccagt cgggatatcc   2160

agtatggtgg aggctatggt ttccagagcc cgaattgatg cacggattga tttcgaatct   2220

ggaaggataa agaaagaaga gttcactgag atcatgaaga tctgttccac cattgaagag   2280

ctcagacggc aaaaatagtg aatttagctt gtccttcatg aaaaaatgcc ttgtttctac   2340

t                                                                   2341
```

<210> SEQ ID NO 11
<211> LENGTH: 2341
<212> TYPE: DNA
<213> ORGANISM: Influenza virus

<400> SEQUENCE: 11

```
agcgaaagca ggtcaattat attcaatatg gaaagaataa aagaactaag aaatctaatg     60

tcgcagtctc gcacccgcga gatactcaca aaaaccaccg tggaccatat ggccataatc    120

aagaagtaca catcaggaag acaggagaag aacccagcac ttaggatgaa atggatgatg    180

gcaatgaaat atccaattac agcagacaag aggataacgg aaatgattcc tgagagaaat    240

gagcaaggac aaactttatg gagtaaaatg aatgatgccg gatcagaccg agtgatggta    300

tcacctctgg ctgtgacatg gtggaatagg aatggaccaa taacaaatac agttcattat    360

ccaaaaatct acaaaactta ttttgaaaga gtagaaaggc taaagcatgg aacctttggc    420

cctgtccatt ttagaaacca agtcaaaata cgtcggagag ttgacataaa tcctggtcat    480

gcagatctca gtgccaagga ggcacaggat gtaatcatgg aagttgtttt ccctaacgaa    540

gtgggagcca ggatactaac atcggaatcg caactaacga taaccaaaga gaagaaagaa    600

gaactccagg attgcaaaat ttctcctttg atggttgcat acatgttgga gagagaactg    660

gtccgcaaaa cgagattcct cccagtggct ggtggaacaa gcagtgtgta cattgaagtg    720

ttgcatttga ctcaaggaac atgctgggaa cagatgtata ctccaggagg ggaagtgagg    780

aatgatgatg ttgatcaaag cttgattatt gctgctagga acatagtgag aagagctgca    840

gtatcagcag atccactagc atctttattg gagatgtgcc acagcacaca gattggtgga    900

attaggatgg tagacatcct taggcagaac ccaacagaag agcaagccgt ggatatatgc    960
```

```
aaggctgcaa tgggactgag aattagctca tccttcagtt ttggtggatt cacatttaag   1020
agaacaagcg gatcatcagt caagagagag gaagaggtgc ttacgggaaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcagcgatt gaatcctatg   1320
catcaacttt taagacattt tcagaaggat gcgagagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagaatcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tattggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg ggccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 12
<211> LENGTH: 1565
<212> TYPE: DNA
<213> ORGANISM: Influenza virus

<400> SEQUENCE: 12

```
agcaaaagca gggtagataa tcactcactg agtgacatca aaatcatggc gtctcaaggc     60
accaaacgat cttacgaaca gatggagact gatggagaac gccagaatgc cactgaaatc    120
agagcatccg tcggaaaaat gattggtgga attggacgat tctacatcca aatgtgcacc    180
gaactcaaac tcagtgatta tgagggacgg ttgatccaaa acagcttaac aatagagaga    240
atggtgctct ctgcttttga cgaaaggaga aataaatacc ttgaagaaca tcccagtgcg    300
ggaaaagatc ctaagaaaac tggaggacct atatacagga gagtaaacgg aaagtggatg    360
agagaactca tcctttatga caaagaagaa ataaggcgaa tctggcgcca agctaataat    420
ggtgacgatg caacggctgg tctgactcac atgatgatct ggcattccaa tttgaatgat    480
gcaacttatc agaggacaag agctcttgtt cgcaccggaa tggatcccag gatgtgctct    540
ctgatgcaag gttcaactct ccctaggagg tctggagccg caggtgctgc agtcaaagga    600
gttggaacaa tggtgatgga attggtcaga atgatcaaac gtgggatcaa tgatcggaac    660
ttctggaggg gtgagaatgg acgaaaaaca agaattgctt atgaaagaat gtgcaacatt    720
```

```
ctcaaaggga aatttcaaac tgctgcacaa aaagcaatga tggatcaagt gagagagagc    780

cggaacccag ggaatgctga gttcgaagat ctcacttttc tagcacggtc tgcactcata    840

ttgagagggt cggttgctca caagtcctgc ctgcctgcct gtgtgtatgg acctgccgta    900

gccagtgggt acgactttga aagggaggga tactctctag tcggaataga ccctttcaga    960

ctgcttcaaa acagccaagt gtacagccta atcagaccaa atgagaatcc agcacacaag   1020

agtcaactgg tgtggatggc atgccattct gccgcatttg aagatctaag agtattaagc   1080

ttcatcaaag ggacgaaggt gctcccaaga gggaagcttt ccactagagg agttcaaatt   1140

gcttccaatg aaaatatgga gactatggaa tcaagtacac ttgaactgag aagcaggtac   1200

tgggccataa ggaccagaag tggaggaaac accaatcaac agagggcatc tgcgggccaa   1260

atcagcatac aacctacgtt ctcagtacag agaaatctcc cttttgacag aacaaccatt   1320

atggcagcat tcaatgggaa tacagagggg agaacatctg acatgaggac cgaaatcata   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                               1565
```

```
<210> SEQ ID NO 13
<211> LENGTH: 1027
<212> TYPE: DNA
<213> ORGANISM: Influenza virus

<400> SEQUENCE: 13

agcaaaagca ggtagatatt gaaagatgag tcttctaacc gaggtcgaaa cgtacgtact     60

ctctatcatc ccgtcaggcc ccctcaaagc cgagatcgca cagagacttg aagatgtctt    120

tgcagggaag aacaccgatc ttgaggttct catggaatgg ctaaagacaa gaccaatcct    180

gtcacctctg actaagggga ttttaggatt tgtgttcacg ctcaccgtgc ccagtgagcg    240

aggactgcag cgtagacgct ttgtccaaaa tgcccttaat gggaacgggg atccaaataa    300

catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga    480

acagattgct gactcccagc atcggtctca taggcaaatg gtgacaacaa ccaatccact    540

aatcagacat gagaacagaa tggttttagc cagcactaca gctaaggcta tggagcaaat    600

ggctggatcg agtgagcaag cagcagaggc catggaggtt gctagtcagg ctagacaaat    660

ggtgcaagcg atgagaacca ttgggactca tcctagctcc agtgctggtc tgaaaaatga    720

tcttcttgaa aatttgcagg cctatcagaa acgaatgggg gtgcagatgc aacggttcaa    780

gtgatcctct cactattgcc gcaaatatca ttgggatctt gcacttgaca ttgtggattc    840

ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                             1027

<210> SEQ ID NO 14
<211> LENGTH: 890
<212> TYPE: DNA
```

<213> ORGANISM: Influenza virus

<400> SEQUENCE: 14

```
agcaaaagca gggtgacaaa aacataatgg atccaaacac tgtgtcaagc tttcaggtag     60
attgctttct ttggcatgtc cgcaaacgag ttgcagacca agaactaggt gatgccccat    120
tccttgatcg gcttcgccga gatcagaaat ccctaagagg aaggggcagt actctcggtc    180
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaga atggaccagg cgatcatgga taagaacatc atactgaaag    420
cgaacttcag tgtgattttt gaccggctgg agactctaat attgctaagg gctttcaccg    480
aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga agataacaga gaatagtttt    780
gagcaaataa catttatgca agccttacat ctattgcttg aagtggagca agagataaga    840
actttctcgt ttcagcttat ttagtactaa aaaacaccct tgtttctact               890
```

<210> SEQ ID NO 15
<211> LENGTH: 1775
<212> TYPE: DNA
<213> ORGANISM: Influenza virus

<400> SEQUENCE: 15

```
agcaaaagca ggggaaaata aaaacaacca aaatgaaggc aaacctactg gtcctgttat     60
gtgcacttgc agctgcagat gcagacacaa tatgtatagg ctaccatacg aacaattcaa    120
ccgacactgt tgacacagta ctcgagaaga atgtgacagt gacacactct gttaacctgc    180
tcgaagacag ccacaacgga aaactatgta gattaaaagg aatagcccca ctacaattgg    240
ggaaatgtaa catcgccgga tggctcttgg gaaacccaga atgcgaccca ctgcttccag    300
tgagatcatg gtcctacatt gtagaaacac caaactctga gaatggaata tgttatccag    360
gagatttcat cgactatgag gagctgaggg agcaattgag ctcagtgtca tcattcgaaa    420
gattcgaaat atttcccaaa gaaagctcat ggcccaacca caacacaaac ggagtaacgg    480
cagcatgctc ccatgagggg aaaagcagtt tttacagaaa tttgctatgg ctgacggaga    540
aggagggctc atacccaaag ctgaaaaatt cttatgtgaa caaaaaaggg aaagaagtcc    600
ttgtactgtg gggtattcat cacccgccta acagtaagga acaacagaat ctctatcaga    660
atgaaaatgc ttatgtctct gtagtgactt caaattataa caggagattt accccggaaa    720
tagcagaaag acccaaagta agagatcaag ctgggaggat gaactattac tggaccttgc    780
taaaacccgg agacacaata atatttgagg caaatggaaa tctaatagca ccaatgtatg    840
ctttcgcact gagtagaggc tttgggtccg gcatcatcac ctcaaacgca tcaatgcatg    900
agtgtaacac gaagtgtcaa acacccctgg gagctataaa cagcagtctc ccttaccaga    960
atatacaccc agtcacaata ggagagtgcc caaaatacgt caggagtgcc aaattgagga   1020
tggttacagg actaaggaac attccgtcca ttcaatccag aggtctattt ggagccattg   1080
ccggttttat tgaaggggga tggactggaa tgatagatgg atggtatggt tatcatcatc   1140
```

```
agaatgaaca gggatcaggc tatgcagcgg atcaaaaaag cacacaaaat gccattaacg   1200

ggattacaaa caaggtgaac actgttatcg agaaaatgaa cattcaattc acagctgtgg   1260

gtaaagaatt caacaaatta gaaaaaagga tggaaaattt aaataaaaaa gttgatgatg   1320

gatttctgga catttggaca tataatgcag aattgttagt tctactggaa aatgaaagga   1380

ctctggaatt ccatgactca aatgtgaaga atctgtatga gaaagtaaaa agccaattaa   1440

agaataatgc caaagaaatc ggaaatggat gttttgagtt ctaccacaag tgtgacaatg   1500

aatgcatgga aagtgtaaga aatgggactt atgattatcc caaatattca gaagagtcaa   1560

agttgaacag ggaaaaggta gatggagtga aattggaatc aatggggatc tatcagattc   1620

tggcgatcta ctcaactgtc gccagttcac tggtgctttt ggtctccctg gggcaatca    1680

gtttctggat gtgttctaat ggatctttgc agtgcagaat atgcatctga gattagaatt   1740

tcagagatat gaggaaaaac acccttgttt ctact                              1775
```

```
<210> SEQ ID NO 16
<211> LENGTH: 1413
<212> TYPE: DNA
<213> ORGANISM: Influenza virus

<400> SEQUENCE: 16

agcaaaagca ggggtttaaa atgaatccaa atcagaaaat aataaccatt ggatcaatct     60

gtctggtagt cggactaatt agcctaatat tgcaaatagg gaatataatc tcaatatgga    120

ttagccattc aattcaaact ggaagtcaaa accatactgg aatatgcaac caaaacatca    180

ttacctataa aaatagcacc tgggtaaagg acacaacttc agtgatatta accggcaatt    240

catctctttg tcccatccgt gggtgggcta tatacagcaa agacaatagc ataagaattg    300

gttccaaagg agacgttttt gtcataagag agccctttat ttcatgttct cacttggaat    360

gcaggacctt ttttctgacc caaggtgcct tactgaatga caagcattca agtgggactg    420

ttaaggacag aagcccttat agggccttaa tgagctgccc tgtcggtgaa gctccgtccc    480

cgtacaattc aagatttgaa tcggttgctt ggtcagcaag tgcatgtcat gatggcatgg    540

gctggctaac aatcggaatt tcaggtccag ataatggagc agtggctgta ttaaaataca    600

acggcataat aactgaaacc ataaaaagtt ggaggaagaa aatattgagg acacaagagt    660

ctgaatgtgc ctgtgtaaat ggttcatgtt ttactataat gactgatggc ccgagtgatg    720

ggctggcctc gtacaaaatt ttcaagatcg aaaaggggaa ggttactaaa tcaatagagt    780

tgaatgcacc taattctcac tatgaggaat gttcctgtta ccctgatacc gacaaagtga    840

tgtgtgtgtg cagagacaat tggcatggtt cgaaccggcc atgggtgtct ttcgatcaaa    900

acctggatta tcaaatagga tacatctgca gtggggtttt cggtgacaac ccgcgtcccg    960

aagatggaac aggcagctgt ggtccagtgt atgttgatgg agcaaacgga gtaaagggat   1020

tttcatatag gtatggtaat ggtgtttgga taggaaggac caaaagtcac agttccagac   1080

atgggtttga gatgatttgg gatcctaatg gatggacaga gactgatagt aagttctctg   1140

tgaggcaaga tgttgtggca atgactgatt ggtcagggta tagcggaagt ttcgttcaac   1200

atcctgagct gacagggcta gactgtatga ggccgtgctt ctgggttgaa ttaatcaggg   1260

gacgacctaa agaaaaaaca atctggacta gtgcgagcag catttctttt tgtggcgtga   1320

atagtgatac tgtagattgg tcttggccag acggtgctga gttgccattc agcattgaca   1380

agtagtctgt tcaaaaaact ccttgtttct act                                1413
```

<210> SEQ ID NO 17
<211> LENGTH: 716
<212> TYPE: PRT
<213> ORGANISM: Influenza virus

<400> SEQUENCE: 17

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Pro
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380
```

```
Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715

<210> SEQ ID NO 18
<211> LENGTH: 757
<212> TYPE: PRT
<213> ORGANISM: Influenza virus

<400> SEQUENCE: 18

Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
```

```
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Ile Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
            340                 345                 350

Lys Gly Tyr Met Phe Glu Ser Lys Arg Met Lys Ile Arg Thr Gln Ile
        355                 360                 365

Pro Ala Glu Met Leu Ala Ser Ile Asp Leu Lys Tyr Phe Asn Glu Ser
    370                 375                 380

Thr Lys Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Ile Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460
```

```
Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Val Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Lys Val Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Asp Asp Tyr Arg Gly Arg Leu
    610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Val Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys
        755


<210> SEQ ID NO 19
<211> LENGTH: 759
<212> TYPE: PRT
<213> ORGANISM: Influenza virus

<400> SEQUENCE: 19

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Arg Tyr Pro Ile Thr Ala Asp Lys Arg Ile Met
    50                  55                  60

Asp Met Ile Pro Glu Arg Asn Glu Gln Gly Gln Thr Leu Trp Ser Lys
```

```
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Val His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Thr Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Ala Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Gly Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Val Arg Met Val Asp Ile Leu Arg Gln Asn Pro Thr Glu
    290                 295                 300

Glu Gln Ala Val Asp Ile Cys Lys Ala Ala Ile Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Ser Ile Asp Asn Val Met Gly Met Ile Gly Ile Leu
    450                 455                 460

Pro Asp Met Thr Pro Ser Thr Glu Met Ser Leu Arg Gly Ile Arg Val
465                 470                 475                 480

Ser Lys Met Gly Val Asp Glu Tyr Ser Ser Thr Glu Arg Val Val Val
                485                 490                 495
```

```
Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Thr Arg Ser Arg Tyr
            580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Leu Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 20
<211> LENGTH: 319
<212> TYPE: PRT
<213> ORGANISM: Influenza virus

<400> SEQUENCE: 20

Met Ala Ser Gln Gly Thr Lys Arg Ser Tyr Glu Gln Met Glu Thr Gly
1               5                   10                  15

Gly Glu Arg Gln Asp Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Asp Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Ile Leu Tyr Asp
```

```
            100                 105                 110

Lys Glu Glu Ile Arg Arg Val Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Ile Ala Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Val Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
    290                 295                 300

Lys Leu Leu Gln Asn Ser Gln Val Val Ser Leu Met Arg Pro Asn
305                 310                 315


<210> SEQ ID NO 21
<211> LENGTH: 252
<212> TYPE: PRT
<213> ORGANISM: Influenza virus

<400> SEQUENCE: 21

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Ser Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Ala Ala Phe
    130                 135                 140

Gly Leu Val Cys Ala Thr Cys Glu Gln Ile Ala Asp Ser Gln His Arg
145                 150                 155                 160
```

-continued

Ser His Arg Gln Met Ala Thr Thr Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Val Ala Asn Gln
195 200 205

Thr Arg Gln Met Val His Ala Met Arg Thr Ile Gly Thr His Pro Ser
210 215 220

Ser Ser Ala Gly Leu Lys Asp Asp Leu Leu Glu Asn Leu Gln Ala Tyr
225 230 235 240

Gln Lys Arg Met Gly Val Gln Met Gln Arg Phe Lys
245 250

<210> SEQ ID NO 22
<211> LENGTH: 219
<212> TYPE: PRT
<213> ORGANISM: Influenza virus

<400> SEQUENCE: 22

Met Asp Ser Asn Thr Met Ser Ser Phe Gln Val Asp Cys Phe Leu Trp
1 5 10 15

His Ile Arg Lys Arg Phe Ala Asp Asn Gly Leu Gly Asp Ala Pro Phe
20 25 30

Leu Asp Arg Leu Arg Arg Asp Gln Lys Ser Leu Lys Gly Arg Gly Asn
35 40 45

Thr Leu Gly Leu Asp Ile Glu Thr Ala Thr Leu Val Gly Lys Gln Ile
50 55 60

Val Glu Trp Ile Leu Lys Glu Glu Ser Ser Glu Thr Leu Arg Met Thr
65 70 75 80

Ile Ala Ser Val Pro Thr Ser Arg Tyr Leu Ser Asp Met Thr Leu Glu
85 90 95

Glu Met Ser Arg Asp Trp Phe Met Leu Met Pro Arg Gln Lys Ile Ile
100 105 110

Gly Pro Leu Cys Val Arg Leu Asp Gln Ala Ile Met Glu Lys Asn Ile
115 120 125

Val Leu Lys Ala Asn Phe Ser Val Ile Phe Asn Arg Leu Glu Thr Leu
130 135 140

Ile Leu Leu Arg Ala Phe Thr Glu Glu Gly Ala Ile Val Gly Glu Ile
145 150 155 160

Ser Pro Leu Pro Ser Leu Pro Gly His Thr Tyr Glu Asp Val Lys Asn
165 170 175

Ala Val Gly Val Leu Ile Gly Gly Leu Glu Trp Asn Gly Asn Thr Val
180 185 190

Arg Val Ser Glu Asn Ile Gln Arg Phe Ala Trp Arg Asn Cys Asp Glu
195 200 205

Asn Gly Arg Pro Ser Leu Pro Pro Glu Gln Lys
210 215

<210> SEQ ID NO 23
<211> LENGTH: 2151
<212> TYPE: DNA
<213> ORGANISM: Influenza virus

<400> SEQUENCE: 23
atggaagact ttgtgcgaca atgcttcaat ccaatgatcg tcgagcttgc ggaaaaggca 60
atgaaagaat atggggaaga tccgaaaatc gaaactaaca agtttgctgc aatatgcaca 120

```
catttggaag tttgtttcat gtattcggat ttccatttca tcgacgaacg gggtgaatca    180
ataattgtag aatctggtga cccgaatgca ctattgaagc accgatttga gataattgaa    240
ggaagagacc gaatcatggc ctggacagtg gtgaacagta tatgtaacac aacaggggta    300
gagaagccta aatttcttcc tgatttgtat gattacaaag agaaccggtt cattgaaatt    360
ggagtaacac ggagggaagt ccacatatat tacctagaga aagccaacaa aataaaatct    420
gagaagacac acattcacat cttttcattc actggagagg agatggccac caaagcggac    480
tacacccttg acgaagagag cagggcaaga atcaaaacta ggcttttcac tataagacaa    540
gaaatggcca gtaggagtct atgggattcc tttcgtcagt ccgaaagagg cgaagagaca    600
attgaagaaa aatttgagat tacaggaact atgcgcaagc ttgccgacca aagtctccca    660
ccgaacttcc ccagccttga aaactttaga gcctatgtag atggattcga gccgaacggc    720
tgcattgagg gcaagctttc ccaaatgtca aaagaagtga acgccaaaat tgaaccattc    780
ttgaggacga caccacgccc cctcagattg cctgatgggc ctctttgcca tcagcggtca    840
aagttcctgc tgatggatgc tctgaaatta agtattgaag acccgagtca cgagggggag    900
ggaataccac tatatgatgc aatcaaatgc atgaagacat tctttggctg gaaagagcct    960
aacatagtca aaccacatga gaaaggcata aatcccaatt acctcatggc ttggaagcag   1020
gtgctagcag agctacagga cattgaaaat gaagagaaga tcccaaggac aaagaacatg   1080
aagagaacaa gccaattgaa gtgggcactc ggtgaaaata tggcaccaga aaaagtagac   1140
tttgatgact gcaaagatgt tggagacctt aaacagtatg acagtgatga gccagagccc   1200
agatctctag caagctgggt ccaaaatgaa ttcaataagg catgtgaatt gactgattca   1260
agctggatag aacttgatga aataggagaa gatgttgccc cgattgaaca tatcgcaagc   1320
atgaggagga actattttac agcagaagtg tcccactgca gggctactga atacataatg   1380
aagggagtgt acataaatac ggccttgctc aatgcatcct gtgcagccat ggatgacttt   1440
cagctgatcc caatgataag caaatgtagg accaaagaag gaagacggaa aacaaacctg   1500
tatgggttca ttataaaagg aaggtctcat ttgagaaatg atactgatgt ggtgaacttt   1560
gtaagtatgg agttctcact cactgacccg agactggagc cacacaaatg ggaaaaatac   1620
tgtgttcttg aaataggaga catgctcttg aggactgcga taggccaagt gtcgaggccc   1680
atgttcctat atgtgagaac caatggaacc tccaagatca agatgaaatg gggcatggaa   1740
atgaggcgct gccttcttca gtctcttcag cagattgaga gcatgattga ggccgagtct   1800
tctgtcaaag agaaagacat gaccaaggaa ttctttgaaa acaaatcgga aacatggcca   1860
atcggagagt cacccagggg agtggaggaa ggctctattg ggaaagtgtg caggacctta   1920
ctggcaaaat ctgtattcaa cagtctatat gcgtctccac aacttgaggg gttttcggct   1980
gaatctagaa aattgcttct cattgttcag gcacttaggg acaacctgga acctggaacc   2040
ttcgatcttg gggggctata tgaagcaatc gaggagtgcc tgattaatga tccctgggtt   2100
ttgcttaatg catcttggtt caactccttc ctcacacatg cactgaagta g             2151
```

<210> SEQ ID NO 24
<211> LENGTH: 2341
<212> TYPE: DNA
<213> ORGANISM: Influenza virus

<400> SEQUENCE: 24

```
agcgaaagca ggcaaaccat ttgaatggat gtcaatccga ctctactttt cctaaaaatt     60
```

```
ccagcgcaaa atgccataag caccacattc ccttatactg gagatcctcc atacagccat    120
ggaacaggaa caggatacac catggacaca gtaaacagaa cacaccaata ctcagaaaag    180
ggaaagtgga cgacaaacac agagactggt gcaccccagc tcaacccgat tgatggacca    240
ctacctgagg ataatgaacc aagtgggtat gcacaaacag actgtgttct agaggctatg    300
gctttccttg aagaatccca cccaggaata tttgagaatt catgccttga aacaatggaa    360
gttgttcaac aaacaagggt agataaacta actcaaggtc gccagactta tgattggaca    420
ttaaacagaa atcaaccggc agcaactgca ttggccaaca ccatagaagt ctttagatcg    480
aatggcctaa cagctaatga gtcaggaagg ctaatagatt tcttaaagga tgtaatggaa    540
tcaatgaaca aagaggaaat agagataaca acccactttc aaagaaaaag gagagtaaga    600
gacaacatga ccaagaagat ggtcacgcaa agaacaatag ggaagaaaaa acaaagactg    660
aataagagag gctatctaat aagagcactg acattaaata cgatgaccaa agatgcagag    720
agaggcaagt taaaaagaag ggctatcgca acacctggga tgcagattag aggtttcgta    780
tactttgttg aaactttagc taggagcatt tgcgaaaagc ttgaacagtc tgggctccca    840
gtagggggca atgaaaagaa ggccaaactg gcaaatgttg tgagaaagat gatgactaat    900
tcacaagaca cagagatttc tttcacaatc actggggaca acactaagtg gaatgaaaat    960
caaaatcctc gaatgttcct ggcgatgatt acatatatca ccagaaatca acccgagtgg   1020
ttcagaaaca tcctgagcat ggcacccata atgttctcaa acaaaatggc aagactaggg   1080
aaagggtaca tgttcgagag taaaagaatg aagattcgaa cacaaatacc agcagaaatg   1140
ctagcaagca ttgacctgaa gtacttcaat gaatcaacaa agaagaaaat tgagaaaata   1200
aggcctcttc taatagatgg cacagcatca ctgagtcctg ggatgatgat gggcatgttc   1260
aacatgctaa gtacggtctt gggagtctcg atactgaatc ttggacaaaa gaaatacacc   1320
aagacaatat actggtggga tggctccaa tcatccgacg attttgctct catagtgaat    1380
gcaccaaacc atgagggaat acaagcagga gtggacagat tctacaggac ctgcaagtta   1440
gtgggaatca acatgagcaa aaagaagtcc tatataaata agacagggac atttgaattc   1500
acaagctttt tttatcgcta tggatttgtg gctaatttta gcatggagct acccagcttt   1560
ggagtgtctg gagtaaatga atcagctgac atgagtattg gagtaacagt gataaagaac   1620
aacatgataa acaatgacct tggacctgca acggcccaga tggctcttca attgttcatc   1680
aaagactaca gatacacata taggtgccat aggggagaca cacaaattca gacaagaaga   1740
tcatttgagt taaagaagct gtgggatcaa acccaatcaa aggtagggct attagtatca   1800
gatggaggac caaacttata caatatacgg aatcttcaca ttcctgaagt ctgcttaaaa   1860
tgggagctaa tggatgatga ttatcgggga agactttgta atcccctgaa tccctttgtc   1920
agtcataaag agattgattc tgtaaacaat gctgtggtaa tgccagccca tggtccagcc   1980
aaaagcatgg aatatgatgc cgttgcaact acacattcct ggattcccaa gaggaatcgt   2040
tctattctca acacaagcca aaggggaatt cttgaggatg aacagatgta ccagaagtgc   2100
tgcaatctat tcgagaaatt tttccctagc agttcatata ggagaccggt tggaatttct   2160
agcatggtgg aggccatggt gtctagggcc cggattgatg ccagggtcga cttcgagtct   2220
ggacggatca agaaagaaga gttctctgag atcatgaaga tctgttccac cattgaagaa   2280
ctcagacggc aaaaataatg aatttaactt gtccttcatg aaaaaatgcc ttgtttctac   2340
t                                                                   2341
```

```
<210> SEQ ID NO 25
<211> LENGTH: 2280
<212> TYPE: DNA
<213> ORGANISM: Influenza virus

<400> SEQUENCE: 25

atggagagaa taaaagaact gagagatcta atgtcgcagt cccgcactcg cgagatactc     60

actaagacca ctgtggacca tatggccata atcaaaaagt acacatcagg aaggcaagag    120

aagaaccccg cactcagaat gaagtggatg atggcaatga gatacccaat tacagcagac    180

aagagaataa tggacatgat tccagagagg aatgaacaag gacaaaccct ctggagcaaa    240

acaaacgatg ctggatcaga ccgagtgatg gtatcacctc tggccgtaac atggtggaat    300

aggaatggcc caacaacaag tacagttcat taccctaagg tatataaaac ttatttcgaa    360

aaggtcgaaa ggttgaaaca tggtaccttc ggccctgtcc acttcagaaa tcaagttaaa    420

ataaggagga gagttgatac aaaccctggc catgcagatc tcagtgccaa ggaggcacag    480

gatgtgatta tggaagttgt tttcccaaat gaagtggggg caagaatact gacatcagag    540

tcacagctgg caataacaaa agagaagaaa gaagagctcc aggattgtaa aattgctccc    600

ttgatggtgg cgtacatgct agaaagagaa ttggtccgta aaacaaggtt tctcccagta    660

gccggcggaa caggcagtgt ttatattgaa gtgttgcact taacccaagg gacgtgctgg    720

gagcagatgt acactccagg aggagaagtg agaaatgatg atgttgacca aagtttgatt    780

atcgctgcta gaaacatagt aagaagagca gcagtgtcag cagacccatt agcatctctc    840

ttggaaatgt gccacagcac acagattgga ggagtaagga tggtggacat ccttagacag    900

aatccaactg aggaacaagc cgtagacata tgcaaggcag caatagggtt gaggattagc    960

tcatctttca gttttggtgg gttcactttc aaaaggacaa gcggatcatc agtcaagaaa   1020

gaagaagaag tgctaacggg caacctccaa acactgaaaa taagagtaca tgaagggtat   1080

gaagaattca caatggttgg gagaagagca acagctattc tcagaaaggc aaccaggaga   1140

ttgatccagt tgatagtaag cgggagagac gagcagtcaa ttgctgaggc aataattgtg   1200

gccatggtat tctcacagga ggattgcatg atcaaggcag ttaggggcga tctgaacttt   1260

gtcaataggg caaaccagcg actgaacccc atgcaccaac tcttgaggca tttccaaaaa   1320

gatgcaaaag tgcttttcca gaactgggga attgaatcca tcgacaatgt gatgggaatg   1380

atcggaatac tgcccgacat gaccccaagc acggagatgt cgctgagagg gataagagtc   1440

agcaaaatgg gagtagatga atactccagc acggagagag tggtagtgag tattgaccga   1500

tttttaaggg ttagagatca aagagggaac gtactattgt ctcccgaaga agtcagtgaa   1560

acgcaaggaa ctgagaagtt gacaataact tattcgtcat caatgatgtg ggagatcaat   1620

ggccctgagt cagtgctagt caacacttat caatggataa tcaggaactg ggaaattgtg   1680

aaaattcaat ggtcacaaga tcccacaatg ttatacaaca aaatggaatt tgaaccattt   1740

cagtctcttg tccctaaggc aaccagaagc cggtacagtg gattcgtaag gacactgttc   1800

cagcaaatgc gggatgtgct tgggacattt gacactgtcc aaataataaa acttctcccc   1860

tttgctgctg ccccaccaga acagagtagg atgcaatttt cctcattgac tgtgaatgtg   1920

agaggatcag ggttgaggat actggtaaga ggcaattctc cagtattcaa ttacaacaag   1980

gcaaccaaac gacttacagt tcttggaaag gatgcaggtg cattgactga agatccagat   2040

gaaggcacat ctggggtgga gtctgctgtc ctgagaggat ttctcatttt gggcaaagaa   2100

gacaagagat atggcccagc attaagcatc aatgaactga gcaatcttgc aaaaggagag   2160
```

```
aaggctaatg tgctaattgg gcaaggggac gtagtgttgg taatgaaacg aaaacgggac   2220

tctagcatac ttactgacag ccagacagcg accaaaagaa ttcggatggc catcaattag   2280
```

<210> SEQ ID NO 26
<211> LENGTH: 958
<212> TYPE: DNA
<213> ORGANISM: Influenza virus

<400> SEQUENCE: 26

```
atggcgtctc aaggcaccaa acgatcatat gaacaaatgg agactggtgg ggagcgccag     60

gatgccacag aaatcagagc atctgtcgga agaatgattg gtggaatcgg gagattctac    120

atccaaatgt gcactgaact caaactcagt gattatgatg gacgactaat ccagaatagc    180

ataacaatag agaggatggt gctttctgct tttgatgaga gaagaaataa atacctagaa    240

gagcatccca gtgctgggaa ggaccctaag aaaacaggag gacccatata tagaagagta    300

gacggaaagt ggatgagaga actcatcctt tatgacaaag aagaaataag gagagtttgg    360

cgccaagcaa acaatggcga agatgcaaca gcaggtctta ctcatatcat gatttggcat    420

tccaacctga atgatgccac atatcagaga acaagagcgc ttgttcgcac cggaatggat    480

cccagaatgt gctctctaat gcaaggttca acacttccca gaaggtctgg tgccgcaggt    540

gctgcggtga aaggagttgg aacaatagca atggagttaa tcagaatgat caaacgtgga    600

atcaatgacc gaaatttctg gaggggtgaa aatggacgaa ggacaagggt tgcttatgaa    660

agaatgtgca atatcctcaa aggaaaattt caaacagctg cccagagggc aatgatggat    720

caagtaagag aaagtcgaaa cccaggaaac gctgagattg aagacctcat tttcctggca    780

cggtcagcac tcattctgag gggatcagtt gcacataaat cctgcctgcc tgcttgtgtg    840

tatgggcttg cagtagcaag tgggcatgac tttgaaaggg aagggtactc actggtcggg    900

atagacccat tcaaattact ccaaaacagc caagtggtca gcctgatgag accaaatg      958
```

<210> SEQ ID NO 27
<211> LENGTH: 982
<212> TYPE: DNA
<213> ORGANISM: Influenza virus

<400> SEQUENCE: 27

```
atgagtcttc taaccgaggt cgaaacgtac gttctttcta tcatcccgtc aggccccctc     60

aaagccgaga tcgcgcagag actggaaagt gtctttgcag gaaagaacac agatcttgag    120

gctctcatgg aatggctaaa gacaagacca atcttgtcac ctctgactaa gggaatttta    180

ggatttgtgt tcacgctcac cgtgcccagt gagcgaggac tgcagcgtag acgctttgtc    240

caaaatgccc taaatgggaa tggggacccg aacaacatgg atagagcagt taaactatac    300

aagaagctca aaagagaaat aacgttccat ggggccaagg aggtgtcact aagctattca    360

actggtgcac ttgccagttg catgggcctc atatacaaca ggatgggaac agtgaccaca    420

gaagctgctt ttggtctagt gtgtgccact tgtgaacaga ttgctgattc acagcatcgg    480

tctcacagac agatggctac taccaccaat ccactaatca ggcatgaaaa cagaatggtg    540

ctggctagca ctacggcaaa ggctatggaa cagatggctg gatcgagtga acaggcagcg    600

gaggccatgg aggttgctaa tcagactagg cagatggtac atgcaatgag aactattggg    660

actcatccta gctccagtgc tggtctgaaa gatgaccttc ttgaaaattt gcaggcctac    720

cagaagcgaa tgggagtgca gatgcagcga ttcaagtgat cctctcgtca ttgcagcaaa    780

tatcattggg atcttgcacc tgatattgtg gattactgat cgtctttttt tcaaatgtat    840
```

ttatcgtcgc tttaaatacg gtttgaaaag agggccttct acggaaggag tgcctgagtc 900
catgagggaa gaatatcaac aggaacagca gagtgctgtg gatgttgacg atggtcattt 960
tgtcaacata gagctagagt aa 982

<210> SEQ ID NO 28
<211> LENGTH: 865
<212> TYPE: DNA
<213> ORGANISM: Influenza virus

<400> SEQUENCE: 28
atggactcca acaccatgtc aagctttcag gtagactgtt tcctttggca tatccgcaag 60
cgatttgcag acaatggatt gggtgatgcc ccattccttg atcggctccg ccgagatcaa 120
aagtccttaa aaggaagagg caacaccctt ggcctcgata tcgaaacagc cactcttgtt 180
gggaaacaaa tcgtggaatg gatcttgaaa gaggaatcca gcgagacact tagaatgaca 240
attgcatctg tacctacttc gcgctacctt tctgacatga ccctcgagga aatgtcacga 300
gactggttca tgctcatgcc taggcaaaag ataataggcc ctctttgcgt gcgattggac 360
caggcgatca tggaaaagaa catagtactg aaagcgaact tcagtgtaat ctttaaccga 420
ttagagacct tgatactact aagggctttc actgaggagg gagcaatagt tggagaaatt 480
tcaccattac cttctcttcc aggacatact tatgaggatg tcaaaaatgc agttggggtc 540
ctcatcggag gacttgaatg gaatggtaac acggttcgag tctctgaaaa tatacagaga 600
ttcgcttgga gaaactgtga tgagaatggg agaccttcac tacctccaga gcagaaatga 660
aaagtggcga gagcaattgg gacagaaatt tgaggaaata aggtggttaa ttgaagaaat 720
gcggcacaga ttgaaagcga cagagaatag tttcgaacaa ataacattta tgcaagcctt 780
acaactactg cttgaagtag aacaagagat aagagctttc tcgtttcagc ttatttaatg 840
ataaaaaaca cccttgtttc tactg 865

<210> SEQ ID NO 29
<211> LENGTH: 758
<212> TYPE: PRT
<213> ORGANISM: Influenza virus

<400> SEQUENCE: 29

Met Asp Val Asn Pro Thr Leu Leu Phe Leu Lys Ile Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

Tyr Ser Glu Lys Gly Lys Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Glu
85 90 95

Glu Ser His Pro Gly Ile Phe Glu Asn Ser Cys Leu Glu Thr Met Glu
100 105 110

Val Val Gln Gln Thr Arg Val Asp Arg Leu Thr Gln Gly Arg Gln Thr
115 120 125

Tyr Asp Trp Thr Leu Asn Arg Asn Gln Pro Ala Ala Thr Ala Leu Ala
130 135 140

```
Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560
```

```
Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys Gln
        755


<210> SEQ ID NO 30
<211> LENGTH: 716
<212> TYPE: PRT
<213> ORGANISM: Influenza virus

<400> SEQUENCE: 30

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175
```

```
Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590
```

```
Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715


<210> SEQ ID NO 31
<211> LENGTH: 326
<212> TYPE: PRT
<213> ORGANISM: Influenza virus

<400> SEQUENCE: 31

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255
```

```
Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser
                325


<210> SEQ ID NO 32
<211> LENGTH: 252
<212> TYPE: PRT
<213> ORGANISM: Influenza virus

<400> SEQUENCE: 32

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 33
<211> LENGTH: 2299
<212> TYPE: DNA
<213> ORGANISM: Influenza virus

<400> SEQUENCE: 33
```

```
aatatggaaa gaataaaaga gctaaggaat ctgatgtcac aatctcgcac tcgcgagata     60
cttacaaaaa ctactgtaga ccacatggcc ataatcaaga aatacacatc aggaagacag    120
gagaaaaacc catcacttag aatgaaatgg atgatggcaa tgaaataccc aattacagca    180
gataaaagga taacggaaat gattcctgaa agaaatgagc aaggacagac attatggagt    240
aaagtgaatg atgccggatc agaccgagtg atgatatcac ccctggctgt gacatggtgg    300
aacagaaatg gaccagtggc aagtactatt cactatccaa aaatctacaa aacttacttt    360
gaaaaggttg aaaggttaaa acatggaacc tttggccctg tacactttag aaaccaagtc    420
aaaatacgcc gaagagtcga cataaatcct ggtcatgcag acctcagcgc caaggaggca    480
caggatgtaa ttatggaagt tgttttccct aatgaagtgg gagccagaat actaacatca    540
gaatcgcaat taacgataac caaggagaaa aaagaagaac tccagaattg caaaatttcc    600
cctttgatgg ttgcatacat gttagagagg gaacttgtcc gcaaaacgag atttctcccg    660
gttgctggtg gaacaagcag tgtgtacatt gaagttttgc atttaacaca ggggacatgc    720
tgggagcaga tgtacactcc aggtggggag gtgaggaatg atgatgttga tcaaagccta    780
attattgctg ctaggaacat agtgagaaga gctgcagtat cagcagatcc actagcatct    840
ttattagaaa tgtgccatag cacacagatt ggtgggacaa ggatggtgga tattctcagg    900
caaaatccaa cagaagaaca agctgtggat atatgcaaag cagcaatggg gctgagaatc    960
agttcatcct tcagttttgg cggattcaca tttaagagaa caagtggatc atcagtcaaa   1020
agggaggaag aagtgctcac gggcaatctg caaacattga agctaactgt gcatgaggga   1080
tatgaagagt tcacaatggt tgggaaaagg gcaacagcta tactcagaaa agcaaccagg   1140
agattgattc aactaatagt gagtggaaga gacgaacagt caatagtcga agcaatagtt   1200
gtagcaatgg tattctcaca agaagattgc atggtaaaag cagttagagg tgatctgaat   1260
ttcgttaata gagcgaatca gcggttgaat cccatgcatc aacttttgag acattttcag   1320
aaggatgcta aagtactttt cttaaattgg ggaattgaac ctatcgacaa tgtgatggga   1380
atgattggga tattacctga tatgactcca agtaccgaga tgtcaatgag aggagtgaga   1440
gtcagcaaaa tgggtgtaga tgaatactcc aatgctgaaa gggtagtggt gagcattgac   1500
cgtttttga gagtccggga ccaaagagga aatgtactac tgtctccaga ggaagtcagt   1560
gaaacacagg gaacagagaa actgacaata acttactctt catcaatgat gtgggagatt   1620
aatggccctg agtcagtgtt gatcaatacc tatcagtgga tcatcagaaa ctgggagact   1680
gttaaaattc agtggtctca gaaccctaca atgctataca ataaaatgga attcgagcca   1740
tttcagtctc tagtccctaa ggccattaga ggccaataca gtgggtttgt tagaactcta   1800
tttcaacaaa tgagggatgt gcttgggacc tttgacacaa ctcagataat aaaacttctt   1860
ccctttgcag ccgctccacc aaagcaaagt agaatgcaat tctcatcatt gactgtgaat   1920
gtgaggggat caggaatgag aatacttgta aggggtaatt ctccagtatt caactacaac   1980
aagaccacta agagactcac agtcctcgga aaggatgctg gcactttaac tgaagaccca   2040
gatgaaggca cagctggagt ggaatctgct gttctaaggg gattcctcat tctaggcaaa   2100
gaagatagaa gatatgggcc agcattaagc atcaatgaat tgagcaacct tgcgaaaggg   2160
gaaaaagcta atgtgctaat tgggcaaggg gacgtagtgt tggtaatgaa acgaaaacgg   2220
gactctagca tacttactga cagccagaca gcgaccaaaa gaattcggat ggccatcaat   2280
taatttcgaa taatttaaa                                                2299
```

<210> SEQ ID NO 34
<211> LENGTH: 2277
<212> TYPE: DNA
<213> ORGANISM: Influenza virus

<400> SEQUENCE: 34

```
atggaacgca ttaaagaact gcgcaacctg atgagccaga gccgcacccg cgaaattctg     60
accaaaacca ccgtggatca tatggcgatt attaaaaaat ataccagcgg ccgccaggaa    120
aaaaacccga gcctgcgcat gaaatggatg atggcgatga aatatccgat taccgcggat    180
aaacgcatta ccgaaatgat tccggaacgc aacgaacagg gccagaccct gtggagcaaa    240
gtgaacgatg cgggcagcga tcgcgtgatg attagcccgc tggcggtgac ctggtggaac    300
cgcaacggcc cggtggcgag caccattcat tatccgaaaa tttataaaac ctattttgaa    360
aaagtggaac gcctgaaaca tggcaccttt ggcccggtgc attttcgcaa ccaggtgaaa    420
attcgccgcc gcgtggatat taacccgggc catgcggatc tgagcgcgaa agaagcgcag    480
gatgtgatta tggaagtggt gtttccgaac gaagtgggcg cgcgcattct gaccagcgaa    540
agccagctga ccattaccaa agaaaaaaaa gaagaactgc agaactgcaa aattagcccg    600
ctgatggtgg cgtatatgct ggaacgcgaa ctggtgcgca aaacccgctt tctgccggtg    660
gcgggcggca ccagcagcgt gtatattgaa gtgctgcatc tgacccaggg cacctgctgg    720
gaacagatgt ataccccggg cggcgaagtg cgcaacgatg atgtggatca gagcctgatt    780
attgcggcgc gcaacattgt gcgccgcgcg gcggtgagcg cggatccgct ggcgagcctg    840
ctggaaatgt gccatagcac ccagattggc ggcacccgca tggtggatat tctgcgccag    900
aacccgaccg aagaacaggc ggtggatatt tgcaaagcgg cgatgggcct gcgcattagc    960
agcagcttta gctttggcgg ctttaccttt aaacgcacca gcggcagcag cgtgaaacgc   1020
gaagaagaag tgctgaccgg caacctgcag accctgaaac tgaccgtgca tgaaggctat   1080
gaagaattta ccatggtggg caaacgcgcg accgcgattc tgcgcaaagc gacccgccgc   1140
ctgattcagc tgattgtgag cggccgcgat gaacagagca ttgtggaagc gattgtggtg   1200
gcgatggtgt ttagccagga agattgcatg gtgaaagcgg tgcgcggcga tctgaacttt   1260
gtgaaccgcg cgaaccagcg cctgaacccg atgcatcagc tgctgcgcca ttttcagaaa   1320
gatgcgaaag tgctgtttct gaactggggc attgaaccga ttgataacgt gatgggcatg   1380
attggcattc tgccggatat gaccccgagc accgaaatga gcatgcgcgg cgtgcgcgtg   1440
agcaaaatgg gcgtggatga atatagcaac gcggaacgcg tggtggtgag cattgatcgc   1500
tttctgcgcg tgcgcgatca gcgcggcaac gtgctgctga gcccggaaga agtgagcgaa   1560
acccagggca ccgaaaaact gaccattacc tatagcagca gcatgatgtg ggaaattaac   1620
ggcccggaaa gcgtgctgat taacacctat cagtggatta ttcgcaactg ggaaaccgtg   1680
aaaattcagt ggagccagaa cccgaccatg ctgtataaca aaatggaatt tgaaccgttt   1740
cagagcctgg tgccgaaagc gattcgcggc cagtatagcg gctttgtgcg caccctgttt   1800
cagcagatgc gcgatgtgct gggcaccttt gataccaccc agattattaa actgctgccg   1860
tttgcggcgg cgccgccgaa acagagccgc atgcagttta gcagcctgac cgtgaacgtg   1920
cgcggcagcg gcatgcgcat tctggtgcgc ggcaacagcc cggtgtttaa ctataacaaa   1980
accaccaaac gcctgaccgt gctgggcaaa gatgcgggca ccctgaccga agatccggat   2040
gaaggcaccg cgggcgtgga aagcgcggtg ctgcgcggct ttctgattct gggcaaagaa   2100
gatcgccgct atggcccggc gctgagcatt aacgaactga gcaacctggc gaaaggcgaa   2160
```

aaagcgaacg tgctgattgg ccagggcgat gtggtgctgg tgatgaaacg caaacgcgat 2220
agcagcattc tgaccgatag ccagaccgcg accaaacgca ttcgcatggc gattaac 2277

<210> SEQ ID NO 35
<211> LENGTH: 2201
<212> TYPE: DNA
<213> ORGANISM: Influenza virus

<400> SEQUENCE: 35
gattcgaaat ggaagatttt gtgcgacaat gcttcaatcc gatgattgtc gagcttgcgg 60
aaaaggcaat gaaagagtat ggagaggacc tgaaaatcga aacaaacaaa tttgcagcaa 120
tatgcactca cttggaagta tgcttcatgt attcagattt tcatttcatc aatgagcaag 180
gcgaatcaat aatagtagag cctgaggacc caaatgcact tttaaagcac agatttgaga 240
taatagaggg acgagatcgt acaatggcat ggacagttgt aaacagtatt tgcaacacca 300
caggagctga gaaaccaaag tttctgccag atctgtatga ttacaaagag aatagattca 360
tcgagattgg agtgacaagg agggaagttc acatatacta tctggaaaag gccaacaaaa 420
ttaaatctga gaagacacac attcacattt tctcattcac tggcgaagaa atggccacaa 480
aggccgatta cactctcgat gaagaaagca gggctaggat taaaaccaga ctattcacca 540
taagacaaga aatggcaagc agaggtcttt gggactcctt tcgtcagtcc gaaagaggcg 600
aagaaacaat tgaagaaaga tttgaaatca cagggacaat gcgcaggctc gctgaccaaa 660
gccttccgcc gaacttctcc tgcattgaga attttagagc ctatgtggat ggatttgaac 720
cgaacggcta cattgagggc aagctttctc aaatgtccaa agaagtaaat gctagaattg 780
agcctttttt gaaaacaaca ccacgaccaa ttagacttcc ggatgggcct ccttgttttc 840
agcggtcaaa attcctgctg atggattctt taaaattaag cattgaggat ccaaatcatg 900
aaggagaggg aataccacta tatgatgcaa tcaagtgtat gagaacattc tttggatgga 960
aagaaccctc tgttgtcaag ccacacggga agggaataaa tccgaattat ctgctgtcat 1020
ggaagcaggt attggaagag ctgcaggaca ttgagagtga ggagaagatt ccaagaacaa 1080
aaaacatgaa aaaaacgagt cagctaaagt gggcacttgg tgagaacatg gcaccagaga 1140
aggtggattt tgatgactgt aaagatataa gcgatttgaa gcaatatgat agtgacgaac 1200
ctgaattaag gtcattttca agttggatcc agaatgagtt caacaaggca tgcgagctga 1260
ccgattcaat ctggatagag ctcgatgaga ttggagaaga tgtggccccg attgaacaca 1320
ttgcaagcat gagaagaaat tacttcacag ctgaggtgtc ccattgcaga gccacagaat 1380
atataatgaa gggggtatac attaatactg ctttgcttaa tgcatcctgt gcagcaatgg 1440
atgatttcca actaattccc atgataagca aatgtagaac taaagaggga aggagaaaga 1500
ccaatttgta cggcttcatc gtaaaaggaa gatctcactt aaggaatgac accgatgtgg 1560
taaactttgt gagcatggag ttttccctca ctgacccaag acttgagcca cacaaatggg 1620
agaagtactg tgttcttgag ataggagata tgcttctaag gagtgcaata ggccaagtgt 1680
caaggcccat gttcttgtat gtaaggacaa atggaacctc aaaaattaaa atgaaatggg 1740
gaatggagat gaggcgttgc ctcctccaat cccttcaaca aatagagagc atgattgaag 1800
ctgagtcctc cgtcaaggag aaagacatga caaaagagtt ttttgagaat agatcagaaa 1860
catggcccat tggagagtca cccaaaggag tggaagaagg ttccattggg aaagtatgca 1920
ggacactatt ggctaagtca gtattcaata gtctgtatgc atctccacaa ttagaaggat 1980

```
tttcagctga gtcaagaaag ttgctcctca ttgttcaggc tcttagggac aatctggaac   2040

ctgggacctt tgatcttggg ggctatatg aagcaattga ggagtgcctg attaatgatc   2100

cctgggtttt gcttaatgct tcttggttca actccttcct aacacatgca ttgagatagc   2160

tggggcaatg ctactattta ctatccatac tgtccaaaaa a                        2201
```

<210> SEQ ID NO 36
<211> LENGTH: 2301
<212> TYPE: DNA
<213> ORGANISM: Influenza virus

<400> SEQUENCE: 36

```
aatggatgtc aatccgacat tacttttctt aaaagtgcca gcacaaaatg ctataagcac     60

aacttttcct tatactggtg accctcctta cagccatggg acaggaacag ggtacaccat    120

ggatacagtc aacaggacac atcagtactc agaaagagga agatggacaa aaaataccga    180

aactggagca ccgcaactca acccaattga tgggccacta ccaaaagaca atgaaccaag    240

tggctatgcc caaacagatt gtgtattaga agcaatggct ttccttgagg aatcccatcc    300

tggtattttt gaaaactctt gtattgaaac aatggaggtt gttcagcaaa caagggtgga    360

caaactgaca caaggcagac agacctatga ctggactcta aataggaacc agcctgctgc    420

cacagcattg gccaacacta tagaagtgtt cagatcaaac ggcctcatag caaatgaatc    480

tgggaggcta atagacttcc ttaaagatgt aatggagtcg atggacagag acgaagtaga    540

gatcacaact cattttcaaa gaaagaggag agtgagagac aatgtaacta aaaaaatggt    600

gacccaaaga acaataggca aaaagaaaca taaattagac aaaagaagtt acctaattag    660

ggcattaacc ctgaacacaa tgaccaaaga tgctgagagg gggaaactaa aacgcagagc    720

aattgcaacc ccaggaatgc aaataagggg gtttgtatac tttgttgaga cactggcaag    780

aagcatatgt gaaaagcttg aacaatcagg gttgccagtt ggaggaaatg aaaagaaagc    840

aaagttagca aatgttgtaa ggaagatgat gaccaactcc caggacactg aaatttcttt    900

caccatcact ggagataaca caaaatggaa cgaaaatcaa aaccctagaa tgttcttggc    960

catgatcaca tatataacca aaaatcagcc tgaatggttc agaaatattc taagtattgc   1020

tccaataatg ttttcaaaca aaatggcgag actaggtaag ggtacatgt ttgaaagcaa   1080

gagtatgaaa ctgagaactc aaatacctgc agagatgcta gccaacatag atttgaaata   1140

tttcaatgat tcaactaaaa agaaaattga aaaaatccgg ccattattaa tagatggaac   1200

tgcatcattg agtcctggaa tgatgatggg catgttcaat atgttaagca ccgtcttggg   1260

cgtctccatt ctgaatcttg ggcaaaagag atacaccaag actacttact ggtgggatgg   1320

tcttcaatcg tctgatgatt ttgctctgat tgtgaatgca cccaactatg caggaattca   1380

agctggagtt gacaggtttt atcgaacctg taagctgctc ggaattaata tgagcaaaaa   1440

gaagtcttac ataaacagaa caggtacctt tgagttcacg agctttttct atcgttatgg   1500

gtttgttgcc aatttcagca tggagcttcc tagttttggg gtgtctgggg tcaatgaatc   1560

tgcagacatg agtattggag tcactgtcat caaaaacaat atgataaaca atgaccttgg   1620

cccagcaact gctcaaatgg cccttcagtt atttataaaa gattacaggt acacgtatcg   1680

atgccacaga ggtgacacac aaatacaaac ccggagatca tttgagataa agaaactatg   1740

ggaccaaacc cgctccaaag ctgggctgtt ggtctctgat ggaggcccca atttatataa   1800

cattagaaat ctccatattc ctgaagtctg cttgaaatgg gagttgatgg atgaggatta   1860

ccaggggcgt ttatgcaacc cattgaaccc gtttgtcagt cataaagaga ttgaatcagt   1920
```

```
gaacaatgca gtgatgatgc cggcacatgg tccagccaaa aatatggagt atgacgctgt   1980

tgcaacaaca cactcctggg ttcccaaaag gaatcgatcc attttgaata cgagccaaag   2040

ggggatactt gaggatgagc aaatgtatca gaggtgctgc aatttatttg aaaaattctt   2100

cccaagtagc tcatacagaa gaccagttgg aatatccagt atggtagagg ctatggtttc   2160

cagagcccga attgatgcac ggattgattt cgaatctgga aggataaaaa aagaggaatt   2220

cgctgagatc atgaagacct gttccaccat tgaagacctc agacggcaaa aatagggaat   2280

ttggcttgtc cttcatgaaa a                                             2301
```

<210> SEQ ID NO 37
<211> LENGTH: 1527
<212> TYPE: DNA
<213> ORGANISM: Influenza virus

<400> SEQUENCE: 37

```
atcactcact gagtgacatc aaagtcatgg cgtcccaagg caccaaacgg tcttacgaac     60

agatggagac tgatggggaa cgccagaatg caactgaaat cagagcatcc gtcggaagaa    120

tgattggtgg aattgggcga ttctacatcc aaatgtgcac cgagcttaaa ctcaatgatt    180

atgagggacg actgatccag aacagcttga caatagagag aatggtgctc tctgcttttg    240

atgagaggag gaataaatat ctggaagaac atcccagcgc ggggaaagat cctaagaaaa    300

ctggaggacc catatacaag agagtagatg gaaagtgggt gagggaactc gtcctttatg    360

acaaagaaga aataaggcgg atttggcgcc aagccaacaa tggtgatgat gcaacggctg    420

gtttgactca cattatgatc tggcattcta atttgaatga tacaacttac cagaggacaa    480

gagctcttgt ccgcaccgga atggatccca ggatgtgctc tttgatgcaa ggttcaactc    540

tccctagaag atctggagca gcaggcgctg cagtcaaagg agttgggaca atggtgttgg    600

agttaatcag gatgatcaaa cgtgggatca atgaccgaaa cttctggagg ggtgagaatg    660

gaagaaaaac aaggattgct tatgagagaa tgtgcaacat tctcaaagga aaatttcaaa    720

cagctgcaca aaaagcaatg atggatcaag tgagagaaag ccggaaccca ggaaatgctg    780

agatcgaaga tctcactttt ctggcacggt ctgcactcat attaagaggg tcagttgctc    840

acaagtcttg cctgcctgcc tgtgtgtatg gaccagccgt agccagtggg tacgacttcg    900

aaaaagaggg atactctttg gtaggggtag accctttttaa actgcttcaa accagtcagg    960

tatacagcct aatcagacca aacgagaatc ccgcacacaa gagtcagttg gtgtggatgg   1020

catgcaattc tgctgcattt gaagatctaa gagtgtcaag cttcatcaga gggacaagag   1080

tacttccaag gggggaagctc tccactagag gagtacaaat tgcttcaaat gaaaacatgg  1140

atgctattgt atcaagtact cttgaactga gaagcagata ctgggccata agaaccagaa   1200

gtggagggaa cactaatcaa caaagggcct ctgcgggcca aatcagcaca caacctacgt   1260

tttctgtgca gagaaacctc ccatttgaca aaacaaccat catggcagca ttcactggga   1320

atacggaggg aagaacatca gacatgaggg cagaaatcat aaagatgatg gaaagtgcaa   1380

gaccagaaga agtgtccttc caggggcggg gagtctttga gctctcggac gaaagggcaa   1440

cgaacccgat cgtgccctcc tttgacatga gtaatgaagg atcttatttc ttcggagaca   1500

atgcagagga gtacgacaat taatgaa                                       1527
```

<210> SEQ ID NO 38
<211> LENGTH: 984
<212> TYPE: DNA

<213> ORGANISM: Influenza virus

<400> SEQUENCE: 38

```
gatgagtctt ctaaccgagg tcgaaacgta cgttctctct atcgtcccgt caggccccct     60
caaagccgag atcgcacaga gacttgaaaa tgtctttgct ggaaagaata ccgatcttga    120
ggctctcatg gaatggctaa agacaagacc aatcctgtca cctctgacta aggggatttt    180
aggatttgtg ttcacgctca ccgtgcccag tgagcgagga ctgcagcgta gacgctttgt    240
ccaaaatgcc cttaatggga atggggatcc aaataatatg gacagagcag ttaaactgta    300
tcgaaagctt aagagggaga taacattcca tggggccaaa gaaatagcac tcagttattc    360
tgctggtgca cttgccagtt gtatgggact catatacaac aggatggggg ctgtgaccac    420
cgaatcagca tttggcctta tatgcgcaac ctgtgaacag attgccgact cccagcataa    480
gtctcatagg caaatggtaa caacaaccaa cccattaata agacatgaga acagaatggt    540
tctggccagc actacagcta aggctatgga gcaaatggct ggatcgagtg aacaagcagc    600
tgaggccatg gaggttgcta gtcaggccag gcagatggtg caggcaatga gagccattgg    660
gactcatcct agctctagca ctggtctgaa aaatgatctc cttgaaaatt tgcaggccta    720
tcagaaacga atgggggtgc agatgcaacg attcaagtga tcctcttgtt gttgccgcaa    780
gtataattgg gattgtgcac ctgatattgt ggattattga tcgccttttt tccaaaagca    840
tttatcgtat ctttaaacac ggtttaaaaa gagggccttc tacggaagga gtaccagagt    900
ctatgaggga agaatatcga gaggaacagc agaatgctgt ggatgctgac gatggtcatt    960
ttgtcagcat agagctagag taaa                                          984
```

<210> SEQ ID NO 39
<211> LENGTH: 844
<212> TYPE: DNA
<213> ORGANISM: Influenza virus

<400> SEQUENCE: 39

```
atggattccc acactgtgtc aagctttcag gtagattgct tcctttggca tgtccgcaaa     60
caagttgcag accaagatct aggcgatgcc ccattccttg atcggcttcg ccgagatcag    120
aagtctctaa agggaagagg cagcactctc ggtctgaaca tcgaaacagc cacttgtgtt    180
ggaaagcaaa tagtagagag gattctgaaa gaagaatccg atgaggcatt taaaatgacc    240
atggcctccg cacttgcttc gcggtaccta actgacatga ctattgaaga aatgtcaagg    300
gactggttca tgctcatgcc caagcagaaa gtggctggcc ctctttgtgt cagaatggac    360
caggcgataa tggataagaa catcatactg aaagcgaatt tcagtgtgat ttttgaccgg    420
ttggagaatc tgacattact aagggctttc accgaagagg gagcaattgt tggcgaaatt    480
tcaccattgc cttctcttcc aggacatact aatgaggatg tcaaaaatgc aattggggtc    540
ctcatcgggg gacttgaatg gaatgataac acagttcgag tctctgaaac tctacagaga    600
ttcgcttgga gaagcagtaa tgagactggg ggacctccat tcactccaac acagaaacgg    660
aaaatggcgg gaacaattag gtcagaagtt tgaagaaata agatggctga ttgaagaagt    720
gaggcataaa ttgaagacga cagagaatag ttttgagcaa ataacattta tgcaagcatt    780
acagctattg tttgaagtgg aacaagagat tagaacgttt tcgtttcagc ttatttaatg    840
ataa                                                                844
```

<210> SEQ ID NO 40
<211> LENGTH: 1728

<212> TYPE: DNA
<213> ORGANISM: Influenza virus

<400> SEQUENCE: 40

```
ccaaaatgaa agcaaaacta ctggtcctgt tatgtacatt tacagctaca tatgcagaca     60
caatatgtat aggctaccat gccaacaact caaccgacac tgttgacaca gtacttgaga    120
agaatgtgac agtgacacac tctgtcaacc tacttgagga cagtcacaat ggaaaactat    180
gtctactaaa aggaatagcc ccactacaat tgggtaattg cagcgttgcc ggatggatct    240
taggaaaccc agaatgcgaa ttactgattt ccaaggaatc atggtcctac attgtagaaa    300
caccaaatcc tgagaatgga acatgttacc cagggtattt cgccgactat gaggaactga    360
gggagcaatt gagttcagta tcttcatttg agagattcga aatattcccc aaagaaagct    420
catggcccaa ccacaccgta accggagtat cagcatcatg ctcccataat gggaaaagca    480
gtttttacag aaatttgcta tggctgacgg ggaagaatgg tttgtaccca aacctgagca    540
agtcctatgt aaacaacaaa gagaaagaag tccttgtact atggggtgtt catcacccgc    600
ctaacatagg gaaccaaagg gccctctatc atacagaaaa tgcttatgtc tctgtagtgt    660
cttcacatta tagcagaaga ttcaccccag aaatagccaa aagacccaaa gtaagagatc    720
aggaaggaag aatcaactac tactggactc tgctggaacc tggggataca ataatatttg    780
aggcaaatgg aaatctaata gcgccatggt atgcttttgc actgagtaga ggctttggat    840
caggaatcat cacctcaaat gcaccaatgg atgaatgtga tgcgaagtgt caaacacctc    900
agggagctat aaacagcagt cttcctttcc agaatgtaca cccagtcaca ataggagagt    960
gtccaaagta tgtcaggagt gcaaaattaa ggatggttac aggactaagg aacatcccat   1020
ccattcaatc cagaggtttg tttggagcca ttgccggttt cattgaaggg gggtggactg   1080
gaatggtaga tgggtggtat ggttatcatc atcagaatga gcaaggatct ggctatgctg   1140
cagatcaaaa aagtacacaa aatgccatta acgggattac aaacaaggtg aattctgtaa   1200
ttgagaaaat gaacactcaa ttcacagctg tgggcaaaga attcaacaaa ttggaaagaa   1260
ggatggaaaa cttaaataaa aaagttgatg atgggtttct agacatttgg acatataatg   1320
cagaattgtt ggttctactg gaaaatgaaa ggactttgga tttccatgac tccaatgtga   1380
agaatctgta tgagaaagta aaaagccaat taaagaataa tgccaaagaa ataggaaacg   1440
ggtgttttga attctatcac aagtgtaaca atgaatgcat ggagagtgtg aaaaatggaa   1500
cttatgacta tccaaaatat tccgaagaat caaagttaaa cagggagaaa attgatggag   1560
tgaaattgga atcaatggga gtctatcaga ttctggcgat ctactcaact gtcgccagtt   1620
ccctggttct tttggtctcc ctgggggcaa tcagcttctg gatgtgttcc aatgggtctt   1680
tgcagtgtag aatatgcatc tgagaccaga atttcagaaa tataagaa               1728
```

<210> SEQ ID NO 41
<211> LENGTH: 1414
<212> TYPE: DNA
<213> ORGANISM: Influenza virus

<400> SEQUENCE: 41

```
aatgaatcca aatcaaaaaa taataaccat tggatcaatc agtatagcaa tcggaataat     60
tagtctaatg ttgcaaatag gaaatattat ttcaatatgg gctagtcact caatccaaac    120
tggaagtcaa aaccacactg gagtatgcaa ccaaagaatc atcacatatg aaaacagcac    180
ctgggtgaat cacacatatg ttaatattaa caacactaat gttgttgctg gaaaggacaa    240
```

```
aacttcagtg acattggccg gcaattcatc tctttgttct atcagtggat gggctatata    300

cacaaaagac aacagcataa gaattggctc caaaggagat gtttttgtca taagagaacc    360

tttcatatca tgttctcact tggaatgcag aacctttttt ctgacccaag gtgctctatt    420

aaatgacaaa cattcaaatg ggaccgttaa ggacagaagt ccttataggg ccttaatgag    480

ctgtcctcta ggtgaagctc cgtccccata caattcaaag tttgaatcag ttgcatggtc    540

agcaagcgca tgccatgatg gcatgggctg gttaacaatc ggaatttctg gtccagacaa    600

tggagctgtg gctgtactaa aatacaacgg cataataact gaaaccataa aaagttggaa    660

aaagcgaata ttaagaacac aagagtctga atgtgtctgt gtgaacgggt catgtttcac    720

cataatgacc gatggcccga gtaatggggc cgcctcgtac aaaatcttca agatcgaaaa    780

ggggaaggtt actaaatcaa tagagttgaa tgcacccaat tttcattatg aggaatgttc    840

ctgttaccca gacactggca cagtgatgtg tgtatgcagg gacaactggc atggttcaaa    900

tcgaccttgg gtgtctttta atcaaaacct ggattatcaa ataggataca tctgcagtgg    960

ggtgttcggt gacaatccgc gtcccaaaga tggagagggc agctgtaatc cagtgactgt   1020

tgatggagca gacggagtaa aggggttttc atacaaatat ggtaatggtg tttggatagg   1080

aaggactaaa agtaacagac ttagaaaggg gtttgagatg atttgggatc ctaatggatg   1140

gacagatacc gacagtgatt tctcagtgaa acaggatgtt gtggcaataa ctgattggtc   1200

agggtacagc ggaagtttcg ttcaacatcc tgagttaaca ggattggact gtataagacc   1260

ttgcttctgg gttgagttag tcagaggact gcctagagaa aatacaacaa tctggactag   1320

tgggagcagc atttcttttt gtggcgtaaa tagtgatact gcaaactggt cttggccaga   1380

cggtgctgag ttgccgttca ccattgacaa gtag                               1414
```

<210> SEQ ID NO 42
<211> LENGTH: 2220
<212> TYPE: DNA
<213> ORGANISM: Influenza virus

<400> SEQUENCE: 42

```
agcgaaagca ggtactgatt cgaaatggaa gattttgtgc gacaatgctt caatccgatg     60

attgtcgagc ttgcggaaaa ggcaatgaaa gagtatggag aggacctgaa aatcgaaaca    120

aacaaatttg cagcaatatg cacccacttg gaagtatgct tcatgtattc agattttcat    180

ttcatcaatg agcaaggcga atcaataata gtagagcctg aggacccaaa tgcactttta    240

aaacacagat ttgagataat agaggggcga gatcgtacaa tggcatggac agttgtaaac    300

agtatttgca acaccacagg agctgagaaa ccaaagtttc tgccagatct gtatgattac    360

aaagagaata ggttcatcga aattggagtg acaaggagag aagttcacat atactatctg    420

gaaaaggcca acaaaattaa atctgagaag acacatattc acattttctc atttactggc    480

gaagaaatgg ccacaaaggc cgattacact ctcgatgaag aaagcagggc tagaattaaa    540

accagactat tcaccataag gcaagaaatg gcaagcagag gtctttggga ctcctttcgt    600

cagtccgaaa gaggcgaaga gacaattgaa gaaaggtttg aaatcacagg gacaatgcgc    660

aggctcgctg atcaaagcct tccgccgaac ttctcctgca ttgagaattt tagagcctat    720

gtggatggat ttgaaccgaa cggctacatt gagggcaagc tttctcaaat gtccaaagaa    780

gtaaatgcta aaattgagcc tttttttgaaa acaacacctc gaccaattag acttccgaat    840

gggcctcctt gttttcagcg gtcaaaattc ctgctgatgg attctttaaa attaagcatt    900

gaggatccaa atcatgaagg ggagggaata ccactatatg atgcaatcaa gtgtatgaga    960
```

```
acattctttg gatggaaaga acccactgtt gtcaagccac acgagaaggg aataaatccg   1020
aattatctgc tgtcgtggaa gcaggtgttg gaagagctgc aggacattga gagtgaggag   1080
aagattccaa gaacaaaaaa catgaaaaaa acgagtcagt taaagtgggc acttggtgag   1140
aacatggcac cagagaaggt ggattttgat gactgtaaag atataagcga tttgaagcaa   1200
tatgatagtg acgaacctga attaaggtca ttttcaagtt ggatccagaa tgagttcaac   1260
aaggcatgcg agctgaccga ttcaatctgg atagagctcg atgagattgg agaagatgtg   1320
gccccgattg aacacattgc aagcatgaga agaaattact tcacagctga ggtgtcccat   1380
tgcagagcca ctgaatatat aatgaaaggg gtatacatta atactgcttt gcttaatgca   1440
tcctgtgcag caatggatga tttccaacta attcctatga taagcaaatg tagaactaaa   1500
gagggaagga gaaagaccaa tttgtacggc ttcatcataa aaggaagatc tcacttaagg   1560
aatgataccg atgtggtaaa ctttgtgagc atggagtttt ccctcactga cccaagactt   1620
gagccacaca aatgggagaa gtactgtgtt cttgagatag gagatatgct tctaaggagt   1680
gcaataggcc aagtgtcaag gcccatgttc ttgtatgtaa gaacaaatgg aacctcaaaa   1740
attaaaatga aatggggaat ggagatgagg cgttgcctcc tccaatccct ccaacaaata   1800
gagagcatga ttgaagctga gtcctctgtc aaggagaaag acatgacaaa agagtttttt   1860
gagaatagat cagaaacatg gcccattgga gagtcaccaa aaggagtgga agaaggttcc   1920
attgggaaag tatgcaggac actattggct aaatcagtat tcaatagtct gtatgcatct   1980
ccacaattag aaggattttc agctgagtca agaaagttgc tccttattgt tcaggctctt   2040
agggacaatc tggaacctgg gacctttgat cttgggggac tatatgaagc aattgaggag   2100
tgcctgatta atgatccctg ggttttgctt aatgcttctt ggttcaactc cttcctaaaa   2160
catgcattga gatagctgag gcaatgctac tatttgttat ccatactgtc caaaaaagta   2220
```

<210> SEQ ID NO 43
<211> LENGTH: 2341
<212> TYPE: DNA
<213> ORGANISM: Influenza virus

<400> SEQUENCE: 43

```
agcgaaagca ggcaaaccat ttgaatggat gtcaatccga cattactttt cttaaaagtg     60
ccagcacaaa atgctataag cacaactttt ccttatactg gtgaccctcc ttacagccat    120
ggaacaggaa caggatacac catggataca gtcaacagga cacatcagta ctcagaaaga    180
ggaagatgga cgaaaaatac cgaaactgga gcaccgcaac tcaacccaat tgatgggcca    240
ctaccagaag acaatgaacc aagtggctat gcccaaacag attgtgtatt agaggcaatg    300
gctttccttg aagaatccca tcctggtatt tttgaaaact cttgtattga aacaatggag    360
gttgttcagc aaacaagggt ggacaaactg acacaaggca gacaaaccta tgactggact    420
ctaaatagga accagcctgc tgccacagca ttggcaaaca ccatagaagt attcagatca    480
aatggcctca tagcaaatga atctggaagg ctaatagact tccttaaaga tgtaatggag    540
tcgatggaca gagacgaagt agaggtcaca actcattttc aaagaaagag gagagtgaga    600
gacaatgtaa ctaaaaaaat ggtgacccaa agaacaatag gaaaaaagaa acataaatta    660
gacaaaagaa gttacctaat tagggcatta accctgaaca caatgaccaa agatgctgag    720
agggggaaac taaaacgcag agcaattgca accccaggaa tgcaaataag gggtttgta    780
tactttgttg agacactggc aagaagcata tgtgaaaagc ttgaacaatc agggttgcca    840
```

```
gttggaggaa atgagaagaa agcaaagtta gcaaatgttg taaggaagat gatgaccaac    900

tcccaggaca ctgaaatttc ttttaccatc actggagata acacaaaatg gaacgaaaat    960

caaaacccta gaatgttctt ggccatgatc acatatataa ccaaagatca gcctgaatgg   1020

ttcagaaata ttctaagtat tgctccaata atgttttcaa acaaaatggc gagactaggt   1080

agggggtata tgtttgaaag caagagtatg aaactgagaa cccaaatacc tgcagagatg   1140

ctagccaaca tagatttgaa atatttcaat gattcaacta aaaagaaaat tgaaaaaatt   1200

cgaccattat taatagatgg aactgcatca ttgagtcctg gaatgatgat gggcatgttc   1260

aatatgttaa gcaccgtctt gggcgtttcc attctgaatc ttgggcaaaa aagatacacc   1320

aagactactt actggtggga tggtcttcaa tcgtctgatg attttgcttt gattgtgaat   1380

gcacccaatt atgcaggaat tcaagctgga gttgacaggt tttatcgaac ctgtaagctg   1440

ctcggaatta atatgagcaa aaagaagtct tacataaaca gaacaggtac ctttgaattc   1500

acgagctttt tctatcgtta tgggtttgtt gccaatttca gcatggagct tcctagtttt   1560

ggggtgtctg ggtcaatgga atctgcagac atgagtattg gagtcactgt catcaaaaac   1620

aatatgataa acaatgacct tggcccagca actgctcaaa tggcccttca gttatttata   1680

aaagattaca ggtacactta tcgatgccac agaggtgaca cacaaataca aacccggaga   1740

tcatttgaaa taaagaaact atgggaccaa acccgctcca aagctgggct gttggtctct   1800

gatggaggcc ccaatttata taacattagg aatctacata ttcctgaagt ctgcttgaaa   1860

tgggagttga tggatgagga ttaccagggg cgtttatgca acccattgaa cccgtttgtc   1920

agccataaag agattgaatc agtgaacaat gcagtgataa tgccggcaca tggtccagcc   1980

aaaaatatgg agtatgacgc tgttgcaaca acacactctt gggtccccaa aagaaatcga   2040

tccattttaa acacgagcca aagagggata cttgaagatg agcaaatgta ccaaaggtgc   2100

tgcaatttat ttgaaaaatt cttcccaagt agctcataca gaagaccagt tggaatatcc   2160

agtatggtag aggctatggt ttcaagagcc cgaattgatg cacggattga tttcgaatct   2220

ggaaggataa agaaagagga attcgctgag atcatgaaga cctgttccac cattgaagac   2280

ctcagacggc aaaaataggg aatttggctt gtccttcatg aaaaaatgcc ttgtttctac   2340

t                                                                   2341
```

```
<210> SEQ ID NO 44
<211> LENGTH: 2341
<212> TYPE: DNA
<213> ORGANISM: Influenza virus

<400> SEQUENCE: 44
```

```
agcgaaagca ggtcaattat attcaatatg gaaagaataa aagagctaag gaatctgatg     60

tcacaatctc gcactcgcga gatacttacc aaaactactg tagaccacat ggccataata    120

aagaaataca catcaggaag acaggagaaa aacccatcac ttaggatgaa atggatgatg    180

gcaatgaaat acccaattac agctgataaa aggataacgg aaatgattcc tgaaagaaat    240

gagcaaggac agacactatg gagtaaagtg aatgatgccg gatcagaccg agtgatgata    300

tcacccctag ctgtgacatg gtggaacaga aatggaccag tggcaaacac tatccactat    360

ccaaaaatct acaaaactta ctttgaaaag gttgaaaggt taaaacatgg aacctttggc    420

cctgtacact ttagaaacca agtcaaaata cgccgaagag tcgacataaa tcctggtcat    480

gcagacctca gcgccaagga ggcacaggat gtaattatgg aagttgtttt ccctaatgaa    540

gtgggagcca gaatactaac atcagaatcg caattaacga taactaagga gaaaaaagag    600
```

```
gaactccaga attgcaaaat ttccccttttg atggttgcat acatgttaga gagggaactt    660

gtccgcaaaa caagatttct cccggttgca ggtggaacaa gcagtgtgta cattgaagtt    720

ttgcatttaa cacaggggac atgctgggag cagatgtaca ctccaggtgg ggaggtgagg    780

aatgatgatg ttgatcaaag cctaattatt gctgctagga acatagtgag aagagctgca    840

gtatcagcag atccactagc atctttatta gaaatgtgcc atagcacaca gattggtgga    900

acaaggatgg tggatattct caggcaaaat ccaacagaag aacaagctgt ggacatatgc    960

aaagcagcaa tggggctgag aatcagttca tccttcagtt ttggcggatt cacatttaag   1020

agaacaagtg gatcgtcagt caaaagggag gaagaagtgc taacgggcaa tctgcaaaca   1080

ttgaagctaa ctgtgcatga gggatatgaa gaattcacaa tagttgggaa aaaggcaaca   1140

gctatactca gaaaagcaac caggagattg attcaactaa tagtgagtgg aagagacgaa   1200

cagtcaatag tcgaagcaat agttgtagca atggtattct cacaagaaga ttgcatggta   1260

aaagcggtta gaggtgatct gaatttcgtt aatagagcga atcagcggtt gaatcccatg   1320

catcaacttt tgagacattt tcagaaggat gctaaagtac ttttcctaaa ttggggaatt   1380

gaacatattg acaatgtgat gggaatgatt gggatattac ctgatatgac tccaagtacc   1440

gagatgtcaa tgagaggagt gagagtcagc aaaatgggtg tagatgaata ctccaatgct   1500

gaaagggtag tggtaagcat tgaccgtttt ttgagggtcc gggaccaaag aggaaatgta   1560

ttactgtctc cagaggaagt cagtgaaaca caaggaacag agaaactgac aataacttac   1620

tcttcatcat tgatgtggga gattaatggc cctgagtcag tgttgatcaa tacctaccaa   1680

tggatcatca gaaactggga gactgttaaa attcagtggt ctcagaaccc tacaatgcta   1740

tacaataaaa tggaatttga gccatttcaa tctctagtcc ccaaggccat tagaggccaa   1800

tacagtgggt ttgttagaac tctatttcaa caaatgaggg atgtgctcgg gacctttgac   1860

acaactcaga taataaaact tcttcccttt gcagccgctc caccaaagca aagtagaatg   1920

caattctcgt cattaactgt gaatgtgagg ggatcaggaa tgagaatact tgtaaggggt   1980

aattctccag tattcaacta caacaagacc actaagagac tcacaatcct cggaaaggat   2040

gctggcactt taactgaaga cccagatgaa ggcacagctg gagtggaatc tgctgtttta   2100

aggggattcc tcattctagg caaagaagat agaagatatg ggccagcatt aagcatcagt   2160

gaattgagca accttgcgaa aggggagaaa gctaatgtgc taattgggca aggggatgta   2220

gtgttggtaa tgaaacgaaa acgggactct agcatactta ctgacagcca gacagcgacc   2280

aaaagaattc ggatggccat caattaattt cgaataattt aaaaacgacc ttgtttctac   2340

t                                                                   2341
```

<210> SEQ ID NO 45
<211> LENGTH: 1565
<212> TYPE: DNA
<213> ORGANISM: Influenza virus

<400> SEQUENCE: 45

```
agcaaaagca gggtagataa tcactcactg agtgacatca aagtcatggc gtcccaaggc     60

accaaacggt cttacgaaca gatggagact gatggggaac gccagaatgc aactgaaatc    120

agagcatccg tcggaagaat gattggggga attgggcgat tctacatcca aatgtgcacc    180

gagcttaagc tcaatgatta tgagggacga ctgatccaga acagcttaac aatagagaga    240

atggtgcttt ctgcttttga tgagaggaga aataaatatc tggaagaaca tcccagcgca    300
```

```
gggaaagatc ctaagaaaac tggaggaccc atatacaaga gagtagatgg aaagtgggtg    360

agggaactcg tcctttatga caaagaagaa ataaggcgga tttggcgcca agccaacaat    420

ggtgatgatg caacagctgg tttgactcac attatgatct ggcattctaa tttgaatgat    480

acaacttacc agaggacaag agctcttgtc cgcaccggaa tggatcccag gatgtgctct    540

ttgatgcaag gttcaactct ccctagaaga tctggagcag caggcgctgc agtcaaagga    600

gttgggacaa tggtattgga gttaatcagg atgatcaaac gtgggatcaa cgaccgaaac    660

ttctggaggg gtgagaatgg gagaaaaaca aggattgctt atgagagaat gtgcaacatt    720

ctcaaaggaa aatttcaaac agctgcacaa aaagcaatga tggatcaagt gagagaaagc    780

cggaacccag gaaatgctga gatcgaagat ctcacttttc tggcacggtc tgcactcata    840

ttgagaggat cagttgctca caagtcttgc ctgcctgctt gtgtgtatgg accagccgta    900

gccagtgggt atgacttcga aaaagaggga tactctttgg tgggagtaga ccctttcaaa    960

ctgcttcaaa ccagtcaggt atacagccta attagaccaa acgagaatcc cgcacacaag   1020

agccagttgg tgtggatggc atgcaattct gctgcatttg aagatctaag agtgtcaagc   1080

ttcatcagag ggacaagagt acttccaagg gggaagctct ccactagagg agtacaaatt   1140

gcttcaaatg aaaacatgga tgctattgtc tcaagtactc ttgaactgag aagcagatac   1200

tgggccataa gaaccagaag tggagggaac accaatcaac aaagggcctc tgcgggccaa   1260

atcagcacac aacctacgtt ttctgtgcag agaaacctcc catttgacaa aacaaccatc   1320

atggcagcat tcactgggaa tacagaggga agaacatcag acatgcgggc agaaatcata   1380

aagatgatgg aaagtgcaag accagaagaa gtgtccttcc agggacgggg agtctttgag   1440

ctctcggacg aaagggcaac gaacccgatc gtgccctcct ttgacatgag taatgaagga   1500

tcttatttct tcggagacaa tgcagaggag tacgacaatt aatgaaaaat acccttgttt   1560

ctact                                                               1565
```

<210> SEQ ID NO 46
<211> LENGTH: 1027
<212> TYPE: DNA
<213> ORGANISM: Influenza virus

<400> SEQUENCE: 46

```
agcaaaagca ggtagatatt gaaagatgag tcttctaacc gaggtcgaaa cgtacgttct     60

ctctatcgtc ccatcaggcc ccctcaaagc cgagatcgca cagagacttg aagatgtatt    120

tgctggaaag aataccgatc ttgaggctct catggaatgg ctaaagacaa gaccaatcct    180

gtcacctctg actaagggga ttttaggatt tgtgttcacg ctcaccgtgc ccagtgagcg    240

aggactgcag cgtagacgct ttgtccaaaa tgcccttaat gggaatgggg atccaaataa    300

tatggacaag gctgtcaaac tgtatcgaaa gcttaagagg gagataacat tccatggggc    360

caaagaaata gcactcagtt attctgctgg agcacttgcc agttgtatgg gactcatata    420

caacaggatg ggggctgtga ccaccgaatc agcatttggc cttatatgtg caacctgtga    480

acagattgcc gactcccagc ataagtctca taggcaaatg gtaacaacaa ccaatccatt    540

aataagacat gagaacagaa tggttctggc cagcactaca gctaaggcta tggagcaaat    600

ggctggatcg agtgaacaag cagctgaggc catggaggtt gctagtcagg ccaggcagat    660

ggtgcaggca atgagagcca ttgggactca tcctagctct agcactggtc tgaaaaatga    720

tctccttgaa aatttgcagg cctatcagaa acgaatgggg gtgcagatgc aacgattcaa    780

gtgatcctct tgttgttgcc gcaagtataa ttgggattgt gcacctgata ttgtggatta    840
```

```
ttgatcgcct tttttccaaa agcatttatc gtatttttaa acacggttta aaaagagggc    900

cttctacgga aggagtaccg gagtctatga gggaagaata tcgagaggaa cagcagaatg    960

ctgtggatgc tgacgatggt cattttgtca gcatagagct agagtaaaaa actaccttgt   1020

ttctact                                                             1027
```

```
<210> SEQ ID NO 47
<211> LENGTH: 889
<212> TYPE: DNA
<213> ORGANISM: Influenza virus

<400> SEQUENCE: 47

agcaaaagca gggtggcaaa gacataatgg attcccacac tgtgtcaagc tttcaggtag     60

attgtttcct ttggcatgtc cgcaaacaag ttgcagacca agatctaggc gatgccccct    120

tccttgatcg gcttcgccga gatcagaagt ctctaaaggg acgaggcaac actctcggtc    180

tgaacatcga aacagccact tgtgttggaa agcaaatagt agagaggatt ctgaaagaag    240

aatccgatga gacatttaga atgaccatgg cctccgcact tgcttcgcgg tacctaactg    300

acatgactgt tgaagaaatg tcaagggact ggttcatgct catgcccaag cagaaagtgg    360

ctggccctct ttgtgtcaga atggaccagg cgataatgga taagaacatc atactgaaag    420

cgaacttcag tgtgattttt gaccggttgg agaatctgac attactaagg gctttcaccg    480

aagagggagc aattgttggc gaaatttcac cattgccttc ttttccagga catactaatg    540

aggatgtcaa aaatgcaatt ggggtcctca tcgggggact tgaatggaat gataacacag    600

ttcgagtctc tgaagctcta cagagattcg cttggagaag cagtaatgag actgggggac    660

ctccattcac tacaacacag aaacggaaaa tggcgggaac aattaggtca gaagtttgaa    720

gaaataagat ggctgattga agaagtgagg cataaattga agacgacaga gagtagtttt    780

gaacaaataa catttatgca agcattacag ctattgtttg aagtggaaca agagattaga    840

acgttctcgt ttcagcttat ttaatgataa aaacaccctt gtttctact                889
```

```
<210> SEQ ID NO 48
<211> LENGTH: 1775
<212> TYPE: DNA
<213> ORGANISM: Influenza virus

<400> SEQUENCE: 48

agcgaaagca ggggaaaata aaagcaacca aaatgaaagt aaaactactg gttctgttat     60

gtacatttac agctacatat gcagacacaa tatgtatagg ctaccatgcc aacaactcaa    120

ccgacactgt tgacacagta cttgagaaga atgtaacagt gacacactct gtcaacctac    180

ttgaggacag tcacaatgga aaactatgtc tactaaaagg aatagcccca ctacaattgg    240

gtaattgcag cgttgccgga tggatcttag gaaacccaga atgcgaatta ctgatttcca    300

aggaatcatg gtcctacatt gtagaaacac caaatcctga gaatggaaca tgttacccag    360

ggtatttcgc cgactatgag gaactgaggg agcaattgag ttcagtatct tcatttgaaa    420

ggttcgaaat attccccaaa gagagctcat ggcccaacca caccgtaacc ggagtatcag    480

catcatgctc ccataacggg aaaagcagtt tttacagaaa tttgctatgg ctgacgggga    540

agaatggttt gtacccaaac ctgagcaagt cctatgcaaa caacaaagag aaagaagtcc    600

ttgtactatg ggtgttcat cacccgccta acatagggga ccaaagggcc ctctatcata    660

cagaaaatgc ttatgtctct gtagtgtctt cacattatag cagaagattc accccagaaa    720
```

```
tagccaaaag acccaaggtg agagaccagg aaggaagaat caactactac tggactctgc    780
tggaacccgg ggatacaata atatttgagg caaatggaaa tctaatagcg ccaaggtatg    840
ctttcgcact gagtagaggc ttgggatcag gaatcatcac ctcaaatgca ccaatggatg    900
aatgtgatgc aaagtgtcaa acacctcagg gagctataaa cagcagtctt cctttccaga    960
atgtacaccc agtcacaata ggagagtgtc caaagtatgt caggagtgca aaattaagga   1020
tggttacagg actaaggaac atcccatcca ttcaatccag aggtttgttt ggagcaattg   1080
ccggtttcat tgaagggggg tggactggaa tggtagatgg ttggtatggt tatcatcatc   1140
agaatgagca aggatctggg tatgctgcag atcaaaaaag cacacaaaat gccattaacg   1200
ggattacaaa caaggtgaat tctgtaattg agaaaatgaa cactcaattc acagctgtgg   1260
gcaaagaatt caacaaattg gaaagaagga tggaaaactt aaataaaaaa gttgatgatg   1320
ggtttctaga catttggacc tataatgcag aattgttggt tctactggaa aatgaaagga   1380
ctttggattt ccatgactcc aacgtgaaga atctgtatga gaaagtaaaa agccaattaa   1440
agaataatgc caaagaaata ggaaacgggt gttttgaatt ctatcacaag tgtaacgatg   1500
aatgcatgga gagtgtgaaa aatggaactt atgactatcc aaaatattcc gaagaatcaa   1560
agttaaacag agagaaaatt gatggagtga aattggaatc aatgggagtc tatcagattc   1620
tggcgatcta ctcaacagtc gccagttccc tggttctttt ggtctccctg gggggcaatca  1680
gcttctggat gtgttccaat gggtctttgc agtgtagaat atgcatctaa gaccagaatt   1740
tcagaaatat aaggaaaaac acccttgttt ctact                              1775
```

```
<210> SEQ ID NO 49
<211> LENGTH: 1462
<212> TYPE: DNA
<213> ORGANISM: Influenza virus

<400> SEQUENCE: 49
```

```
agcaaaagca ggagtttaaa atgaatccaa atcaaaaaat aataaccatt ggatcaatca     60
gtatagcaat cggaataatt agtctaatgt tgcaaatagg aaatattatt tcaatatggg    120
ctagtcactc aatccaaact ggaagtcaaa accacactgg aatatgcaac caaaaaatca    180
tcacatatga aaacagcacc tgggtgaatc acacatatgt taatattaac aacactaatg    240
ttgttgctgg aaaggacaaa acttcagtga cactggccgg caattcatct ctttgtccta    300
tcagtggatg ggctatatac acaaaagaca acagcataag aattggctcc aaaggagatg    360
tttttgtcat aagagaacct ttcatatcat gttctcactt ggaatgcaga accttttttc    420
tgacccaagg tgctctatta aatgacaaac attcaaatgg aaccgttaag gacagaagtc    480
cttatagggc cttaatgagc tgtcctctag gtgaagcccc gtcaccatac aattcaaagt    540
ttgaatcagt tgcatggtca gcaagcgcat gccatgatgg caagggctgg ttaacaatcg    600
gaatttctgg tccagacaat ggagctgtgg ctgtactaaa atacaacgga ataataactg    660
aaaccataaa aagttgggaa aagcgaatat tgagaacaca agagtctgaa tgtgtttgtg    720
tgaacgggtc atgtttcacc ataatgaccg atggcccgag taatggggcc gcctcgtaca    780
aaatcttcaa gatcgaaaag gggaaggtta ctaaatcaac agagttgaat gcacccaatt    840
ttcattatga ggaatgttcc tgttacccag acactggcac agtgatgtgt gtatgcaggg    900
acaactggca tggttcaaat cgaccttggg tatcttttaa tcaaaacttg gattatcaaa    960
taggatacat ctgcagtgga gtgttcggtg acaatccgcg tcccaaagat gggaagggca   1020
gctgtaatcc agtgactgtt gatggagcag acggagttaa ggggttttca tacaaatatg   1080
```

```
gtaatggtgt ttggatagga aggactaaaa gtaacagact tagaaagggg tttgagatga   1140

tttgggatcc taatggatgg acagataccg acagtgattt ctcagtgaaa caggatgttg   1200

tggcaataac tgattggtca gggtacagcg gaagtttcgt ccaacatcct gagttaacag   1260

gattggactg tataagacct tgcttctggg ttgagttagt cagaggactg cctagagaaa   1320

atacaacaat ctggactagt gggagcagca tttctttttg tggcgttgat agtgatactg   1380

caaattggtc ttggccagac ggtgctgagt tgccgttcac cattgacaag tagctcgttg   1440

aaaaaaactc cttgtttcta ct                                            1462
```

<210> SEQ ID NO 50
<211> LENGTH: 566
<212> TYPE: PRT
<213> ORGANISM: Influenza virus

<400> SEQUENCE: 50

```
Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser His Tyr Asn
    210                 215                 220

Arg Arg Phe Thr Pro Glu Ile Ala Lys Arg Pro Lys Val Arg Asn Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300
```

```
Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Ile Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 51
<211> LENGTH: 470
<212> TYPE: PRT
<213> ORGANISM: Influenza virus

<400> SEQUENCE: 51

Met Asn Pro Asn Gln Lys Ile Ile Thr Ile Gly Ser Ile Cys Met Thr
1               5                   10                  15

Ile Gly Ile Ile Ser Leu Ile Leu Gln Ile Gly Asn Ile Ile Ser Ile
            20                  25                  30

Trp Val Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
    50                  55                  60

Thr Tyr Val Asn Ile Asn Asn Thr Asn Val Val Ala Gly Lys Asp Thr
65                  70                  75                  80

Thr Ser Val Thr Leu Ala Gly Asn Ser Ser Leu Cys Pro Ile Arg Gly
                85                  90                  95

Trp Ala Ile Tyr Ser Lys Asp Asn Ser Ile Arg Ile Gly Ser Lys Gly
```

```
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asp Gly Ala Val Ala Val Leu Lys Tyr
        195                 200                 205

Asn Gly Ile Ile Thr Glu Thr Ile Lys Ser Trp Arg Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Pro Ala Ser Tyr Arg Ile Phe
                245                 250                 255

Lys Ile Glu Lys Gly Lys Ile Thr Lys Ser Ile Glu Leu Asp Ala Pro
            260                 265                 270

Asn Ser His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Lys Gly Ser Cys Asp
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Ser Ser Arg
        355                 360                 365

Lys Gly Phe Glu Met Ile Trp Asp Pro Asn Gly Trp Thr Asp Thr Asp
    370                 375                 380

Ser Asn Phe Leu Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Val Arg Gly Arg Pro Arg
            420                 425                 430

Glu Gly Thr Thr Val Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465                 470


<210> SEQ ID NO 52
<211> LENGTH: 469
<212> TYPE: PRT
<213> ORGANISM: Influenza virus

<400> SEQUENCE: 52
```

-continued

```
Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
```

```
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 53
<211> LENGTH: 716
<212> TYPE: PRT
<213> ORGANISM: Influenza virus

<400> SEQUENCE: 53

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Pro
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320
```

```
Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715
```

<210> SEQ ID NO 54
<211> LENGTH: 757
<212> TYPE: PRT

<213> ORGANISM: Influenza virus

<400> SEQUENCE: 54

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Arg Gly Arg Trp Thr Lys Asn Thr Glu Thr Gly Ala Pro
    50                  55                  60

Gln Leu Asn Pro Ile Asp Gly Pro Leu Pro Lys Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Ile Ala Asn Glu Ser
145                 150                 155                 160

Gly Arg Leu Ile Asp Phe Leu Lys Asp Val Met Glu Ser Met Asp Arg
                165                 170                 175

Asp Glu Val Glu Val Thr Thr His Phe Gln Arg Lys Arg Arg Val Arg
            180                 185                 190

Asp Asn Val Thr Lys Lys Met Val Thr Gln Arg Thr Ile Gly Lys Lys
        195                 200                 205

Lys His Lys Leu Asp Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Ile Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Asn Ile Asp Leu Lys Tyr Phe Asn Asp Ser
    370                 375                 380

Thr Lys Arg Lys Ile Glu Lys Ile Arg Pro Leu Leu Ile Asp Gly Thr
385                 390                 395                 400
```

```
Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn Tyr Ala Gly Ile Gln Ala Gly Val Asp
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Val Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Asp Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Ser Asn Pro Phe Val Ser His Lys Glu Ile Glu Ser Val
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Val Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Thr Cys Ser Thr Ile Glu Asp
            740                 745                 750

Leu Arg Arg Gln Lys
        755


<210> SEQ ID NO 55
<211> LENGTH: 759
<212> TYPE: PRT
<213> ORGANISM: Influenza virus

<400> SEQUENCE: 55

Met Glu Arg Ile Lys Glu Leu Arg Asn Leu Met Ser Gln Ser Arg Thr
1               5                   10                  15
```

-continued

```
Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Val Asn Asp Ala Gly Ser Asp Arg Val Met Ile Ser Pro Leu Ala Val
                85                  90                  95

Thr Trp Trp Asn Arg Asn Gly Pro Val Ala Ser Thr Ile His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asn Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Leu Thr Val His Glu Gly Tyr Glu Glu Phe Thr Met Val Gly Lys
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Val Glu Ala Ile Val Val
385                 390                 395                 400

Ala Met Val Phe Ser Gln Glu Asp Cys Met Val Lys Ala Val Arg Gly
                405                 410                 415

Asp Leu Asn Phe Val Asn Arg Ala Asn Gln Arg Leu Asn Pro Met His
            420                 425                 430
```

```
Gln Leu Leu Arg His Phe Gln Lys Asp Ala Lys Val Leu Phe Leu Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Met Arg Gly Val Arg Val
465                 470                 475                 480

Ser Lys Met Gly Val Asp Glu Tyr Ser Asn Ala Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Ile Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 56
<211> LENGTH: 498
<212> TYPE: PRT
<213> ORGANISM: Influenza virus

<400> SEQUENCE: 56

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45
```

```
Leu Asn Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Val Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Ile Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Leu Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Ile Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Val Asp Pro Phe
    290                 295                 300

Lys Leu Leu Gln Thr Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Ser Ser Phe Ile Arg Gly Thr Arg Val
            340                 345                 350

Leu Pro Arg Gly Lys Leu Ser Thr Arg Gly Val Gln Ile Ala Ser Asn
        355                 360                 365

Glu Asn Met Asp Ala Ile Val Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Thr Gln Pro Thr Phe Ser Val Gln Arg
                405                 410                 415

Asn Leu Pro Phe Asp Lys Thr Thr Ile Met Ala Ala Phe Thr Gly Asn
            420                 425                 430

Thr Glu Gly Arg Thr Ser Asp Met Arg Ala Glu Ile Ile Lys Met Met
        435                 440                 445

Glu Ser Ala Arg Pro Glu Glu Val Ser Phe Gln Gly Arg Gly Val Phe
    450                 455                 460
```

```
Glu Leu Ser Asp Glu Arg Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 57
<211> LENGTH: 252
<212> TYPE: PRT
<213> ORGANISM: Influenza virus

<400> SEQUENCE: 57

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asn Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Ser Ala Phe
    130                 135                 140

Gly Leu Ile Cys Ala Thr Cys Glu Gln Ile Ala Asp Ser Gln His Lys
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr His Pro Ser
    210                 215                 220

Ser Ser Thr Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 58
<211> LENGTH: 470
<212> TYPE: PRT
<213> ORGANISM: Influenza virus

<400> SEQUENCE: 58

Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
            20                  25                  30

Trp Ala Ser His Ser Ile Gln Thr Gly Ser Gln Asn His Thr Gly Val
```

```
        35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Phe His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Lys
            340                 345                 350

Tyr Gly Asn Gly Val Trp Ile Gly Arg Thr Lys Ser Asn Arg Leu Arg
        355                 360                 365

Lys Gly Phe Glu Met Ile Trp Asp Pro Asn Gly Trp Thr Asp Thr Asp
    370                 375                 380

Ser Asp Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460
```

```
Pro Phe Thr Ile Asp Lys
465                 470


<210> SEQ ID NO 59
<211> LENGTH: 716
<212> TYPE: PRT
<213> ORGANISM: Influenza virus

<400> SEQUENCE: 59

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Val Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Gly Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Asn Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Asn Arg Gly Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Arg Leu Ala Asp Gln Ser Leu Pro Pro Asn Phe Ser
    210                 215                 220

Cys Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Gln
                245                 250                 255

Ile Glu Pro Phe Leu Lys Thr Thr Pro Arg Pro Ile Lys Leu Pro Asn
            260                 265                 270

Gly Pro Pro Cys Tyr Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Tyr Ile Val Lys Pro His Glu Lys Gly Ile Asn Ser Asn Tyr Leu Leu
                325                 330                 335

Ser Trp Lys Gln Val Leu Ser Glu Leu Gln Asp Ile Glu Asn Glu Glu
            340                 345                 350

Lys Ile Pro Arg Thr Lys Asn Met Lys Lys Thr Ser Gln Leu Lys Trp
```

```
        355                 360                 365

Ala Leu Gly Glu Asn Met Ala Pro Glu Lys Val Asp Phe Glu Asn Cys
    370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Val Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Ile Ser Arg Pro
545                 550                 555                 560

Met Phe Leu Tyr Val Arg Thr Asn Gly Thr Ser Lys Val Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Ala Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715


<210> SEQ ID NO 60
<211> LENGTH: 757
<212> TYPE: PRT
<213> ORGANISM: Influenza virus

<400> SEQUENCE: 60

Met Asp Val Asn Pro Thr Leu Leu Phe Leu Lys Val Pro Ala Gln Asn
1               5                   10                  15
```

```
Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Ala Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
```

```
        435                 440                 445

Leu Ile Val Asn Ala Pro Asn His Glu Gly Ile Gln Ala Gly Val Asn
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Arg Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asn Tyr Arg Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Arg
        755


<210> SEQ ID NO 61
<211> LENGTH: 759
<212> TYPE: PRT
<213> ORGANISM: Influenza virus

<400> SEQUENCE: 61

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45
```

```
Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Val Thr Ser Thr Val His Tyr Pro
            100                 105                 110

Lys Val Tyr Lys Thr Tyr Phe Asp Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Arg Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Val Leu Thr Gly Asn Leu Gln Thr Leu
            340                 345                 350

Lys Ile Arg Val His Glu Gly Tyr Glu Glu Phe Thr Met Val Gly Lys
        355                 360                 365

Arg Ala Thr Ala Ile Leu Arg Lys Ala Thr Arg Arg Leu Val Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Ser Val Met Gly Met Val Gly Val Leu
    450                 455                 460

Pro Asp Met Thr Pro Ser Thr Glu Met Ser Met Arg Gly Ile Arg Val
```

```
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Arg Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ala Val
545                 550                 555                 560

Lys Ile Gln Trp Ser Gln Asn Pro Ala Met Leu Tyr Asn Lys Met Glu
                565                 570                 575

Phe Glu Pro Phe Gln Ser Leu Val Pro Lys Ala Ile Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
            660                 665                 670

Gly Thr Leu Ile Glu Asp Pro Asp Glu Ser Thr Ser Gly Val Glu Ser
        675                 680                 685

Ala Val Leu Arg Gly Phe Leu Ile Ile Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 62
<211> LENGTH: 498
<212> TYPE: PRT
<213> ORGANISM: Influenza virus

<400> SEQUENCE: 62

Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Lys Met Val Leu Ser Ala Phe Asp Glu Arg Arg Asn Lys Tyr Leu Glu
65                  70                  75                  80
```

```
Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ser Ser Gly
        275                 280                 285

Tyr Asn Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Asn Met Gly Ser Gly Thr Leu Glu Leu Arg Ser Gly
    370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 63
<211> LENGTH: 252
<212> TYPE: PRT
<213> ORGANISM: Influenza virus

<400> SEQUENCE: 63

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Ala Ile Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250

<210> SEQ ID NO 64
<211> LENGTH: 97
<212> TYPE: PRT
<213> ORGANISM: Influenza virus

<400> SEQUENCE: 64

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Asn Ile
            20                  25                  30

Ile Gly Ile Leu His Leu Ile Leu Trp Ile Leu Asp Arg Leu Phe Phe
        35                  40                  45

Lys Cys Val Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

```
Gln Asn Ala Val Asp Ala Asp Asp Ser His Phe Val Ser Ile Glu Leu
                85                  90                  95

Glu


<210> SEQ ID NO 65
<211> LENGTH: 846
<212> TYPE: DNA
<213> ORGANISM: Influenza virus

<400> SEQUENCE: 65

aatggattcc aacactgtgt caagtttcca ggtagattgc tttctttggc atatccggaa      60

acaagttgta gaccaagaac tgagtgatgc cccattcctt gatcggcttc gccgagatca     120

gaggtcccta aggggaagag gcaatactct cggtctagac atcaaagcag ccacccatgt     180

tggaaagcaa attgtagaaa agattctgaa agaagaatct gatgaggcac ttaaaatgac     240

catggtctcc acacctgctt cgcgatacat aactgacatg actattgagg aattgtcaag     300

aaactggttc atgctaatgc ccaagcagaa agtggaagga cctctttgca tcagaatgga     360

ccaggcaatc atggagaaaa acatcatgtt gaaagcgaat ttcagtgtga tttctgaccg     420

actagagacc atagtattac taagggcttt caccgaagag ggagcaattg ttggcgaaat     480

ctcaccattg ccttcttttc caggacatac tattgaggat gtcaaaaatg caattggggt     540

cctcatcgga ggacttgaat ggaatgataa cacagttcga gtctctaaaa atctacagag     600

attcgcttgg agaagcagta atgagaatgg gggacctcca cttactccaa aacagaaacg     660

gaaaatggcg agaacagcta ggtcaaaagt ttgaagagat aagatggctg attgaagaag     720

tgagacacag actaaaaaca actgaaaata gctttgaaca aataacattc atgcaagcat     780

tacaactgct gtttgaagtg gaacaggaga taagaacttt ctcatttcag cttatttaat     840

gataaa                                                                846


<210> SEQ ID NO 66
<211> LENGTH: 566
<212> TYPE: PRT
<213> ORGANISM: Influenza virus

<400> SEQUENCE: 66

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140
```

```
Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
```

565

<210> SEQ ID NO 67
<211> LENGTH: 469
<212> TYPE: PRT
<213> ORGANISM: Influenza virus

<400> SEQUENCE: 67

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Glu Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Leu Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365
```

```
Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465


<210> SEQ ID NO 68
<211> LENGTH: 716
<212> TYPE: PRT
<213> ORGANISM: Influenza virus

<400> SEQUENCE: 68

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Ile Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Lys Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Pro
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270
```

```
Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685
```

```
Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715


<210> SEQ ID NO 69
<211> LENGTH: 252
<212> TYPE: PRT
<213> ORGANISM: Influenza virus

<400> SEQUENCE: 69

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asn Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Ser Ala Phe
    130                 135                 140

Gly Leu Ile Cys Ala Thr Cys Glu Gln Ile Ala Asp Ser Gln His Lys
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr His Pro Ser
    210                 215                 220

Ser Ser Thr Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250


<210> SEQ ID NO 70
<211> LENGTH: 566
<212> TYPE: PRT
<213> ORGANISM: Influenza virus

<400> SEQUENCE: 70

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45
```

-continued

```
Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
```

```
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 71
<211> LENGTH: 2305
<212> TYPE: DNA
<213> ORGANISM: Influenza virus

<400> SEQUENCE: 71

agcagaagcg gtgcgtttga tttgtcataa tggatacttt tattacaaga aacttccaga     60

ctacaataat acaaaaggcc aaaaacacaa tggcagaatt tagtgaagat cctgaattgc    120

aaccagcaat gctattcaat atctgcgtcc atctagaggt ttgctatgta ataagtgaca    180

tgaattttct tgacgaagaa ggaaaagcat atacagcatt agaaggacaa gggaaagaac    240

aaaacttgag accacaatat gaagtaattg agggaatgcc aagaaccata gcatggatgg    300

tccagagatc cttagctcaa gagcatggaa tagagactcc caagtatctg gctgatttgt    360

ttgattataa aaccaaaaga tttatagaag ttggaataac aaagggattg gctgatgatt    420

acttttggaa aaagaaagaa aagttgggaa atagcatgga actgatgata ttcagctaca    480

atcaagacta ctcgttaagt aatgaatcct cattggatga ggaagggaaa gggagagtgc    540

taagcagact cacagaactt caggctgaat taagtctgaa aaatttatgg caagttctca    600

taggagaaga agatgttgaa aagggaattg attttaaact tggacaaaca atatctagac    660

taagggatat atctgttcca gctggtttct ccaattttga aggaatgagg agctacatag    720

acaatataga cccaaaagga gcaatagaga gaaatctagc aaggatgtct cccttagtat    780

cagtcacacc taaaaagtta acatgggagg acctaagacc aatagggcct cacatttacg    840

accatgagct accagaagtt ccatataatg cctttcttct aatgtctgat gaactgggat    900

tggccaatat gactgaggga aagtccaaaa aaccgaagac attagccaaa gaatgtctag    960

aaaagtactc aacactacgg gatcaaactg acccaatatt aataatgaaa agcgaaaaag   1020

ctaacgaaaa tttcctatgg aagctttgga gagactgtgt aaatacaata agtaatgagg   1080

aaacgagtaa cgagttacag aaaaccaatt atgccaaatg ggccacaggg gatggattaa   1140

cataccagaa aataatgaaa gaagtagcaa tagatgacga aacaatgtgc caagaagagc   1200

ctaaaatccc taacaaatgt agagtggctg cttgggttca aacagagatg aatctattga   1260

gcactctgac aagtaaaaga gctctggacc taccagaaat agggccagac atagcacccg   1320

tggagcatgt aggaagtgaa agaaggaaat actttgttaa tgaaatcaac tactgtaagg   1380

cctctacagt tatgatgaag tatgtgcttt ttcacacttc attgttgaat gaaagcaatg   1440

ccagcatggg aaaatacaaa gtaataccaa taaccaatag agtagtaaat gaaaaaggag   1500

aaagtttcga catgctttac ggtctggcgg ttaaaggaca atctcatctg aggggagata   1560
```

```
ctgatgttgt aacagttgta actttcgaat ttagtagtac agatccaaga gtggactcag   1620

gaaagtggcc aaaatatact gtgtttagga ttggctccct atttgtgagt gggagggaaa   1680

aatctgtgta cttgtattgc cgagtgaatg gcacaaataa gatccaaatg aaatggggaa   1740

tggaagctag aagatgtttg cttcaatcaa tgcaacaaat ggaggcaatt gttgaacagg   1800

aatcatcaat acaaggatat gacatgacca aagcctgttt caagggagac agagtaaata   1860

gccccaaaac tttcagtatt ggaactcaag aaggaaaact agtaaaagga tcctttggaa   1920

aagcactaag agtaatattt actaaatgct tgatgcacta tgtatttgga aatgcccaat   1980

tggaggggtt tagtgccgag tctaggagac ttctactgtt gattcaagca ttaaaggaca   2040

gaaagggccc ttgggtgttc gacttagagg gaatgtattc tggaatagaa gaatgtatta   2100

gcaacaaccc ttgggtaata cagagtgtat actggttcaa tgaatggttg ggctttgaaa   2160

aggaggggaa taaagtgttg gaatcagtgg atgaaataat ggatgaataa aaggaaatgg   2220

tactcaattt ggtactattt tgttcattat gtatctaaac atccaataaa aagaaccaag   2280

aatcaaaaat gcacgtgttt ctact                                         2305
```

<210> SEQ ID NO 72
<211> LENGTH: 2369
<212> TYPE: DNA
<213> ORGANISM: Influenza virus

<400> SEQUENCE: 72

```
agcagaagcg gagcctttaa gatgaatata aatccttatt ttctcttcat agatgtgccc     60

gtacaggcag caatttcaac aacattccca tacactggtg ttcccccttta ttcccatgga   120

acaggaacag gctacacaat agacaccgtg atcagaacgc atgagtactc aaacaagggg   180

aaacagtaca tttctgatgt tacaggatgc acaatggtag atccaacaaa tggaccatta   240

cccgaagata atgagccgag tgcctatgcg caattagatt gcgttttaga ggctttggat   300

agaatggatg aagaacaccc aggtcttttt caagcagcct cacagaatgc tatggaggcc   360

ctaatggtca caactgtaga caaattaacc caggggagac agacttttga ttggacagta   420

tgcagaaacc aacctgctgc aacggcactg aacacaacaa taacctcttt taggttgaat   480

gatttaaatg gagccgacaa aggtggatta atacctttt gccaggatat cattgattca   540

ttagaccgac ctgaaatgac tttcttctca gtaaagaata taaagaaaaa attgcctgcc   600

aaaaacagaa agggtttcct cataaagagg ataccaatga aggtaaaaga caaaataacc   660

aaagtggaat acatcaaaag agcattatca ttaaacacaa tgacaaaaga cgctgaaaga   720

ggcaaactga aaagaagagc gattgccact gctggaatac aaatcagagg gtttgtatta   780

gtagttgaaa acttggctaa aaatatatgt gaaaatctag aacaaagtgg tttaccagta   840

ggtggaaacg agaagaaagc caaactgtca aacgcagtgg ccaaaatgct cagtaactgc   900

ccaccaggag ggattagcat gacagtaaca ggagacaata caaaatggaa tgaatgttta   960

aacccaagaa tctttttggc tatgactgaa agaataacca gagacagccc agtttggttc  1020

agggattttt gtagtatagc accggtcctg ttctccaata agatagcaag attggggaaa  1080

gggtttatga taacaagcaa aacaaaaaga ctgaaggctc aaataccttg tcctgatctg  1140

tttagtatac cgttagaaag atataatgaa gaaacaaggg caaaattgaa aaagctaaaa  1200

ccattcttca atgaagaagg aactgcatct ttgtcgcctg ggatgatgat gggaatgttt  1260

aatatgctat ctaccgtgtt gggagtagct gcactaggta tcaagaacat tggaaacaaa  1320
```

```
gaatacttat gggatggact gcaatcttct gatgattttg ctctgtttgt taatgcaaag   1380

gatgaagaaa catgtatgga aggaataaac gacttttacc gaacatgtaa attattggga   1440

gtaaacatga gcaaaaagaa aagttactgt aatgagactg gaatgtttga atttacaagc   1500

atgttctaca gagatggatt tgtatctaat tttgcaatgg aactcccttc gtttggggtt   1560

gctggagtaa atgaatcagc agatatggca ataggaatga caataataaa gaacaacatg   1620

atcaacaatg gaatgggtcc ggcaacagca caaacagcca tacagttatt catagctgat   1680

tatagataca cctacaaatg ccacagggga gattccaaag tagaaggaaa gagaatgaaa   1740

atcataaagg agttatggga aaacactaaa ggaagagatg gtctattagt agcagatggt   1800

gggcccaaca tttacaattt gagaaacctg catatcccag aaatagtatt aaagtataat   1860

ctaatggacc ctgaatacaa agggcggtta cttcatcctc aaaatccctt tgtgggacat   1920

ttgtctattg agggcatcaa agaggcagac ataaccccag cacatggtcc agtaaagaaa   1980

atggactacg atgcggtgtc tggaactcat agttggagaa ccaaaagaaa cagatctata   2040

ctaaacactg atcagaggaa catgattctt gaggaacaat gctacgctaa atgttgcaac   2100

ctatttgagg cctgttttaa cagtgcatca tacaggaagc cagtgggtca acatagcatg   2160

cttgaggcta tggcccacag attaagaatg gatgcacgat tagattatga atcagggaga   2220

atgtcaaagg atgattttga gaaagcaatg gctcaccttg gtgagattgg gtacatataa   2280

gcttcgaaga tgtttatggg gttattggtc atcattgaat acatgcgata cacaaatgat   2340

taaaatgaaa aaaggctcgt gtttctact                                    2369
```

```
<210> SEQ ID NO 73
<211> LENGTH: 2396
<212> TYPE: DNA
<213> ORGANISM: Influenza virus

<400> SEQUENCE: 73

agcagaagcg gagcgttttc aagatgacat tggccaaaat tgaattgtta aaacaactgc     60

taagggacaa tgaagccaaa acagttttga agcaaacaac ggtagaccaa tataacataa    120

taagaaaatt caatacatca aggattgaaa agaatccttc actaaggatg aagtgggcca    180

tgtgttctaa ttttcccttg gctctaacca agggcgatat ggcaaacaga atccccttgg    240

aatacaaagg gatacaactt aaaacaaatg ctgaagacat aggaaccaaa ggccaaatgt    300

gctcaatagc agcagttact tggtggaata catatggacc aataggagat actgaaggtt    360

tcgaaagggt ctacgaaagc ttttttctca gaaaaatgag acttgacaac gccacttggg    420

gccgaataac ttttggccca gttgaaagag tgagaaaaag ggtactgcta aaccctctca    480

ccaaggaaat gcctccggat gaggcgagca atgtgataat ggaaatattg ttccctaaag    540

aagcaggaat accaagagaa tccacttgga tacataggga actgataaaa gaaaaaagag    600

aaaaattgaa aggaacaatg ataactccaa tcgtactggc atacatgctt gaaagagaac    660

tggttgctcg aagaagattc ttgccagtgg caggagcaac atcagctgag ttcatagaaa    720

tgctacactg cttacaaggt gaaaattgga gacaaatata tcacccagga gggaataaat    780

taactgagtc caggtctcaa tcaatgatag tagcttgtag aaaaataatc agaagatcaa    840

tagtcgcttc aaacccactg gagctagctg tagaaattgc aaacaagact gtgatagata    900

ctgaaccttt aaagtcatgt ctggcagcca tagacggagg tgatgtagct tgtgacataa    960

taagagctgc attaggacta aagatcagac aaagacaaag atttggacgg cttgagctaa   1020

aaagaatatc aggaagagga ttcaaaaatg atgaagaaat attaataggg aacggaacaa   1080
```

```
tacagaagat tggaatatgg gacggggaag aggagttcca tgtaagatgt ggtgaatgca   1140
ggggaatatt aaaaaagagt aaaatgaaac tggaaaaact actgataaat tcagccaaaa   1200
aggaggatat gagagattta ataatcttat gcatggtatt ttctcaagac actaggatgt   1260
tccaaggagt gagaggagaa ataaattttc ttaatcgagc aggccaactt ttatctccaa   1320
tgtaccaact ccaacgatat tttttgaata gaagcaacga cctttttgat caatgggggt   1380
atgaggaatc acccaaagca agtgaactac atgggataaa tgaatcaatg aatgcatctg   1440
actatacatt gaaagggatt gtagtgacaa gaaatgtaat tgacgacttt agctctattg   1500
aaacagaaaa agtatccata acaaaaaatc ttagtttaat aaaaaggact ggggaagtca   1560
taatgggagc taatgacgtg agtgaattag aatcacaagc acagctgatg ataacatatg   1620
atacacctaa aatgtgggaa atgggaacaa ccaaagaact ggtgcaaaac acttatcaat   1680
gggtgctaaa aaacttggtg acactgaagg ctcagtttct tctaggaaaa gaggacatgt   1740
tccaatggga tgcatttgaa gcatttgaga gcataattcc tcagaagatg gctggtcagt   1800
acagtggatt tgcaagagca gtgctcaaac aaatgagaga ccaggaggtt atgaaaactg   1860
accagttcat aaagttgttg ccttttttgtt tctcaccacc aaaattaagg agcaatgggg   1920
agccttatca attcttaaaa cttgtgttga aaggaggagg ggaaaatttc atcgaagtaa   1980
ggaaagggtc ccctctattt tcctataatc cacaaacaga agtcctaact atatgcggca   2040
gaatgatgtc attaaaaggg aaaattgaag atgaagaaag gaatagatca atgggtaatg   2100
cagtattagc aggctttctc gttagtggca agtatgaccc agatcttgga gatttcaaaa   2160
ctattgaaga acttgaaaag ctgaaaccgg gggaaaaggc aaacatctta ctttatcaag   2220
gaaaaccagt taaagtagtt aaaaggaaaa ggtatagtgc tttgtccaat gacatttcac   2280
aaggaattaa gagacaaaga atgacagttg agtctatggg gtgggccttg agctaatata   2340
aatttatcca ttaattcaat gaacgcaatt gagtgaaaaa tgctcgtgtt tctact       2396
```

<210> SEQ ID NO 74
<211> LENGTH: 1844
<212> TYPE: DNA
<213> ORGANISM: Influenza virus

<400> SEQUENCE: 74

```
agcagaagca cagcattttc ttgtgaactt caagcaccag taaaagaact gaaaatcaaa     60
atgtccaaca tggatattga cggtataaac actgggacaa ttgacaaaac accggaagaa    120
ataacttctg gaaccagtgg gacaaccaga ccaatcatta gaccagcaac ccttgcccca    180
ccaagcaaca aacgaacccg taacccatcc ccggaaagag caaccacaag cagtgaagat    240
gatgtcggaa ggaaaaccca aaagaaacag accccgacag agataaagaa gagcgtctac    300
aacatggtgg tgaaactggg cgaattctat aaccagatga tggtcaaagc tggactcaat    360
gatgacatgg agagaaatct aatccaaaat gcgcatgccg tggaaagaat tctattggct    420
gccactgatg acaagaaaac cgagttccag aagaaaaaga atgccagaga tgtcaaagaa    480
gggaaagaag aaatagatca caacaaaaca ggaggcacct tttacaagat ggtaagagat    540
gataaaacca tctacttcag ccctataaga attacctttt taaaagaaga ggtgaaaaca    600
atgtacaaaa ccaccatggg gagtgatggc ttcagtggac taaatcacat aatgattggg    660
cattcacaga tgaatgatgt ctgtttccaa agatcaaagg cactaaaaag agttggactt    720
gatccttcat taatcagtac ctttgcggga agcacagtcc ccagaagatc aggtgcgact    780
```

```
ggtgttgcaa tcaaaggagg tggaacctta gtggctgaag ccattcgatt tataggaaga    840

gcaatggcag acagagggct attgagagac atcaaagcca agactgccta tgaaaagatt    900

cttctgaatc taaaaaacaa atgctctgcg ccccaacaaa aggctctagt tgatcaagtg    960

atcggaagca gaaatccggg gattgcagac attgaagatc taaccctgct tgctcgtagt   1020

atggtcgttg ttaggccctc tgtggcaagc aaagtggtgc ttcccataag catttacgcc   1080

aaaatacctc aactagggtt caatgttgaa gagtactcta tggttgggta cgaagccatg   1140

gctctttaca atatggcaac acctgtgtcc atattaagaa tgggagatga tgcaaaagat   1200

aaatcgcaat tattcttcat gtcttgcttc ggagctgcct atgaagacct gagagttttg   1260

tctgcattaa caggcacaga attcaagcct agatcagcat taaaatgcaa gggtttccat   1320

gttccagcaa aggaacaggt agaaggaatg ggagcagctc tgatgtccat caagctccag   1380

ttttgggctc cgatgaccag atctgggggg aacgaagtag gtggagacgg agggtctggc   1440

caaataagct gcagcccagt gtttgcagtg gaaagaccta ttgctctaag caagcaagct   1500

gtaagaagaa tgctgtcaat gaatattgag ggacgtgatg cagatgtcaa aggaaatcta   1560

ctcaagatga tgaatgactc aatggctaag aaaaccagtg gaaatgcttt cattgggaag   1620

aaaatgtttc aaatatcaga caaaaacaaa accaatccca ttgaaattcc aattaagcag   1680

accatcccca atttcttctt tgggagggac acagcagagg attatgatga cctcgattat   1740

taaggcaaca aaatagacac tatgactgtg attgtttcaa tacgtttgga atgtgggtgt   1800

ttattcttat taaaataaat ataaaaaatg ctgttgtttc tact                    1844
```

<210> SEQ ID NO 75
<211> LENGTH: 1189
<212> TYPE: DNA
<213> ORGANISM: Influenza virus

<400> SEQUENCE: 75

```
agcagaagca cgcactttct taaaatgtcg ctgtttggag acacaattgc ctacctgctt     60

tcattgacag aagatggaga aggcaaagca gaactagcag aaaaattaca ctgttggttt    120

ggtgggaaag aatttgacct agactctgcc ttggaatgga taaaaaacaa aagatgctta    180

actgatatac aaaaagcact aattggtgcc tctatatgct tttaaaacc caaagaccag     240

gaaagaaaaa gaagattcat cacagagccc ttatcaggaa tgggaacaac agcaacaaaa    300

aagaaaggcc tgattctggc tgagagaaaa atgagaagat gtgtgagctt tcatgaagca    360

tttgaaatag cagaaggcca tgaaagctca gcgctactat actgtctcat ggtcatgtac    420

ctgaatcctg gaaattattc aatgcaagta aaactaggaa cgctctgtgc tttatgcgag    480

aaacaagcat cacattcaca cagggctcat agcagagcag cgagatcttc agtgcctgga    540

gtgagacgag aaatgcagat ggtctcagct atgaacacag caaaaacaat gaatggaatg    600

ggaaaaggag aagacgtcca aaagctggca gaagagttgc aaagcaacat tggagtgctg    660

agatctcttg gggcaagcca aaagaatggg gaagggattg caaaggatgt aatggaagtg    720

ctaaagcaga gctccatggg aaattcagct cttgtgaaga aatatctata atgctcgaac    780

catttcagat tcttacaatt tgttctttta tcttatcagc tctccatttc atggcttgga    840

caatagggca tttgaatcaa ataaaaagag gaataaacat gaaaatacga ataaaaggtc    900

caaacaaaga gacaataaac agagaggtat caattttgag acacagttac caaaaagaaa    960

tccaggccaa agaaacaatg aaggaagtac tctctgacaa catggaggta ttgaatgacc   1020

acataataat tgaggggctt tctgccgaag agataataaa aatgggtgaa acagttttgg   1080
```

agatagaaga attgcattaa attcaatttt actgtatttc ttactatgca tttaagcaaa 1140
ttgtaatcaa tgtcagcaaa taaactggaa aaagtgcgtt gtttctact 1189

<210> SEQ ID NO 76
<211> LENGTH: 1101
<212> TYPE: DNA
<213> ORGANISM: Influenza virus

<400> SEQUENCE: 76
agcagaagca gaggatttgt ttagtcactg gcaaacaggg aaaaatggcg aacaacaaca 60
tgaccacaac acaaattgag gtgggtccgg gagcaaccaa tgccaccata aactttgaag 120
caggaattct agagtgctat gaaaggcttt catggcaaag agcccttgac taccctggtc 180
aagaccgcct aaacagacta aagagaaaat tagagtcaag aataaagact cacaacaaaa 240
gtgagcctga aagtaaaagg atgtcccttg aagagagaaa agcaattgga gtaaaaatga 300
tgaaagtact cctatttatg aatccgtctg ctggaattga agggtttgag ccatactgta 360
tgaaaagttc ctcaaatagc aactgtacga aatacaattg gactgattac ccttcaacac 420
cagagaggtg ccttgatgac atagaggaag aaccagagga tgttgatggc ccaactgaaa 480
tagtattaag ggacatgaac aacaaagatg caaggcaaaa gataaaggag gaagtaaaca 540
ctcagaaaga agggaagttc cgtttgacaa taaaaaggga tatgcgtaat gtattgtcct 600
tgagagtgtt ggtaaacgga acattcctca aacaccccaa tggacacaag tccttatcaa 660
ctctgcatag attgaatgca tatgaccaga gtggaaggct tgttgctaaa cttgttgcca 720
ctgatgatct tacagtggag gatgaagaag atggccatcg gatcctcaac tcactcttcg 780
agcgtcttaa tgaaggacat tcaaagccaa ttcgagcagc tgaaactgcg gtgggagtct 840
tatcccaatt tggtcaagag caccgattat caccagaaga gggagacaat tagactggtc 900
acggaagaac tttatctttt aagtaaaaga attgatgata acatactatt ccacaaaaca 960
gtaatagcta acagctccat aatagctgac atggttgtat cattatcatt attagaaaca 1020
ttgtatgaaa tgaaggatgt ggttgaagtg tacagcaggc agtgcttgtg aatttaaaat 1080
aaaaatcctc ttgttactac t 1101

<210> SEQ ID NO 77
<211> LENGTH: 2305
<212> TYPE: DNA
<213> ORGANISM: Influenza virus

<400> SEQUENCE: 77
agcagaagcg gtgcgtttga tttgccataa tggatacttt tattacaaga aacttccaga 60
ctacaataat acaaaaggcc aaaaacacaa tggcagaatt tagtgaagat cctgaattac 120
aaccagcaat gctattcaac atctgcgtcc atctagaggt ttgctatgta ataagtgaca 180
tgaattttct tgacgaagaa ggaaaatcat atacagcatt agaaggacaa ggaaaagaac 240
aaaacttgag accacaatat gaagtaattg agggaatgcc aagaaccata gcatggatgg 300
tccaaagatc cttagctcaa gagcatggaa tagagactcc aaagtatctg gctgatttgt 360
ttgattataa aaccaagaga tttatagaag ttggaataac aaaaggattg gctgatgatt 420
acttttggaa aaagaaagaa aagctgggaa atagcatgga actgatgata ttcagctaca 480
atcaagacta ttcgttaagt aatgaatcct cattggatga ggaagggaaa gggagagtgc 540
taagcagact cacagaactt caggctgaat taagtctgaa aaacctatgg caagttctca 600

```
taggagaaga agatgttgaa aagggaattg actttaaact tggacaaaca atatctagac    660

taagggatat atctgttcca gctggtttct ccaattttga aggaatgagg agctacatag    720

acaatataga tcctaaagga gcaatagaaa gaaatctagc aaggatgtct cccttagtat    780

cagccacacc taaaaagttg aaatgggagg acctaagacc aatagggcct cacatttaca    840

accatgagtt accagaagtt ccatataatg cctttcttct aatgtctgat gaattggggc    900

tggccaatat gactgaggga aagtccaaaa aaccgaagac attagccaaa gaatgtctag    960

aaaagtactc aacactacgg gatcaaactg acccaatatt aataatgaaa agcgaaaaag   1020

ctaacgaaaa tttcctatgg aagctgtgga gggactgtgt aaatacaata agtaatgagg   1080

aaatgagtaa cgagttacag aaaaccaatt atgccaagtg ggccacagga gatggattaa   1140

cataccagaa aataatgaaa gaagtagcaa tagatgacga aacaatgtgc caagaagagc   1200

ctaaaatccc taacaaatgt agagtggctg cttgggttca aacagagatg aatttattga   1260

gcactctgac aagtaaaaga gctctggacc taccagaaat agggccagac gtagcacccg   1320

tggagcatgt agggagtgaa agaaggaaat actttgttaa tgaaatcaac tgctgtaagg   1380

cctctacagt tatgatgaag tatgtgcttt ttcacacttc attattgaat gaaagcaatg   1440

ccagcatggg aaaatataaa gtaataccaa taaccaatag agtagtaaat gaaaaaggag   1500

aaagtttcga catgctttat ggtctggcgg ttaaaggaca atctcatctg aggggagata   1560

ctgatgttgt aacagttgtg actttcgaat ttagtggtac agatcccaga gtggactcag   1620

gaaagtggcc aaaatatact gtgtttagga ttggctccct atttgtgagt gggagggaaa   1680

aatctgtgta cctatattgc cgagtgaatg gcacaaataa gatccaaatg aaatggggaa   1740

tggaagctag aagatgtctg cttcaatcaa tgcaacaaat ggaagcaatt gttgaacaag   1800

aatcatcgat acaaggatat gacatgacca aagcttgttt caagggagac agagtaaata   1860

gccccaaaac ttttagtatt gggactcaag aaggaaaact agtaaaagga tcctttggga   1920

aagcactaag agtaatattt accaaatgtt tgatgcacta tgtatttgga aatgcccaat   1980

tggaggggtt tagtgccgag tctaggagac ttctactgtt aattcaagca ctaaaggaca   2040

gaaagggccc ttgggtgttc gacttagagg gaatgtattc tggaatagaa gaatgtatta   2100

gtaacaaccc ttgggtaata cagagtgcat actggttcaa tgaatggttg ggctttgaaa   2160

aggaggggag taaagtatta gaatcagtag atgaaataat gaatgaatga aaaaacatag   2220

tactcaattt ggtactattt tgttcattat gtatctaaac atccaataaa aagaatcgag   2280

aatcaaaaat gcacgtgttt ctact                                         2305
```

<210> SEQ ID NO 78
<211> LENGTH: 2369
<212> TYPE: DNA
<213> ORGANISM: Influenza virus

<400> SEQUENCE: 78

```
agcagaagcg gagcctttaa gatgaatata aatccttatt ttctcttcat agatgtaccc     60

atacaggcag caatttcaac aacattccca tacaccggtg ttcccccttta ctcccatgga   120

acgggaacag gccacacaat agacaccgtg atcagaacac atgagtactc gaacaaggga    180

aaacagtatg tttctgacat cacaggatgt acaatggtag atccaacaaa tgggccatta    240

cccgaagaca atgagccgag tgcctatgca caattagatt gcgttctgga ggctttggat    300

agaatggatg aagaacatcc aggtttgttt caagcagcct cacagaatgc catggaggca    360

ctaatggtca caactgtaga caaattaacc caggggagac agacttttga ttggacagta    420
```

```
tgcagaaacc agcctgctgc aacggcacta aacacaacaa taacctcctt taggttgaat    480
gatttgaatg gagctgacaa gggtggattg gtacccttt  gccaagatat cattgattca    540
ttggacaaac ctgaaatgac tttcttctca gtaaagaata taaagaaaaa attgcctgct    600
aaaaacagaa agggtttcct cataaagaga ataccaatga aagtaaaaga caggataacc    660
agagtggaat acatcaaaag agcattatca ttaaacacaa tgacaaaaga tgctgaaagg    720
ggcaaactaa aaagaagagc gattgcaacc gctggaatac aaatcagagg gtttgtatta    780
gtagttgaaa acttggctaa aaatatctgt gaaaatctag aacaaagtgg tttgcccgta    840
ggtggaaatg aaaagaaggc caaactgtca aatgcagtgg ccaaaatgct cagtaactgc    900
ccaccaggag ggatcagcat gacagtaaca ggagacaata ctaaatggaa tgaatgctta    960
aatccaagaa tctttttggc tatgactgaa aggataacaa gagacagccc aatttggttc   1020
cgggattttt gtagtatagc accggtcttg ttctccaata aaatagccag attgggaaaa   1080
ggatttatga taacaagcaa aacaaaaaga ctgaaggctc aaataccttg tccagatctg   1140
tttagcatac cattagaaag atataatgaa gaaacaaggg caaaattaaa aaagctgaaa   1200
ccattcttca atgaagaagg aacggcatct ttgtcgcctg ggatgatgat gggaatgttt   1260
aatatgctat ctaccgtgtt gggagtagcc gcactaggta tcaaaaacat tggaaacaaa   1320
gaatatttat gggatggact gcaatcttct gatgattttg ctctgtttgt taatgcaaaa   1380
gatgaagaga catgtatgga aggaataaac gacttttacc gaacatgtaa attattggga   1440
ataaacatga gcaaaaagaa aagttactgt aatgaaactg gaatgtttga atttacaagc   1500
atgttctata gagatggatt tgtatctaat tttgcaatgg aaattccttc atttggagtt   1560
gctggagtaa atgaatcagc agatatggca ataggaatga caataataaa gaacaatatg   1620
atcaacaatg ggatgggtcc agcaacagca caaacagcca tacaattatt catagctgat   1680
tataggtaca cctacaaatg ccacagggga gattccaaag tggaaggaaa aagaatgaaa   1740
attataaagg agctatggga aaacactaaa ggaagagatg gtctgttagt ggcagatggt   1800
gggcccaaca tttacaattt gagaaactta catatcccag aaatagtatt gaagtacaac   1860
ctaatggacc ctgaatacaa agggcggtta cttcatcctc aaaatccatt tgtaggacat   1920
ttatctattg agggcatcaa agaagcagat ataaccccag cacatggtcc cgtaaagaaa   1980
atggattatg atgcagtatc tggaactcat agttggagaa ccaaaaggaa cagatctata   2040
ctaaatactg accagaggaa catgattctt gaggaacaat gctacgctaa gtgttgcaac   2100
ctttttgagg cctgttttaa tagtgcatca tacaggaaac cagtaggtca gcacagcatg   2160
cttgaggcta tggcccacag attaagagtg gatgcacgac tagattatga atcaggaaga   2220
atgtcaaagg atgattttga gaaagcaatg gctcaccttg gtgagattgg gtacatataa   2280
gctccgaaga tgtctatggg gttattggtc atcattgaat acatgtgata aacaaatgat   2340
taaaatgaaa aaaggctcgt gtttctact                                    2369
```

<210> SEQ ID NO 79
<211> LENGTH: 2396
<212> TYPE: DNA
<213> ORGANISM: Influenza virus

<400> SEQUENCE: 79

```
agcagaagcg gagcgttttc aagatgacat tggctaaaat tgaattgtta aaacaactgt     60
taagggacaa tgaagccaaa acagtattga aacaaacaac ggtagaccaa tataacataa    120
```

```
taagaaaatt caatacatca agaattgaaa agaacccttc attgaggatg aagtgggcaa    180
tgtgttctaa ttttcccttg gctctgacca agggtgatat ggcaaacaga atccccttgg    240
aatacaaggg aatacaactt aaaacaaatg ctgaagacat aggaactaaa ggccaaatgt    300
gctcaatagc agcagttacc tggtggaata catatggacc aataggagat actgaaggtt    360
tcgaaaaggt ctacgaaagc ttttttctca gaaagatgag acttgacaat gccacttggg    420
gccgaataac ttttggccca gttgaaagag taagaaaaag ggtactgcta aaccctctca    480
ccaaggaaat gcctccagat gaagcaagta atgtgataat ggaaatattg ttccctaagg    540
aagcaggaat accaagagaa tctacttgga tacataggga actgataaaa gaaaaaagag    600
aaaaattgaa aggaacaatg ataactccca ttgtactggc atacatgctt gagagagaat    660
tggttgccag aagaaggttc ctgccggtgg caggagcaac atcagctgag ttcatagaaa    720
tgctacactg cttacaaggt gaaaattgga gacaaatata tcacccagga ggaaataaac    780
taactgaatc taggtctcaa tcgatgattg tagcttgtag aaagataatc agaagatcaa    840
tagtcgcatc aaacccatta gagctagctg tagaaattgc aaacaagact gtgatagata    900
ctgaaccttt aaaatcatgt ctgacagcca tagacggagg tgatgtagcc tgtgacataa    960
taagagctgc attaggacta aagatcagac aaagacaaag atttggacga cttgaactaa   1020
agagaatatc aggaagagga ttcaaaaatg atgaagaaat attaatcggg aacggaacaa   1080
tacagaagat tggaatatgg gacggagaag aggagttcca tgtaagatgt ggtgaatgca   1140
ggggaatatt aaaaaagagc aaaatgagaa tggaaaaact actaataaat tcagctaaaa   1200
aggaagacat gaaagattta ataatcttgt gcatggtatt ttctcaagac actaggatgt   1260
tccaaggagt gagaggagaa ataaattttc ttaatagagc aggccaactt ttatctccaa   1320
tgtaccaact ccaaagatat tttttgaata gaagcaacga tctctttgat caatgggggt   1380
atgaggaatc acccaaagca agtgagctac atggaataaa tgaattaatg aatgcatctg   1440
actacacttt gaaaggggtt gtagtaacaa aaaatgtaat tgatgatttt agttctactg   1500
aaacagaaaa agtatctata acaaaaaatc ttagtttaat aaaaaggact ggggaagtca   1560
taatgggggc taatgacgta agtgaattag aatcacaagc tcagctaatg ataacatatg   1620
atacacctaa gatgtgggag atgggaacaa ccaaagaact ggtgcaaaac acctaccaat   1680
gggtgctgaa aaatttggta acactgaagg ctcagtttct tctaggaaaa gaagacatgt   1740
tccaatggga tgcatttgaa gcatttgaaa gcataatccc ccagaagatg gctggccagt   1800
acagtggatt tgcaagagca gtgctcaaac aaatgagaga ccaagaggtt atgaaaactg   1860
accagttcat aaagttgttg cccttttgtt tctcaccacc aaaattaagg agaaatgggg   1920
agccttatca gttcttgagg cttgtattga agggaggagg agaaaatttc atcgaagtaa   1980
ggaaagggtc ccctctattc tcttacaatc cacaaacaga agtcctaact atatgcggca   2040
gaatgatgtc attaaaaggg aaaattgaag atgaagaaag gaatagatca atgggggaatg  2100
cagtattagc gggctttctc gttagtggca agtatgaccc agatcttgga gatttcaaaa   2160
ctattgaaga acttgaaaag ctgaaaccgg gggagaaagc aaacatctta ctttatcaag   2220
gaaagcccgt taaagtagtt aaaaggaaaa gatatagtgc tttatccaat gacatttcac   2280
aaggaattaa gagacaaaga atgacagttg agtccatggg gtgggccttg agctaatata   2340
aatttatcca ttaattcaat aaacacaatt gagtgaaaaa tgctcgtgtt tctact       2396
```

<210> SEQ ID NO 80
<211> LENGTH: 1844

<212> TYPE: DNA
<213> ORGANISM: Influenza virus

<400> SEQUENCE: 80

```
agcagaagca cagcattttc ttattaactt caagtaccaa caaaagaact gaaaatcaaa     60
atgtccaaca tggatattga cggtatcaac actgggacaa ttgacaaaac accggaagaa    120
ataacttctg gaaccagtgg gacaaccaga ccaatcatca gaccagcaac ccttgcccca    180
ccaagcaaca aacgaacccg gaacccatcc ccggaaagag caaccacaag cagtgaagct    240
gatgtcggaa ggaaaaccca aaagaaacag accccgacag agataaagaa gagcgtctac    300
aatatggtag tgaaactggg tgaattctat aaccagatga tggtcaaagc tggactcaac    360
gatgacatgg agagaaacct aatccaaaat gcgcatgctg tggaaagaat tctattggct    420
gccactgatg acaagaaaac tgaattccag aggaaaaaga atgccagaga tgtcaaagaa    480
ggaaaagaag aaatagacca caacaaaaca ggaggcacct tttacaagat ggtaagagat    540
gataaaacca tctacttcag ccctataaga attacctttt taaaagaaga ggtgaaaaca    600
atgtacaaaa ccaccatggg gagtgatggc ttcagtggac taaatcacat aatgattggg    660
cattcacaga tgaatgatgt ctgtttccaa agatcaaagg ccctaaaaag agttggactt    720
gacccttcat taatcagtac ctttgcagga agcacactcc ccagaagatc aggtgcaact    780
ggtgttgcaa tcaaaggagg tggaacttta gtggctgaag ccattcgatt tataggaaga    840
gcaatggcag acagagggct attgagagac atcaaagcca agactgccta tgaaaagatt    900
cttctgaatc taaaaaacaa atgctctgcg ccccaacaaa aggctctagt tgatcaagtg    960
atcggaagta gaaatccagg gattgcagac attgaagacc taaccctgct tgctcgtagt   1020
atggtcgttg ttaggccctc tgtggcgagc aaagtagtgc ttcccataag catttatgct   1080
aaaatacctc aactagggtt caatgttgaa gaatactcta tggttgggta tgaagccatg   1140
gctctctaca atatggcaac acctgtttcc atattaagaa tgggagatga tgcaaaagat   1200
aaatcgcaat tattcttcat gtcttgcttc ggagctgcct atgaagacct gagagttttg   1260
tctgcattaa caggcataga attcaagcct agatcagcat taaaatgcaa gggtttccat   1320
gttccagcaa aggaacaggt ggaaggaatg gggcagctc tgatgtccat caagctccag    1380
ttttgggctc caatgaccag atctggaggg aacgaagtag gtggagacgg agggtctggc   1440
caaataagtt gcagcccagt gtttgcagta gaaagaccta ttgctctaag caagcaagct   1500
gtaagaagaa tgctttcaat gaatattgag ggacgtgatg cagatgtcaa aggaaatcta   1560
ctcaagatga tgaatgactc aatggctaag aaaaccaatg gaaatgcttt cattgggaag   1620
aaaatgtttc aaatatcaga caaaaacaaa accaatcccg ttgaaattcc aattaagcag   1680
accatcccca atttcttctt tgggagggac acagcagagg attatgatga cctcgattat   1740
taaagcaaca aaatagacac tatgactgtg attgtttcaa tacgtttgga atgtgggtgt   1800
ttactcttat tgaaataaat ataaaaaatg ctgttgtttc tact                     1844
```

<210> SEQ ID NO 81
<211> LENGTH: 1190
<212> TYPE: DNA
<213> ORGANISM: Influenza virus

<400> SEQUENCE: 81

```
agcagaagca cgcactttct taaaatgtcg ctgtttggag acacaattgc ctacctgctt     60
tcattgacag aagatggaga aggcaaagca gaactagcag aaaaattaca ctgttggttc    120
```

```
ggtgggaaag aatttgacct agactctgcc ttggaatgga taaaaaacaa aagatgctta    180

actgatatac agaaagcact aattggtgcc tctatctgct tttaaaacc aaaagaccaa    240

gaaagaaaaa gaagattcat cacagagccc ctatcaggaa tgggaacaac agcaacaaaa    300

aagaagggcc tgattctagc tgagagaaaa atgagaagat gtgtgagttt tcatgaagca    360

tttgaaatag cagaaggcca tgaaagctca gcgctactat attgtctcat ggtcatgtac    420

ctgaaccctg gaaattattc aatgcaagta aaactaggaa cgctctgtgc tttgtgcgag    480

aaacaagcat cacattcaca cagggctcat agcagagcag caagatcttc agtgcctgga    540

gtgaggcgag aaatgcagat ggtctcagct atgaacacag caaaaacaat gaatggaatg    600

ggaaagggag aagacgtcca aaaactggca gaagagctgc aaagcaacat tggagtattg    660

agatctcttg ggcaagtca aaagaatggg gaaggaattg caaaggatgt gatggaagtg    720

ctaaagcaga gctctatggg aaattcagct cttgtgaaga aatacctata atgctcgaac    780

catttcagat tctttcaatt tgttctttca tcttatcagc tctccatttc atggcttgga    840

caatagggca tttgaatcaa ataaaaagag gagtaaacat gaaaatacga ataaaaaatc    900

caaataaaga gacaataaac agagaggtat caattttgag acacagttac caaaaagaaa    960

tccaggccaa agaaacaatg aaggaagtac tctctgacaa catggaggta ttgagtgacc   1020

acatagtaat tgaggggctt tctgctgaag agataataaa aatgggtgaa acagttttgg   1080

aggtagaaga attgcattaa attcaatttt tactgtattt cttgctatgc atttaagcaa   1140

attgtaatca atgtcagcaa ataaactgga aaaagtgcgt tgtttctact              1190
```

```
<210> SEQ ID NO 82
<211> LENGTH: 1096
<212> TYPE: DNA
<213> ORGANISM: Influenza virus

<400> SEQUENCE: 82
```

```
agcagaagca gaggatttgt ttagtcactg gcaaacgaaa aaatggcgga caacatgacc     60

acaacacaaa ttgaggtggg tccgggagca accaatgcca ccataaactt tgaagcagga    120

attttggagt gctatgaaag gctttcatgg caaagagccc ttgactaccc tggtcaagac    180

cgcctaaaca aactaaagag aaaattggaa tcaagaataa agactcacaa caaaagtgag    240

ccagaaagta aaaggatgtc tcttgaagag agaaaagcta ttggggtaaa aatgatgaaa    300

gtgctcctat ttatgaaccc atctgctgga gttgaagggt ttgagccata ttgtatgaaa    360

aatccctcca atagcaactg tccagactgc aattgggctg attaccctcc aacaccagga    420

aagtaccttg atggcataga agaagaaccg gagaatgttg gtgactcaac tgaaatagta    480

ttaagggaca tgaacaacaa agatgcaagg caaaagataa aagaggaagt aaacactcag    540

aaagaaggga aattccgttt gacaataaaa agggatatac gtaatgtgtt gtccttgaga    600

gtgttggtaa acggaacatt catcaagcac cctaatggat acaagtcctt atcaactctg    660

catagattga atgcatatga ccagagtgga agacttgttg ctaaacttgt tgctactgat    720

gatcttacag tggaggatga agaagatggc catcggatcc tcaactcact cttcgagcgt    780

cttaatgaag gacattcaaa gccaattcga gcagctgaaa ctgcggtggg agtcttatcc    840

caatttggtc aagagcaccg attatcacca gaagagagag acaattagac tggttacgga    900

agaactttat cttttaagta aaagaattga tgataacata ttgttccaca aaacagtaat    960

agccaacagc tccataatag ctgacatgat tgtatcatta tcattattgg aaacattgta   1020

tgaaatgaag gatgtggttg aagtgtacag caggcagtgc ttgtgaattt aaaataaaaa   1080
```

```
tcctcttgtt actact                                                  1096

<210> SEQ ID NO 83
<211> LENGTH: 726
<212> TYPE: PRT
<213> ORGANISM: Influenza virus

<400> SEQUENCE: 83

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Ala Tyr Thr Ala Leu
    50                  55                  60

Glu Gly Gln Gly Lys Glu Gln Asn Leu Arg Pro Gln Tyr Glu Val Ile
65                  70                  75                  80

Glu Gly Met Pro Arg Thr Ile Ala Trp Met Val Gln Arg Ser Leu Ala
                85                  90                  95

Gln Glu His Gly Ile Glu Thr Pro Lys Tyr Leu Ala Asp Leu Phe Asp
            100                 105                 110

Tyr Lys Thr Lys Arg Phe Ile Glu Val Gly Ile Thr Lys Gly Leu Ala
        115                 120                 125

Asp Asp Tyr Phe Trp Lys Lys Lys Glu Lys Leu Gly Asn Ser Met Glu
    130                 135                 140

Leu Met Ile Phe Ser Tyr Asn Gln Asp Tyr Ser Leu Ser Asn Glu Ser
145                 150                 155                 160

Ser Leu Asp Glu Glu Gly Lys Gly Arg Val Leu Ser Arg Leu Thr Glu
                165                 170                 175

Leu Gln Ala Glu Leu Ser Leu Lys Asn Leu Trp Gln Val Leu Ile Gly
            180                 185                 190

Glu Glu Asp Val Glu Lys Gly Ile Asp Phe Lys Leu Gly Gln Thr Ile
        195                 200                 205

Ser Arg Leu Arg Asp Ile Ser Val Pro Ala Gly Phe Ser Asn Phe Glu
    210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Val Thr Pro Lys Lys
                245                 250                 255

Leu Thr Trp Glu Asp Leu Arg Pro Ile Gly Pro His Ile Tyr Asp His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Thr
            340                 345                 350

Ser Asn Glu Leu Gln Lys Thr Asn Tyr Ala Lys Trp Ala Thr Gly Asp
        355                 360                 365
```

```
Gly Leu Thr Tyr Gln Lys Ile Met Lys Glu Val Ala Ile Asp Asp Glu
    370                 375                 380

Thr Met Cys Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Ile Ala Pro Val Glu
            420                 425                 430

His Val Gly Ser Glu Arg Arg Lys Tyr Phe Val Asn Glu Ile Asn Tyr
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
            500                 505                 510

Val Val Thr Val Val Thr Phe Glu Phe Ser Ser Thr Asp Pro Arg Val
        515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Val Tyr Trp Phe Asn
    690                 695                 700

Glu Trp Leu Gly Phe Glu Lys Glu Gly Asn Lys Val Leu Glu Ser Val
705                 710                 715                 720

Asp Glu Ile Met Asp Glu
                725


<210> SEQ ID NO 84
<211> LENGTH: 752
<212> TYPE: PRT
<213> ORGANISM: Influenza virus

<400> SEQUENCE: 84

Met Asn Ile Asn Pro Tyr Phe Leu Phe Ile Asp Val Pro Val Gln Ala
```

-continued

```
1               5                   10                  15

Ala Ile Ser Thr Thr Phe Pro Tyr Thr Gly Val Pro Pro Tyr Ser His
            20                  25                  30

Gly Thr Gly Thr Gly Tyr Thr Ile Asp Thr Val Ile Arg Thr His Glu
        35                  40                  45

Tyr Ser Asn Lys Gly Lys Gln Tyr Ile Ser Asp Val Thr Gly Cys Thr
    50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Ile Pro Phe Cys Gln Asp Ile Ile Asp Ser Leu Asp Arg
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Lys Ile Thr Lys Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Val Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430
```

```
Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Val Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Leu Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
                725                 730                 735

Asp Asp Phe Glu Lys Ala Met Ala His Leu Gly Glu Ile Gly Tyr Ile
            740                 745                 750
```

<210> SEQ ID NO 85
<211> LENGTH: 770
<212> TYPE: PRT
<213> ORGANISM: Influenza virus

<400> SEQUENCE: 85

```
Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
            20                  25                  30

Ile Arg Lys Phe Asn Thr Ser Arg Ile Glu Lys Asn Pro Ser Leu Arg
        35                  40                  45

Met Lys Trp Ala Met Cys Ser Asn Phe Pro Leu Ala Leu Thr Lys Gly
```

```
    50                  55                  60

Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
                85                  90                  95

Ala Val Thr Trp Trp Asn Thr Tyr Gly Pro Ile Gly Asp Thr Glu Gly
            100                 105                 110

Phe Glu Arg Val Tyr Glu Ser Phe Phe Leu Arg Lys Met Arg Leu Asp
        115                 120                 125

Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160

Ala Ser Asn Val Ile Met Glu Ile Leu Phe Pro Lys Glu Ala Gly Ile
                165                 170                 175

Pro Arg Glu Ser Thr Trp Ile His Arg Glu Leu Ile Lys Glu Lys Arg
            180                 185                 190

Glu Lys Leu Lys Gly Thr Met Ile Thr Pro Ile Val Leu Ala Tyr Met
        195                 200                 205

Leu Glu Arg Glu Leu Val Ala Arg Arg Arg Phe Leu Pro Val Ala Gly
    210                 215                 220

Ala Thr Ser Ala Glu Phe Ile Glu Met Leu His Cys Leu Gln Gly Glu
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Ala Ala Ile Asp
    290                 295                 300

Gly Gly Asp Val Ala Cys Asp Ile Ile Arg Ala Ala Leu Gly Leu Lys
305                 310                 315                 320

Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Lys Leu Glu
    370                 375                 380

Lys Leu Leu Ile Asn Ser Ala Lys Lys Glu Asp Met Arg Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Asn Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Ser Met Asn Ala Ser Asp Tyr Thr Leu Lys Gly Ile Val
465                 470                 475                 480
```

```
Val Thr Arg Asn Val Ile Asp Asp Phe Ser Ser Ile Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
        595                 600                 605

Val Met Lys Thr Asp Gln Phe Ile Lys Leu Leu Pro Phe Cys Phe Ser
    610                 615                 620

Pro Pro Lys Leu Arg Ser Asn Gly Glu Pro Tyr Gln Phe Leu Lys Leu
625                 630                 635                 640

Val Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735

Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
        755                 760                 765

Leu Ser
    770


<210> SEQ ID NO 86
<211> LENGTH: 560
<212> TYPE: PRT
<213> ORGANISM: Influenza virus

<400> SEQUENCE: 86

Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Asp Asp Val Gly Arg
    50                  55                  60

Lys Thr Gln Lys Lys Gln Thr Pro Thr Glu Ile Lys Lys Ser Val Tyr
```

```
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Val Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495
```

```
Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
        515                 520                 525

Asn Lys Thr Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 87
<211> LENGTH: 248
<212> TYPE: PRT
<213> ORGANISM: Influenza virus

<400> SEQUENCE: 87

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 88
<211> LENGTH: 109
<212> TYPE: PRT
<213> ORGANISM: Influenza virus

<400> SEQUENCE: 88

Met Leu Glu Pro Phe Gln Ile Leu Thr Ile Cys Ser Phe Ile Leu Ser
1               5                   10                  15
```

```
Ala Leu His Phe Met Ala Trp Thr Ile Gly His Leu Asn Gln Ile Lys
            20                  25                  30

Arg Gly Ile Asn Met Lys Ile Arg Ile Lys Gly Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
65                  70                  75                  80

Leu Asn Asp His Ile Ile Ile Glu Gly Leu Ser Ala Glu Glu Ile Ile
                85                  90                  95

Lys Met Gly Glu Thr Val Leu Glu Ile Glu Glu Leu His
            100                 105
```

```
<210> SEQ ID NO 89
<211> LENGTH: 282
<212> TYPE: PRT
<213> ORGANISM: Influenza virus

<400> SEQUENCE: 89

Met Ala Asn Asn Asn Met Thr Thr Thr Gln Ile Glu Val Gly Pro Gly
1               5                   10                  15

Ala Thr Asn Ala Thr Ile Asn Phe Glu Ala Gly Ile Leu Glu Cys Tyr
            20                  25                  30

Glu Arg Leu Ser Trp Gln Arg Ala Leu Asp Tyr Pro Gly Gln Asp Arg
        35                  40                  45

Leu Asn Arg Leu Lys Arg Lys Leu Glu Ser Arg Ile Lys Thr His Asn
    50                  55                  60

Lys Ser Glu Pro Glu Ser Lys Arg Met Ser Leu Glu Glu Arg Lys Ala
65                  70                  75                  80

Ile Gly Val Lys Met Met Lys Val Leu Leu Phe Met Asn Pro Ser Ala
                85                  90                  95

Gly Ile Glu Gly Phe Glu Pro Tyr Cys Met Lys Ser Ser Ser Asn Ser
            100                 105                 110

Asn Cys Thr Lys Tyr Asn Trp Thr Asp Tyr Pro Ser Thr Pro Glu Arg
        115                 120                 125

Cys Leu Asp Asp Ile Glu Glu Glu Pro Glu Asp Val Asp Gly Pro Thr
    130                 135                 140

Glu Ile Val Leu Arg Asp Met Asn Asn Lys Asp Ala Arg Gln Lys Ile
145                 150                 155                 160

Lys Glu Glu Val Asn Thr Gln Lys Glu Gly Lys Phe Arg Leu Thr Ile
                165                 170                 175

Lys Arg Asp Met Arg Asn Val Leu Ser Leu Arg Val Leu Val Asn Gly
            180                 185                 190

Thr Phe Leu Lys His Pro Asn Gly His Lys Ser Leu Ser Thr Leu His
        195                 200                 205

Arg Leu Asn Ala Tyr Asp Gln Ser Gly Arg Leu Val Ala Lys Leu Val
    210                 215                 220

Ala Thr Asp Asp Leu Thr Val Glu Asp Glu Glu Asp Gly His Arg Ile
225                 230                 235                 240

Leu Asn Ser Leu Phe Glu Arg Leu Asn Glu Gly His Ser Lys Pro Ile
                245                 250                 255

Arg Ala Ala Glu Thr Ala Val Gly Val Leu Ser Gln Phe Gly Gln Glu
            260                 265                 270

His Arg Leu Ser Pro Glu Glu Gly Asp Asn
```

```
        275                 280


<210> SEQ ID NO 90
<211> LENGTH: 123
<212> TYPE: PRT
<213> ORGANISM: Influenza virus

<400> SEQUENCE: 90

Met Ala Asn Asn Asn Met Thr Thr Thr Gln Ile Glu Trp Arg Met Lys
1               5                   10                  15

Lys Met Ala Ile Gly Ser Ser Thr His Ser Ser Ser Val Leu Met Lys
            20                  25                  30

Asp Ile Gln Ser Gln Phe Glu Gln Leu Lys Leu Arg Trp Glu Ser Tyr
        35                  40                  45

Pro Asn Leu Val Lys Ser Thr Asp Tyr His Gln Lys Arg Glu Thr Ile
    50                  55                  60

Arg Leu Val Thr Glu Glu Leu Tyr Leu Leu Ser Lys Arg Ile Asp Asp
65                  70                  75                  80

Asn Ile Leu Phe His Lys Thr Val Ile Ala Asn Ser Ser Ile Ile Ala
                85                  90                  95

Asp Met Val Val Ser Leu Ser Leu Leu Glu Thr Leu Tyr Glu Met Lys
            100                 105                 110

Asp Val Val Glu Val Tyr Ser Arg Gln Cys Leu
        115                 120


<210> SEQ ID NO 91
<211> LENGTH: 726
<212> TYPE: PRT
<213> ORGANISM: Influenza virus

<400> SEQUENCE: 91

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Ser Tyr Thr Ala Leu
    50                  55                  60

Glu Gly Gln Gly Lys Glu Gln Asn Leu Arg Pro Gln Tyr Glu Val Ile
65                  70                  75                  80

Glu Gly Met Pro Arg Thr Ile Ala Trp Met Val Gln Arg Ser Leu Ala
                85                  90                  95

Gln Glu His Gly Ile Glu Thr Pro Lys Tyr Leu Ala Asp Leu Phe Asp
            100                 105                 110

Tyr Lys Thr Lys Arg Phe Ile Glu Val Gly Ile Thr Lys Gly Leu Ala
        115                 120                 125

Asp Asp Tyr Phe Trp Lys Lys Lys Glu Lys Leu Gly Asn Ser Met Glu
    130                 135                 140

Leu Met Ile Phe Ser Tyr Asn Gln Asp Tyr Ser Leu Ser Asn Glu Ser
145                 150                 155                 160

Ser Leu Asp Glu Glu Gly Lys Gly Arg Val Leu Ser Arg Leu Thr Glu
                165                 170                 175

Leu Gln Ala Glu Leu Ser Leu Lys Asn Leu Trp Gln Val Leu Ile Gly
            180                 185                 190

Glu Glu Asp Val Glu Lys Gly Ile Asp Phe Lys Leu Gly Gln Thr Ile
```

```
        195                 200                 205

Ser Arg Leu Arg Asp Ile Ser Val Pro Ala Gly Phe Ser Asn Phe Glu
    210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Ala Thr Pro Lys Lys
                245                 250                 255

Leu Lys Trp Glu Asp Leu Arg Pro Ile Gly Pro His Ile Tyr Asn His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Met
            340                 345                 350

Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
    370                 375                 380

Thr Met Cys Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Val Ala Pro Val Glu
            420                 425                 430

His Val Gly Ser Glu Arg Arg Lys Tyr Phe Val Asn Glu Ile Asn Cys
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
            500                 505                 510

Val Val Thr Val Val Thr Phe Glu Phe Ser Gly Thr Asp Pro Arg Val
        515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620
```

```
Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Ala Tyr Trp Phe Asn
    690                 695                 700

Glu Trp Leu Gly Phe Glu Lys Glu Gly Ser Lys Val Leu Glu Ser Val
705                 710                 715                 720

Asp Glu Ile Met Asn Glu
                725


<210> SEQ ID NO 92
<211> LENGTH: 752
<212> TYPE: PRT
<213> ORGANISM: Influenza virus

<400> SEQUENCE: 92

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly His Thr Ile Asp Thr Val Ile Arg Thr His Glu
        35                  40                  45

Tyr Ser Asn Lys Gly Lys Gln Tyr Val Ser Asp Ile Thr Gly Cys Thr
    50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Lys
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Arg Ile Thr Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
```

```
            260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Ile Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685
```

```
Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Val Asp Ala Arg Leu Asp Tyr Glu Ser Gly Arg Met Ser Lys
                725                 730                 735

Asp Asp Phe Glu Lys Ala Met Ala His Leu Gly Glu Ile Gly Tyr Ile
            740                 745                 750


<210> SEQ ID NO 93
<211> LENGTH: 770
<212> TYPE: PRT
<213> ORGANISM: Influenza virus

<400> SEQUENCE: 93

Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
            20                  25                  30

Ile Arg Lys Phe Asn Thr Ser Arg Ile Glu Lys Asn Pro Ser Leu Arg
        35                  40                  45

Met Lys Trp Ala Met Cys Ser Asn Phe Pro Leu Ala Leu Thr Lys Gly
    50                  55                  60

Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
                85                  90                  95

Ala Val Thr Trp Trp Asn Thr Tyr Gly Pro Ile Gly Asp Thr Glu Gly
            100                 105                 110

Phe Glu Lys Val Tyr Glu Ser Phe Phe Leu Arg Lys Met Arg Leu Asp
        115                 120                 125

Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160

Ala Ser Asn Val Ile Met Glu Ile Leu Phe Pro Lys Glu Ala Gly Ile
                165                 170                 175

Pro Arg Glu Ser Thr Trp Ile His Arg Glu Leu Ile Lys Glu Lys Arg
            180                 185                 190

Glu Lys Leu Lys Gly Thr Met Ile Thr Pro Ile Val Leu Ala Tyr Met
        195                 200                 205

Leu Glu Arg Glu Leu Val Ala Arg Arg Arg Phe Leu Pro Val Ala Gly
    210                 215                 220

Ala Thr Ser Ala Glu Phe Ile Glu Met Leu His Cys Leu Gln Gly Glu
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Thr Ala Ile Asp
    290                 295                 300

Gly Gly Asp Val Ala Cys Asp Ile Ile Arg Ala Ala Leu Gly Leu Lys
```

```
305                 310                 315                 320

Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Arg Met Glu
    370                 375                 380

Lys Leu Leu Ile Asn Ser Ala Lys Lys Glu Asp Met Lys Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Asn Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Leu Met Asn Ala Ser Asp Tyr Thr Leu Lys Gly Val Val
465                 470                 475                 480

Val Thr Lys Asn Val Ile Asp Asp Phe Ser Ser Thr Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
        595                 600                 605

Val Met Lys Thr Asp Gln Phe Ile Lys Leu Leu Pro Phe Cys Phe Ser
    610                 615                 620

Pro Pro Lys Leu Arg Arg Asn Gly Glu Pro Tyr Gln Phe Leu Arg Leu
625                 630                 635                 640

Val Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735
```

```
Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
        755                 760                 765

Leu Ser
    770


<210> SEQ ID NO 94
<211> LENGTH: 560
<212> TYPE: PRT
<213> ORGANISM: Influenza virus

<400> SEQUENCE: 94

Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Ala Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Arg Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
```

```
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Ile Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
        515                 520                 525

Asn Lys Thr Asn Pro Val Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 95
<211> LENGTH: 248
<212> TYPE: PRT
<213> ORGANISM: Influenza virus

<400> SEQUENCE: 95

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140
```

```
Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 96
<211> LENGTH: 109
<212> TYPE: PRT
<213> ORGANISM: Influenza virus

<400> SEQUENCE: 96

Met Leu Glu Pro Phe Gln Ile Leu Ser Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Val Asn Met Lys Ile Arg Ile Lys Asn Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
65                  70                  75                  80

Leu Ser Asp His Ile Val Ile Glu Gly Leu Ser Ala Glu Glu Ile Ile
                85                  90                  95

Lys Met Gly Glu Thr Val Leu Glu Val Glu Glu Leu His
            100                 105


<210> SEQ ID NO 97
<211> LENGTH: 281
<212> TYPE: PRT
<213> ORGANISM: Influenza virus

<400> SEQUENCE: 97

Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Lys Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asn Pro Ser Ala Gly
                85                  90                  95

Val Glu Gly Phe Glu Pro Tyr Cys Met Lys Asn Pro Ser Asn Ser Asn
            100                 105                 110
```

```
Cys Pro Asp Cys Asn Trp Ala Asp Tyr Pro Pro Thr Pro Gly Lys Tyr
        115                 120                 125

Leu Asp Gly Ile Glu Glu Glu Pro Glu Asn Val Gly Asp Ser Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Ile Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Arg Asp Asn
        275                 280


<210> SEQ ID NO 98
<211> LENGTH: 122
<212> TYPE: PRT
<213> ORGANISM: Influenza virus

<400> SEQUENCE: 98

Met Ala Asp Asn Met Thr Thr Thr Gln Ile Glu Trp Arg Met Lys Lys
1               5                   10                  15

Met Ala Ile Gly Ser Ser Thr His Ser Ser Ser Val Leu Met Lys Asp
            20                  25                  30

Ile Gln Ser Gln Phe Glu Gln Leu Lys Leu Arg Trp Glu Ser Tyr Pro
        35                  40                  45

Asn Leu Val Lys Ser Thr Asp Tyr His Gln Lys Arg Glu Thr Ile Arg
    50                  55                  60

Leu Val Thr Glu Glu Leu Tyr Leu Leu Ser Lys Arg Ile Asp Asp Asn
65                  70                  75                  80

Ile Leu Phe His Lys Thr Val Ile Ala Asn Ser Ser Ile Ile Ala Asp
                85                  90                  95

Met Ile Val Ser Leu Ser Leu Leu Glu Thr Leu Tyr Glu Met Lys Asp
            100                 105                 110

Val Val Glu Val Tyr Ser Arg Gln Cys Leu
        115                 120


<210> SEQ ID NO 99
<211> LENGTH: 469
<212> TYPE: PRT
<213> ORGANISM: Influenza virus

<400> SEQUENCE: 99

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30
```

```
Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
```

450 455 460

Phe Thr Ile Asp Lys
465

<210> SEQ ID NO 100
<211> LENGTH: 1812
<212> TYPE: DNA
<213> ORGANISM: Influenza virus

<400> SEQUENCE: 100

```
agcattttct tgtgagcttc gagcactaat aaaactgaaa atcaaaatgt ccaacatgga      60
tattgacagt ataaataccg gaacaatcga taaaaaacca gaagaactga ctcccggaac     120
cagtggggca accagaccaa tcatcaagcc agcaaccctt gctccgccaa gcaacaaacg     180
aacccgaaat ccatccccag aaaggacaac cacaagcagt gaaaccgata tcggaaggaa     240
aatccaaaag aaacaaaccc caacagagat aaagaagagc gtctacaaca tggtggtaaa     300
gctgggtgaa ttctacaacc agatgatggt caaagctgga cttaatgatg acatggaaag     360
gaatctaatc caaaatgcac aagctgtgga gagaatccta ttggctgcaa ctgatgacaa     420
gaaaactgaa taccaaaaga aaaggaatgc cagagatgtc aaagaaggga aggaagaaat     480
agaccacaac aagacaggag gcacctttta taagatggta agagatgata aaaccatcta     540
cttcagccct ataaaaatta cctttttaaa agaagaggtg aaaacaatgt acaagaccac     600
catggggagt gatggtttca gtggactaaa tcacattatg attggacatt cacagatgaa     660
cgatgtctgt ttccaaagat caaaggcact gaaaagggtt ggacttgacc cttcattaat     720
cagtactttt gccggaagca cactacccag aagatcaggt acaactggtg ttgcaatcaa     780
aggaggtgga actttagtgg cagaagccat tcgattttata ggaagagcaa tggcagacag     840
agggctactg agagacatca aggccaagac agcctatgaa aagattcttc tgaatctgaa     900
aaacaagtgc tctgcgcccc aacaaaaggc tctagttgat caagtgatcg gaagtaggaa     960
cccagggatt gcagacatag aagacctaac tctgcttgcc agaagcatga tagttgtcag    1020
accctctgta gcgagcaaag tggtgcttcc cataagcatt tatgctaaaa tacctcaact    1080
aggattcaat atcgaagaat actctatggt tgggtatgaa gccatggctc tttataatat    1140
ggcaacacct gtttccatat taagaatggg agatgacgca aaagataaat ctcaactatt    1200
cttcatgtcg tgcttcggag ctgcctatga agatctaaga gtgttatctg cactaacggg    1260
caccgaattt aagcctagat cagcactaaa atgcaagggt ttccatgtcc cggctaagga    1320
gcaagtagaa ggaatggggg cagctctgat gtccatcaag cttcagttct gggccccaat    1380
gaccagatct ggagggaatg aagtaagtgg agaaggaggg tctggtcaaa taagttgcag    1440
ccctgtgttt gcagtagaaa gacctattgc tctaagcaag caagctgtaa gaagaatgct    1500
gtcaatgaac gttgaaggac gtgatgcaga tgtcaaagga aatctactca aaatgatgaa    1560
tgattcgatg gcaaagaaaa ccagtggaaa tgctttcatt gggaagaaaa tgtttcaaat    1620
atcagacaaa aacaaagtca atcccattga gattccaatt aagcagacca tccccagttt    1680
cttctttggg agggacacag cagaggatta tgatgacctc gattattaaa gcaataaaat    1740
agacactatg gctgtgactg tttcagtacg tttgggatgt gggtgtttac tcttattgaa    1800
ataaatgtaa aa                                                        1812
```

<210> SEQ ID NO 101
<211> LENGTH: 560
<212> TYPE: PRT

<213> ORGANISM: Influenza virus

<400> SEQUENCE: 101

```
Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Ala Thr Arg Pro Ile
            20                  25                  30

Ile Lys Pro Ala Thr Leu Ala Pro Pro Ser Asn Lys Arg Thr Arg Asn
        35                  40                  45

Pro Ser Pro Glu Arg Ala Thr Thr Ser Ser Glu Ala Ile Val Gly Arg
    50                  55                  60

Arg Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Tyr Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Arg
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Asn Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Gln Arg Val Leu
385                 390                 395                 400
```

```
Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
        515                 520                 525

Asn Lys Ile Asn Pro Val Asp Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 102
<211> LENGTH: 560
<212> TYPE: PRT
<213> ORGANISM: Influenza virus

<400> SEQUENCE: 102

Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Ala Thr Arg Pro Ile
            20                  25                  30

Ile Lys Pro Ala Thr Leu Ala Pro Pro Ser Asn Lys Arg Thr Arg Asn
        35                  40                  45

Pro Ser Pro Glu Arg Ala Ala Thr Ser Ser Glu Ala Asp Val Gly Arg
    50                  55                  60

Arg Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Ala Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220
```

```
Ile Ser Thr Phe Ala Gly Ser Thr Leu Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Arg
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Asn Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Gln Arg Val Leu
385                 390                 395                 400

Ser Ala Leu Thr Gly Thr Glu Phe Lys His Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Thr Lys Lys Thr
            500                 505                 510

Asn Gly Asn Ala Phe Ile Gly Lys Lys Met Phe Gln Ile Ser Asp Lys
        515                 520                 525

Asn Lys Thr Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560
```

```
<210> SEQ ID NO 103
<211> LENGTH: 1842
<212> TYPE: DNA
<213> ORGANISM: Influenza virus

<400> SEQUENCE: 103

agcagaagca cagcattttc ttgtgaactt caagtaccaa caaaaactga aaatcaaaat     60

gtccaacatg gatattgacg gcatcaacac tggaacaatt gacaaaacac cagaagaaat    120

aacttccgga accagtgggg caaccagacc aatcatcaag ccagcaaccc ttgccccacc    180

aagcaataaa cgaacccgaa acccatcccc agaaagggca accacaagca gcgaagcgat    240
```

```
tgtcggaagg agaacccaaa agaaacaaac cccgacagag ataaagaaga gcgtctacaa    300
tatggtagtg aaactgggtg aattctacaa ccagatgatg gtcaaagctg gactcaacga    360
tgacatggag agaaacctaa tccaaaatgc acatgctgtg gaaagaattc tattggctgc    420
tactgatgac aagaaaactg aataccaaaa gaaaaagaat gccagagatg tcaaagaagg    480
gaaagaagaa atagaccaca acaaaacagg aggcaccttt tataagatgg taagagatga    540
taaaaccatc tacttcagcc ctataagaat taccttttta aaagaagagg tgaaaacaat    600
gtacaagacc accatgggga gtgatggttt cagtggacta aatcacatca tgattgggca    660
ttcacagatg aacgatgtct gtttccaaag atcaaaggca ctaaaaagag ttggacttga    720
cccttcatta atcagtactt ttgcaggaag cacactcccc agaagatcag gtgcaactgg    780
tgttgcgatc aaaggaggtg gaactttagt ggcagaagcc attcgattta taggaagagc    840
aatggcagac agagggctat tgagagacat cagagccaag acggcctatg aaaagattct    900
tctgaatctg aaaaacaagt gctctgcgcc ccaacaaaag gctctagttg atcaagtgat    960
cggaagtaga aacccaggga ttgcagacat agaagaccta accctgcttg cccgaagcat   1020
ggtcgttgtc aggccctctg tagcgagcaa agtggtgctt cccataagca ttaatgctaa   1080
aatacctcaa ctagggttca atgttgaaga atactctatg gttgggtatg aagccatggc   1140
tctttataat atggcaacac ctgtttccat attaagaatg ggagacgatg caaaagataa   1200
atcacaatta ttcttcatgt cttgctttgg agctgcctat gaagaccaaa gagttttgtc   1260
tgcactaacc ggcacagaat tcaagcctag gtcagcatta aagtgcaagg gtttccacgt   1320
tccagcaaag gagcaagtgg aaggaatggg ggcagctctg atgtccatca agctccagtt   1380
ttgggcccca atgaccagat ctggggggaa cgaagtaggt ggagacggag ggtctggtca   1440
aataagttgc agccccgtgt ttgcagtaga gagacctatt gctctaagca agcaagctgt   1500
aagaagaatg ctgtcaatga atattgaggg acgtgatgca gatgtcaaag gaaatctact   1560
caagatgatg aatgattcaa tggctaagaa aaccaatgga aatgctttca ttgggaagaa   1620
aatgtttcaa atatcagaca aaaacaaaat caatcccgtt gatattccaa ttaagcagac   1680
catccccaat ttcttctttg ggagggacac agcagaggat tatgatgacc tcgattatta   1740
aagcaacaaa atagacacta tggctgtgac tgtttcagta cgtttggaat gtgggtgttt   1800
actcttattg aaataaatgt aaaaaatgct gttgtttcta ct                      1842
```

<210> SEQ ID NO 104
<211> LENGTH: 1842
<212> TYPE: DNA
<213> ORGANISM: Influenza virus

<400> SEQUENCE: 104

```
agcagaagca cagcattttc ttgtgaactt caagtaccaa caaaaactga aaatcaaaat     60
gtccaacatg gatattgacg gcatcaacac tggaacaatt gacaaaacac cagaagaaat    120
aacttccgga accagtgggg caaccagacc aatcatcaaa ccagcaaccc ttgccccacc    180
aagcaacaaa cgaacccgaa acccatcccc ggaaagggca gccacaagca gtgaagctga    240
tgtcggaagg agaacccaaa agaaacaaac cccgacagag ataaagaaga gcgtctacaa    300
tatggtagtg aaactgggtg aattctacaa ccagatgatg gtcaaagctg gactcaacga    360
tgacatggag agaaacctaa tccaaaatgc acatgctgcg gaaagaattc tattggctgc    420
tactgatgac aagaaaactg aattccaaaa gaaaaagaat gccagagatg tcaaagaagg    480
```

```
gaaagaagaa atagaccaca acaaaacagg aggcaccttt tacaagatgg taagagatga    540
taaaaccatc tacttcagcc ctataagaat taccttttta aaagaagagg tgaaaacaat    600
gtacaaaacc accatgggga gtgatggttt cagtggacta aatcacatca tgattgggca    660
ttcacagatg aacgatgtct gtttccaaag atcaaaggca ctaaaaagag ttggacttga    720
cccttcatta atcagtactt ttgcaggaag cacactcccc agaagatcag gtgcaactgg    780
tgttgcgatc aaaggaggtg gaactttagt ggcagaagcc attcgattta taggaagagc    840
aatggcagac agagggctat tgagagacat cagagccaag acggcctatg aaaagattct    900
tctgaatctg aaaaacaagt gctctgcgcc ccaacaaaag gctctagttg atcaagtgat    960
cggaagtaga aatccaggga ttgcagacat agaagaccta accctgcttg cccgaagcat   1020
ggtcgttgtc aggccctctg tagcgagcaa agtggtgctt cccataagca ttaatgccaa   1080
aatacctcaa ctagggttca atgttgaaga atactctatg gttgggtatg aagccatggc   1140
tctttataat atggcaacac ctgtttccat attaagaatg ggagacgatg caaaagataa   1200
atcacaatta ttcttcatgt cttgcttcgg agctgcctat gaagaccaaa gagttttgtc   1260
tgcactaaca ggcacagaat tcaagcatag gtcagcatta aagtgcaagg gtttccacgt   1320
tccagcaaag gagcaagtgg aaggaatggg ggcagctctg atgtccatca agctccagtt   1380
ttgggctcca atgaccagat ctgggggaa tgaagtaggt ggagacggag ggtctggtca    1440
aataagttgc agccccgtgt ttgcagtaga aagacctatt gctctaagca agcaagctgt   1500
aagaagaatg ctgtcaatga atattgaggg acgtgatgca gatgtcaaag gaaatctact   1560
caagatgatg aatgattcaa tgactaagaa aaccaatgga aatgctttca ttgggaagaa   1620
aatgtttcaa atatcagaca aaaacaaaac caatcccatt gagattccaa ttaagcagac   1680
catccccaat ttcttctttg ggagggacac agcagaggat tatgatgacc tcgattatta   1740
aagcaacaaa atagacacta tggctgtgac tgtttcagta cgtttggaat gtgggtgttt   1800
acttttattg aaataaatgt aaaaaatgct gttgtttcta ct                       1842
```

UNITED STATES PATENT AND TRADEMARK OFFICE
CERTIFICATE OF CORRECTION

PATENT NO. : 10,030,231 B2
APPLICATION NO. : 14/762439
DATED : July 24, 2018
INVENTOR(S) : Philip Dormitzer et al.

Page 1 of 1

It is certified that error appears in the above-identified patent and that said Letters Patent is hereby corrected as shown below:

In the Claims

Claim 23, Column 278, Lines 14-16, "The method of claim 22, wherein the cell is an MDCK (optionally cell line MDCK 33016 (DSM ACC2219)), Vero or PerC6 cell." should read --The method of claim 22, wherein the cell is an MDCK, Vero or PerC6 cell.--.

Signed and Sealed this
Twenty-fifth Day of September, 2018

Andrei Iancu
*Director of the United States Patent and Trademark Office*